(12) United States Patent
Ganesan et al.

(10) Patent No.: US 8,759,491 B2
(45) Date of Patent: Jun. 24, 2014

(54) MODULATORS OF HEPATOCYTE GROWTH FACTOR ACTIVATOR

(75) Inventors: Rajkumar Ganesan, San Bruno, CA (US); Daniel Kirchhofer, Los Altos, CA (US)

(73) Assignee: Genentech, Inc., South San Francisco, CA (US)

(*) Notice: Subject to any disclaimer, the term of this patent is extended or adjusted under 35 U.S.C. 154(b) by 410 days.

(21) Appl. No.: 12/906,473

(22) Filed: Oct. 18, 2010

(65) Prior Publication Data
US 2011/0091477 A1 Apr. 21, 2011

Related U.S. Application Data

(60) Provisional application No. 61/252,973, filed on Oct. 19, 2009.

(51) Int. Cl.
*C12P 21/08* (2006.01)

(52) U.S. Cl.
USPC ........................................ 530/387.3

(58) Field of Classification Search
None
See application file for complete search history.

(56) References Cited

U.S. PATENT DOCUMENTS

| | | |
|---|---|---|
| 3,773,919 A | 11/1973 | Boswell |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 4,970,198 A | 11/1990 | Lee et al. |
| 4,975,278 A | 12/1990 | Senter et al. |
| 5,053,394 A | 10/1991 | Ellestad et al. |
| 5,079,233 A | 1/1992 | Lee |
| 5,122,469 A | 6/1992 | Mather et al. |
| 5,208,020 A | 5/1993 | Chari et al. |
| 5,264,365 A | 11/1993 | Georgiou et al. |
| 5,416,064 A | 5/1995 | Chari et al. |
| 5,500,362 A | 3/1996 | Robinson et al. |
| 5,508,192 A | 4/1996 | Georgiou et al. |
| 5,585,089 A | 12/1996 | Queen et al. |
| 5,606,040 A | 2/1997 | McGahren et al. |
| 5,624,821 A | 4/1997 | Winter et al. |
| 5,639,635 A | 6/1997 | Joly et al. |
| 5,648,237 A | 7/1997 | Carter |
| 5,648,260 A | 7/1997 | Winter et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,821,337 A | 10/1998 | Carter et al. |
| 5,840,523 A | 11/1998 | Simmons et al. |
| 5,877,296 A | 3/1999 | Hamann et al. |
| 6,027,888 A | 2/2000 | Georgiou et al. |
| 6,083,715 A | 7/2000 | Georgiou et al. |
| 6,407,213 B1 | 6/2002 | Carter et al. |
| 6,800,604 B2 | 10/2004 | Gurney et al. |
| 7,737,115 B2 | 6/2010 | Kirchhofer et al. |

(Continued)

FOREIGN PATENT DOCUMENTS

| | | |
|---|---|---|
| EP | 0 425 235 B1 | 9/1996 |
| EP | 1391213 A1 | 2/2004 |

(Continued)

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Tsai et al., "Protein allostery, signal transmission and dynamics: a classification scheme of allosteric mechanisms" *Molec. BioSystems* 5:207-216 (2009).
Turk, B., "Targeting proteases: successes, failures and future prospects" *Nature Reviews* 5:785-799 (Sep. 2006).
Urlaub and Chasin, "Isolation of chinese hamster cell mutants deficient in dihydrofolate reductase activity" *Proc. Natl. Acad. Sci. USA* 77(7):4216-4220 (Jul. 1980).
Vajpai et al., "Solution conformations and dynamics of ABL kinase-inhibitorcomplexes determined by NMR substantiate the different binding modes of imatinib/nilotinib and dasatinib" *Journal of Biological Chemistry* 283:18292-18302 (2008).

(Continued)

*Primary Examiner* — Brad Duffy
(74) *Attorney, Agent, or Firm* — Stephanie Yonker

(57) ABSTRACT

The invention provides methods and compositions for modulating hepatocyte growth factor activator function.

16 Claims, 19 Drawing Sheets

(56) References Cited

U.S. PATENT DOCUMENTS

| | | |
|---|---|---|
| 7,825,221 B2 | 11/2010 | Kirchhofer et al. |
| 2004/0132660 A1 | 7/2004 | Gurney et al. |
| 2006/0147451 A1 | 7/2006 | Kirchhofer et al. |
| 2010/0210826 A1 | 8/2010 | Kirchhofer et al. |
| 2011/0098449 A1 | 4/2011 | Kirchhofer et al. |

FOREIGN PATENT DOCUMENTS

| | | |
|---|---|---|
| WO | WO 87/00195 | 1/1987 |
| WO | WO 90/03430 | 4/1990 |
| WO | WO 93/21232 | 10/1993 |
| WO | WO 94/11026 | 5/1994 |
| WO | WO 94/29351 | 12/1994 |
| WO | WO 99/51642 | 10/1999 |
| WO | WO 2006/042173 A1 | 4/2006 |
| WO | WO 2006042173 A2 * | 4/2006 |

OTHER PUBLICATIONS van Adelsberg, "Activation of Hepatocyte Growth Factor (HGF) by Endogenous HGF Activator Is Required for Metanephric Kidney Morphogenesis in Vitro" *Journal of Biological Chemistry* 276:15099-15106 (2001).

Vaswani and Hamiton, "Humanized antibodies as potential therapeutic drugs" *Ann. Allergy Asthma & Immunol.* 81:105-115 (Nov. 1998).

Verhoeyen et al., "Reshaping Human Antibodies: Grafting an Antilysozyme Activity" *Science* 239:1534-1536 (Mar 1988).

Vitetta et al., "Redesigning Nature's Poisons to Create Anti-Tumor Reagents" *Science* 238:1098-1104 (1987).

Wells and Di Cera, "Thrombin is a Na$^+$-activated enzyme" *Biochemistry* 31:11721-11730 (1992).

Wiseman et al, "Ibritumomab tiuxetan radioimmunotherapy for patients with relapsed or refractory non-Hodgkin lymphoma and mild thrombocytopenia: a phase II multicenter trial" *Blood* 99(12):4336-4342 (Jun. 15, 2002).

Wiseman, G.A. et al., "Phase I/II $^{90}$Y-Zevalin (yttrium-90 ibritumomab tiuxetan, IDEC-Y2B8) radioimmunotherapy dosimetry results in relapsed or refractory non-Hodgkin's lymphoma" *European J Nuclear Med.* 27(7):766-777 (2000).

Witzig et al, "Randomized Controlled Trial of Yttrium-90—Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma" *Journal of Clinical Oncology*20(10):2453-2463.

Witzig et al, "Treatment With Ibritumomab Tiuxetan Radioimmunotherapy in Patients With Rituximab-Refractory Follicular Non-Hodgkin's Lymphoma" *Journal of Clinical Oncology* 20(15):3262-3269 (Aug. 1, 2002).

Wu, Yan, et al., "Structural insight into distinct mechanisms of protease inhibition by antibodies" *Proc. Natl. Acad. Sci. USA* 104(50):19784-19789 (Dec. 11, 2007).

Xu et al., "The crystal structure of the asymmetric GroEL-GroEs-(ADP)$_7$ chaperonin complex" 388:741-750 (Aug. 21, 1997) Nature.

Yaniv, M., "Enhancing Elements for Activation of Eukaryotic Promoters" *Nature* 297(6):17-18 (May 1982).

Yansura and Simmons, "Nucleotide Sequence Selection for Increased Expression of Heterologous Genes in *Escherichia coli*" *Methods: A Companion to Methods in Enzymology* 4(2):151-158 (1992).

Yelton et al., "Affinity Maturation of the BR96 Anti-Carcinoma Antibody by Codon-Based Mutagenesis" *The Journal of Immunology* 155:1994-2004 (1995).

Yu et al., "Propagating conformational changes over long (and short) distances in proteins" *Proc Natl Acad Sci U S A.* 98(17):9517-20 (2001).

"Gemtuzumab ozogamicin. Treatment of acute myeloid leukemia" *Drugs of the Future* 25(7):686-692 (2000).

"The CCP4 suite: Programs for protein crystallography" *Acta Cryst.* D50:760-763 (1994).

Adams and Weiner, "Monoclonal antibody therapy of cancer" *Nat. Biotech.* 23:1147-1157 (2005).

Arie et al., "Chaperone Function of FkpA, A Heat Shock Prolyl Isomerase, in the Periplasm of *Escherichia coli*" *Molecular Microbiology* 39(1):199-210 (2001).

Baldwin and Byers, "Treatment of Cancer, Monoclonal antibodies in cancer treatment" *Lancet*327(8481):603-605 (1986).

Barbas et al., "In Vitro Evolution of a Neutralizing Human Antibody to Human Immunodeficiency Virus Type 1 to Enhance Affinity and Broaden Strain Cross-Reactivity" *Proc Natl Acad Sci U S A.* 91(9):3809-3813 (Apr. 1994).

Barnes and Sato., "Methods for Growth of Cultured Cells in Serum-Free Medium" *Analytical Biochemistry* 102:255-270 (1980).

Bass et al., "Hormone Phage: An Enrichment Method for Variant Proteins with Altered Binding Properties" *Proteins: Structure, Function, and Genetics* 8(4):309-314 (1990).

Bjelke et al., "Mechanism of the Ca2$^+$-induced enhancement of the intrinsic factor VIIa activity" *J Biol. Chem.* 283:25863-25870 (Sep. 19, 2008).

Bock et al., "Exosites in the substrate specificity of blood coagulation reactions" *J. Thromb. Haemost.* 5(Suppl. 1):81-94 (2007).

Bothmann and Pluckthun, "The Periplasmic *Escherichia coli* Peptidylprolyl cis,trans-Isomerase FkpA" *J Bio Chem.* 275(22):17100-17105 (Jun. 2000).

Bussolino et al., "Hepatocyte Growth Factor is a Potent Angiogenic Factor Which Stimulates Endothelial Cell Motility and Growth" *Journal of Cell Biology* 119(3):629-641 (Nov. 1992).

Carlsson et al., "Protein thiolation and reversible protein-protein conjugation" *Biochemical Journal* 173:723-737 (1978).

Carter et al., "Humanization of an Anti-p185$^{HER2}$ Antibody for Human Cancer Therapy" *Proc Natl Acad Sci U S A.* 89(10):4285-4289 (May 1992).

Changeux et al., "Allosteric mechanisms of signal transduction" *Science* 308:1424-8 (2005).

Chari et al., "Immunoconjugates Containing Novel Maytansinoids: Promising Anticancer Drugs" *Cancer Research* 52:127-131 (Jan. 1992).

Chen et al., "Chaperone Activity of DsbC" *J Bio Chem.* 274(28):19601-19605 (Jul. 1999).

Chothia et al., "Canonical structures for the hypervariable regions of immunoglobulins" *J. Mol. Biol.* 196:901-917 (1987).

Clynes et al., "Fc receptors are required in passive and active immunity to melanoma" *Proc. Natl. Acad. Sci.* (USA) 95:652-656 (Jan. 1998).

International Search Report on Patentability for International Patent Application No. PCT/US2010/053054.

Cunningham and Wells, "High-Resolution Epitope Mapping of hGH-Receptor Interactions by Alanine-Scanning Mutagenesis" *Science* 244:1081-1085 (Jun. 2, 1989).

del Sol et al., "The origin of allosteric functional modulation: multiple pre-existing pathways" *Structure* 17:1042-1050 (2009).

Di Cera et al., "A structural perspective on enzymes activated by monovalent cations" *J Biol Chem.* 28(3):1305-8 (2006).

Doronina et al., "Development of potent monoclonal antibody auristatin conjugates for cancer therapy" *Nature Biotechnology* 21:778-784 (2003).

Duncan and Winter, "The binding site for Clq on IgG" *Nature* 322:738-740 (1988).

Egeblad and Werb, "New functions for the matrix metalloproteinases in cancer progression" *Nature Rev. Cancer* 2:161-174 (Mar. 2002).

Eigenbrot et al., "New insight into how tissue factor allosterically regulates factor VIIa" *Trends Cardiovasc Med.* 12(1):19-26 (Jan 2002).

Farady et al., "Structure of an fab-protease complex reveals a highly specific non-canonical mechanism of inhibition" *J. Molec. Biol.* 380:351-360 (2008).

Fenton, A. W., "Allostery: an illustrated definition for the 'second secret of life'" *Trends in Biochem. Sci.* 33:420-425 (2008).

Friedrich et al., "Staphylocoagulase is a prototype for the mechanism of cofactor-induced zymogen activation" *Nature* 425:535-539 (2003).

Ganesan, R., et al., "Structural and mechanistic insight into how antibodies inhibit serine proteases" *Biochemical Journal* 430:179-189 (2010).

(56) References Cited

OTHER PUBLICATIONS

Ganesan, R., et al., "Unraveling the allosteric mechanism of serine protease inhibition by an antibody" *Structure* 17:1614-1624 (Dec. 2009).
Gazzano-Santoro et al., "A non-radiative complement-dependent cytotoxicity assay for anti-CD20 monoclonal antibody" *J. Immunol. Methods* 202:163-171 (1997).
Geoghegan & Stroh, "Site-directed conjugation of nonpeptide groups to peptides and proteins via periodate oxidation of a 2-amino alcohol. Application to modification at N-terminal serine" *Bioconjugate Chem.* 3:138-146 (1992).
Goodey and Benkovic, "Allosteric regulation and catalysis emerge is a common route" *Nature Chem. Biol.* 4:474-482 (2008).
Graham et al., "Characteristics of a Human Cell Line Transformed by DNA from Human Adenovirus Type 5" *J. Gen Virol.* 36(1):59-72 (Jul. 1977).
Gunasekaran et al., "Is allostery an intrinsic property of all (2004) dynamic proteins?" *Proteins* 57(3):433-43.
Guss et al., "Structure of the IgG-Binding Regions of Streptococcal Protein G" *EMBO Journal* 5(7):1567-1575 (1986).
Ham and McKeehan, "Media and Growth Requirements" *Methods in Enzymology* 58:44-93 (1979).
Hara et al., "Overproduction of Penicillin-Binding Protein 7 Suppresses Thermosensitive Low Osmolarity Due to an spr Mutation of Escherichia coli" *Microb Drug Resist.* 2(1):63-72 Growth Defect at (1996).
Hardy and Wells, "Dissecting an allosteric switch in caspase-7 using chemical andmutational probes" *J Biol. Chem.* 284(38):26063-26069 (Sep. 18, 2009).
Hardy and Wells, "Searching for new allosteric sites in enzymes" *Curr. Op. Struct. Biol.* 14:706-715 (2004).
Hardy et al., "Discovery of an allosteric site in the caspases" *Proc. Natl. Acad. Sci. USA* 101:12461-12466 (Aug. 24, 2004).
Harris, "Production of humanized monoclonal antibodies for in vivo imaging and therapy" *Biochemical Society Transactions* 23(4):1035-1038 (Nov. 1995).
Hauske et al., "Allosteric Regulation of Proteases" *ChemBioChem* 9:2920-2928 (2008).
Hayashi et al., "Inductions of hepatocyte growth factor and its activator in rat brain with permanent middle cerebral artery occlusion" *Brain Research* 799(2):311-6 (1998).
Hedstrom, L., "Serine Protease Mechanism and Specificty" *Chem. Rev.* 102(12):4501-4523 (Dec. 2002).
Herter et al., "Hepatocyte growth factor is a preferred in vitro substrate for human hepsin, a membrane-anchored serine protease implicated in prostate and ovarian cancers" *Biochemical Journal* 390:125-136 (2005).
Hinman et al., "Preparation and Characterization of Monoclonal Antibody conjugates of the Calicheamicins: A Novel and Potent Family of Antitumor Antibiotics" *Cancer Research* 53:3336-3342 (Jul. 15, 1993).
Hoogenboom, "Selecting and screening recombinant antibody libraries" *Nature Biotechnology* 23(9):1105-1116 (Sep. 1, 2005).
Hopfner et al., "Coagulation factor IXa: the relaxed conformation of Tyr99 blocks substrate binding" *Structure* 7(8):989-996 (1999).
Huber and Bode, "Structural Basis of the Activation and Action of Trypsin" *Accounts of Chemical Research* 11:114-122 (1978).
Huntington, J., "How $Na^+$ activates thrombin—a review of the functional and structural data" *Biol. Chem.* 389:1025-1035 (Aug. 2008).
Hurle and Gross, "Protein Engineering Techniques for Antibody Humanization" *Curr Opin Biotechnol.* 5:428-433 (1994).
Itoh et al., "Mouse hepatocyte growth factor activator gene: its expression not only in the liver but also in the gastrointestinal tract" *Biochim Biophys Acta.* 1491(1-3):295-302 (Apr. 25, 2000).
Jackson et al., "In vitro antibody maturation. Improvement of a high affinity, neutralizing antibody against IL-1β" *J Immunol.* 154(7):3310-3319 (1995).
Jones et al., "Replacing the Complementarity-Determining Regions in a Human Antibody with Those From a Mouse" *Nature* 321(6069):522-525 (May 29, 1986).

Kataoka et al., "Activation of Hepatocyte Growth Factor/Scatter Factor in Colorectal Carcinoma" *Cancer Research* 60:6148-6159 (Nov. 1, 2000).
Kataoka et al., "Roles of Hepatocyte Growth Factor (HGF) Activator and HGF Activator Inhibitor in the Pericellular Activation of HGF/Scatter Factor" *Cancer Metastasis Rev* 22(2):223-236 (2003).
Kawaguchi et al., "Hepatocyte growth factor activator is a serum activator of single-chain precursor macrophage-stimulating protein" *FEBS J.* 276(13):3481-90 (2009).
Kawaguchi et al., "Purification and cloning of hepatocyte growth factor activator inhibitor type 2, a Kunitz-type serine protease inhibitor" *J Biol Chem.* 272(44):27558-27564 (Oct. 31, 1997).
Kirchhofer et al., "Tissue expression, protease specificity, and Kunitz domain functions of hepatocyte growth factor activator inhibitor-1B (HAI-1B), a new splice variant of HAI-1" *J Biol Chem.* 278(38):36341-36349 (Sep. 19, 2003).
Lee and Craik, "Trapping moving targets with small molecules" *Science* 324:213-215 (2009).
Lee and Richards, "The interpretation of protein structures: estimation of static accessibility" *J. Mol. Biol.* 55(3):379-400 (1971).
Lee et al., "Bivalent antibody phage display mimics natural immunoglobulin" *J. Immunol. Methods* 284:119-132 (2004).
Lee et al., "High-affinity human antibodies from phage-displayed synthetic Fab libraries with a single framework scaffold" *J Mol Biol.* 340(5):1073-1093 (Jul. 23, 2004).
Liang et al., "Function Blocking Antibodies to Neuropilin-1 Generated from a Designed Human Synthetic Antibody Phage Library" *J. Mol. Biol.* 366:815-829 (2007).
Lindmark et al., "Binding of Immunoglobulins to Protein A and Immunoglobulin Levels in Mammalian Sera" *J. Immunol Meth.* 62:1-13 (1983).
Liu et al., "Eradication of Large Colon Tumor Xenografts by Targeted Delivery of Maytansinoids." *Proc. Natl. Acad. Sci. USA* 93:8618-8623 (1996).
Lode, H., et al., "Targeted therapy with a novel enediyene antibiotic calicheamicin $\theta^1_1$ effectively suppresses growth and dissemination of liver metastases in a syngeneic model of murine neuroblastoma" *Cancer Research* 58:2925-2928 (Jul. 15, 1998).
Luttun et al., "The role of proteinases in angiogenesis, heart development, restenosis, atherosclerosis, kyocardial ischemia, and stroke: insights from genetic studies" *Curr. Atheroscler. Rep.* 2:407-416 (2000).
Mandler et al., "Immunoconjugates of Geldanamycin and Anti-HER2 Monoclonal Antibodies: Antiproliferative Activity on Human Breast Carcinoma Cell Lines" *Journal of the National Cancer Institute* 92(19):1573-1581 (Oct. 4, 2000).
Mandler et al., "Modifications in synthesis strategy improve the yield and efficacy of geldanamycin—herceptin immunoconjugates" *Bioconjugate Chem.* 13:786-791 (2002).
Mandler et al., "Synthesis and Evaluation of Antiproliferative Activity of a Geldanamycin-Herceptin(tm) Immunoconjugate" *Bioorganic & Medicinal Chemistry Letters* 10:1025-1028 (2000).
Marks et al., "By-Passing Immunization: Building High Affinity Human Antibodies by Chain Shuffling" *Bio/Technology* 10:779-783 (Jul. 1992).
Mather et al., "Culture of Testicular Cells in Hormone-Supplemented Serum-Free Medium" *Annals N.Y. Acad. Sci.* 383:44-68 (1982).
Mather, "Establishment and Characterization of Two Distinct Mouse Testicular Epithelial Cell Lines" *Biol. Reprod.* 23:243-252 (1980).
McCoy et al., "Likelihood-enhanced fast translation functions" *Acta Crystallogr D Biol. Crystallogr* 61:458-464 (2005).
Miyazawa et al., "Molecular Cloning and Sequence Analysis of the cDNA for a Human Serine Protease Responsible for Activation of Hepatocyte Growth Factor" *Journal of Biological Chemistry* 268(14):10024-10028 (May 15, 1993).
Moriyama et al., "Concomitant expression of hepatocyte growth (HGF), HGF activator and c-met genes in human glioma cells in vitro" *FEBS Letters* 372(1):78-82 factor (1995).
Morrison et al., "Chimeric Human Antibody Molecules: Mouse Antigen-Binding Domains with Human Constant Region Domains" *Proc. Natl. Acad. Sci. USA* 81(21):6851-6855 (Nov. 1984).

(56) References Cited

OTHER PUBLICATIONS

Nagata et al., "Expression of Hepatocyte Growth Factor Activator and Hepatocyte Growth Factor Activator Inhibitor Type 1 in Human Hepatocellular Carcinoma" *Biochem. & Biophys. Res. Comm.* 289:205-211 (2001).
Nicolaou et al., "Calicheamicin Θ: A Rationally Designed Molecule with Extremely Potent and Selective DNA Cleaving Properties and Apoptosis Inducing Activity" *Angew. Chem. Intl. Ed. Engl.* 33(2):183-186 (1994).
Niculescu-Duvaz and Springer, "Antibody-Directed Enzyme Prodrug Therapy (ADEPT): A Review" *Adv. Drg. Del. Rev.* 26:151-172 (1997).
Olsen and Persson, "Cofactor-induced and mutational activity enhancedment of coagulation factor VIIa" *Cell. Molec. Life Sciences* 65:953-963 (2008).
Otwinowski and Minor, "Processing of X-ray Diffraction Data Collected in Oscillation Mode" *Methods in Enzymology*, Carter and Sweet, San Diego, CA:Academic Press vol. 276:307-326 (1997).
Parr and Jiang, "Expression of hepatocyte growth factor/scatter factor, its activator, inhibitors and the c-Met receptor in human cancer cells" *Int. J. Oncol.* 19:857-863 (2001).
Pellicena and Kuriyan, "Protein-protein interactions in the allosteric regulation of protein kinases" *Current Op. Struct. Biol.* 16:702-709 (2006).
Perutz et al., "Stereochemistry of cooperative effects in haemoglobin" *Nature* 228:726-734 (1970).
Peterson and Golemis, "Autoinhibited proteins as promising drug targets" *J. Cell Biochem.* 93:68-73 (2004).
Presta et al., "Humanization of an Antibody Directed Against IgE" *J Immunol.* 151(5):2623-2632 (Sep. 1, 1993).
Presta, "Antibody Engineering" *Current Opinion in Structural Biology* 2:593-596 (1992).
Proba et al., "Functional Antibody Single-Chain Fragments From the Cytoplasm of *Escherichia coli*: Influence of Thioredoxin Reductase (TrxB)" *Gene* 159:203-207 (1995).
Raddatz et al., "Allosteric approaches to the targeting of G-protein-coupled receptors for novel drug discovery: a critical assessment." *Biochem. Pharmacol.* 74:383-391 (2007).
Ramm and Pluckthun, "The Periplasmic *Escherichia coli* Peptidylprolyl cis,trans Isomerase FkpA" *J Biol Chem.* 275(22):17106-17113 (Jun. 2000).
Ravetch and Kinet, "Fc Receptors" *Ann. Rev. Immunol.* 9:457-492 (1991).
Rawlings et al., "MEROPS: the peptidase database" *Nucleic Acids Research* 36:D320-D325 (2008).
Reyes et al, "Expression of Human β-interferon cDNA Under the Control of a Thymidine Kinase Promoter from Herpes Simplex Virus" *Nature* 297:598-601 (Jun. 17, 1982).
Riechmann et al., "Reshaping Human Antibodies for Therapy" *Nature* 332:323-327 (Mar. 24, 1988).
Rowland et al., "Drug Localisation and Growth Inhibition Studies of Vindesine-Monoclonal anti-CEA Conjugates in a Human Tumour Xenograft" *Cancer Immunol. Immunother.* 21:183-187 (1986).
Shia, S. et al., "Conformational lability in serine protease active sites: structures of hepatocyte growth factor activator (HGFA) alone and with the inhibitory domain from HGFA inhibitor-1B" *J. Mol. Biol.* 346:1335-1349 (2005).
Shimomura et al., "A novel protease obtained from FBS-containing culture supernatant, that processes single chain form hepatocyte growth factor to two chain form in serum-free culture" *Cytotechnology* 8(3):219-29 (1992).
Shimomura et al., "Activation of hepatocyte growth factor by two homologous proteases, blood-coagulation factor XIIa and hepatocyte growth factor activator" *European Journal of Biochemistry* 229(1):257-261 (Apr. 1, 1995).
Shimomura et al., "Activation of the Zymogen of Hepatocyte Growth Factor Activator by Thrombin" *Journal of Biological Chemistry* 268:22927-22932 (1993).
Shimomura et al., "Hepatocyte Growth Factor Activator Inhibitor, a Novel Kunitz-type Serine Protease Inhibitor" *Journal of Biological Chemistry* 272(10):6370-6376 (Mar. 7, 1997).
Siebenlist et al., "*E. Coli* RNA Polymerase Interacts Homologously with Two Different Promoters" *Cell* 20:269-281 (Jun. 1980).
Simmons, L. et al., "Expression of full-length immunoglobulins in *Escherichia coli*: Rapid and efficient production of aglycosylated antibodies" *Journal of Immunological Methods* 263:133-147 (2002).
Sims et al., "A Humanized CD18 Antibody Can Block Function Without Cell Destruction" *The Journal of Immunology* 151(4):2296-2308 (Aug. 15, 1993).
Sohn et al., "Allosteric activation of DegS, a stress sensor PDz protease" *Cell* 131:572-583 (Nov. 2, 2007).
Spraggon et al., "Active site conformational changes of prostasin provide a new mechanism of protease regulation by divalent cations." *Protein Sci.* 18:1081-1094 (2009).
Swain et al., "The changing landscape of protein allostery" *Curr Opin Struct Biol.* 16(1):102-8 (2006).
Syrigos and Epenetos, "Antibody directed enzyme prodrug therapy (ADEPT): A review of the experimental and clinical considerations" *Anticancer Res.* 19:505-613 (1999).
Tereshko et al., "Toward chaperone-assisted crystallography: protein engineering enhancement of crystal packing and X-ray phasing capabilities of a camelid single-domain antibody (VHH) scaffold" *Protein Sci.* 17:1175-1187 (2008).
Thin et al., "Multiple Myeloma Cells Catalyze Hepatocyte Growth Factor (HGF) Activation by Secreting the Serine Protease HGF-activator" *Blood* 104(7):2172-2175 (Oct. 2004).

\* cited by examiner

| Residue | | CDR-L1 | | | | | | | | | | | CDR-L2 | | | | | | | | CDR-L3 | | | | | | | | |
|---|---|---|---|---|---|---|---|---|---|---|---|---|---|---|---|---|---|---|---|---|---|---|---|---|---|---|---|---|---|
| | 24 | 25 | 26 | 27 | 28 | 29 | 30 | 31 | 32 | 33 | 34 | | 50 | 51 | 52 | 53 | 54 | 55 | 56 | | 89 | 90 | 91 | 92 | 93 | 94 | 95 | 96 | 97 |
| Ab39 | R | A | S | Q | D | V | S | T | A | V | A | | S | A | S | F | L | Y | S | | Q | Q | S | Y | T | T | P | P | T |
| Ab40 | R | A | S | Q | D | V | S | T | A | V | A | | S | A | S | F | L | Y | S | | Q | Q | S | N | R | A | P | A | T |
| Ab40.ΔTrp | * | * | * | * | * | * | * | * | * | * | * | | * | * | * | * | * | * | * | | Q | Q | S | - | - | - | - | - | * |

| Residue | | CDR-H1 | | | | | | | CDR-H2 | | | | | | | | | | | | | | | | | | CDR-H3 | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 30 | 31 | 32 | 33 | 34 | 35 | | 49 | 50 | 51 | 52 | 52a | 53 | 54 | 55 | 56 | 57 | 58 | 59 | 60 | 61 | 62 | 63 | 64 | 65 | | 94 | 95 | 96 | 97 | 98 | 99 | 100 | 100a | 101 | 102 |
| Ab39 | N | G | T | Y | I | H | | G | G | I | Y | P | A | G | G | A | T | Y | Y | A | D | S | V | K | G | | K | W | W | A | W | P | A | F | D | Y |
| Ab40 | N | G | T | Y | I | H | | G | G | I | Y | P | A | G | G | A | T | Y | Y | A | D | S | V | K | G | | K | W | W | A | W | P | A | F | D | Y |
| Ab40.ΔTrp | * | * | * | * | * | * | | * | * | * | * | * | * | * | * | * | * | * | * | * | * | * | * | * | * | | K | W | - | A | W | P | A | F | D | Y |

FIG. 1

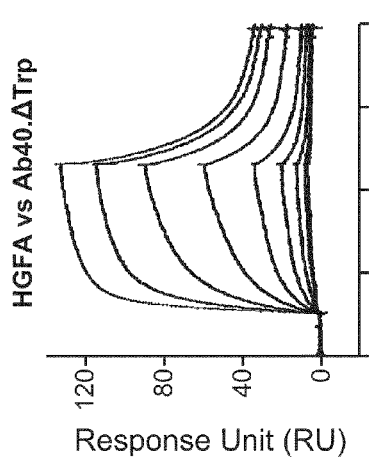
FIG. 3E
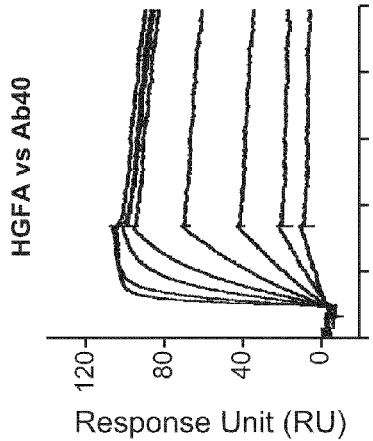
FIG. 3F
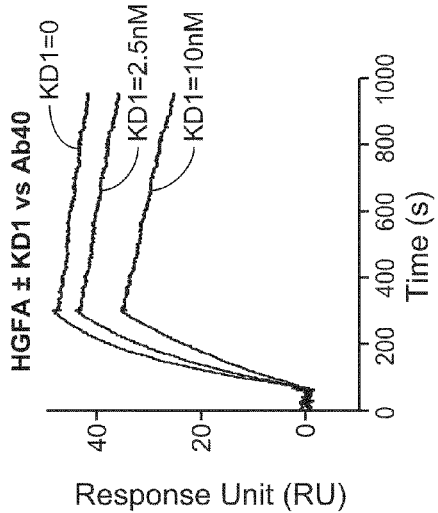
FIG. 3C
FIG. 3D
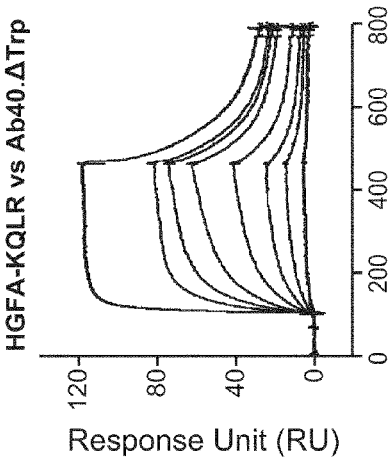
FIG. 3A
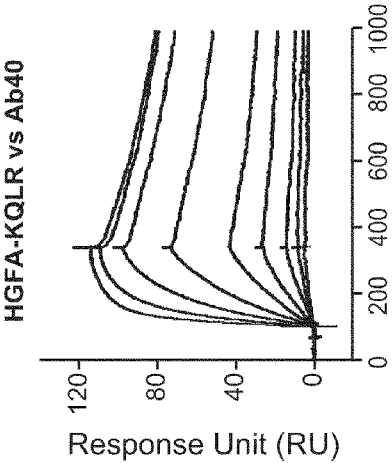
FIG. 3B

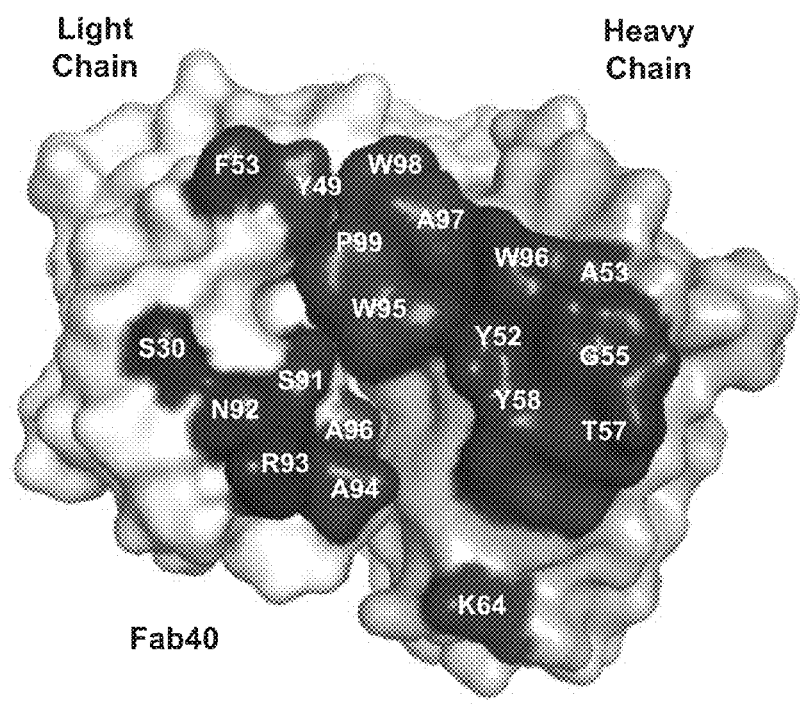
FIG. 5C
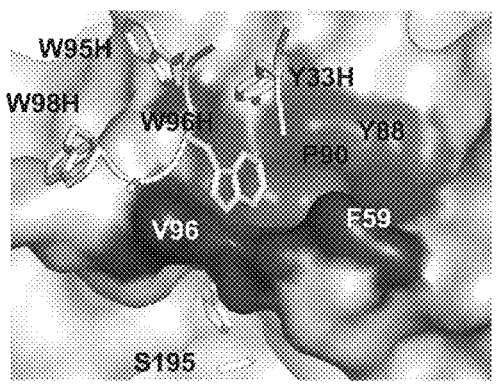 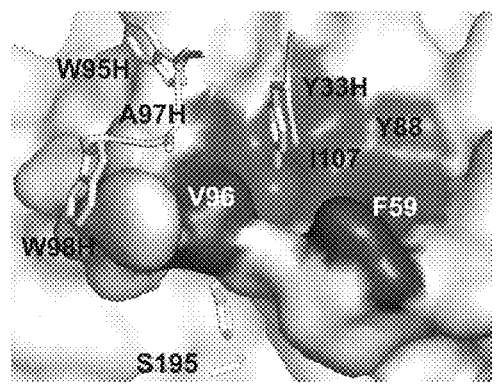
FIG. 6A　　　　FIG. 6B

HGFA
Switch "OFF" (Competent State)

HGFA/Fab40
Switch "ON" (Non-competent State)

HGFA/Fab40.ΔTrp
Switch "OFF" (Competent State)

HGFA/Fab40.ΔTrp
Switch "OFF" (Competent State)

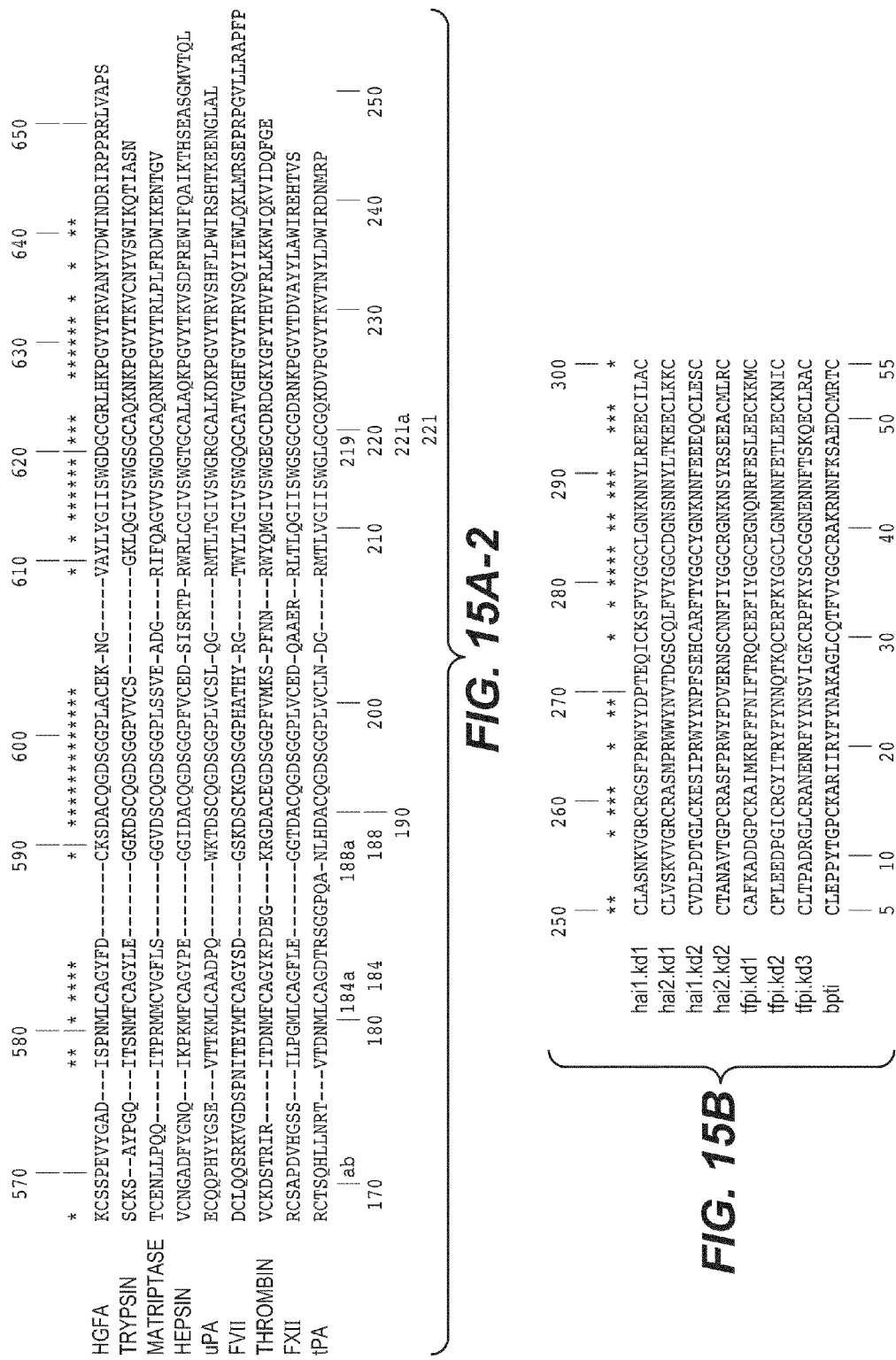

Light Chain Variable Domain Sequence

| Kabat# | 1 2 3 4 5 6 7 8 9 10 11 12 13 14 15 16 17 18 19 20 21 22 23 24 25 26 27 A B C D E F 28 29 30 31 32 33 34 35 36 |
|---|---|
| | Kabat - CDR L1 |
| | Chothia - CDR L1 |
| | Contact - CDR L1 |
| Ab40 | D I Q M T Q S P S S L S A S V G D R V T I T C R A S Q - - - - - - D V S T A V A W Y |
| Ab40.ΔTrp | D I Q M T Q S P S S L S A S V G D R V T I T C R A S Q - - - - - - D V S T A V A W Y |

| Kabat# | 37 38 39 40 41 42 43 44 45 46 47 48 49 50 51 52 53 54 55 56 57 58 59 60 61 62 63 64 65 66 67 68 69 70 71 72 73 74 75 76 77 78 |
|---|---|
| | Kabat - CDR L2 |
| | Chothia - CDR L2 |
| | Contact - CDR L2 |
| Ab40 | Q Q K P G K A P K L L I Y S A S F L Y S G V P S R F S G S G S G T D F T L T I S S L |
| Ab40.ΔTrp | Q Q K P G K A P K L L I Y S A S F L Y S G V P S R F S G S G S G T D F T L T I S S L |

| Kabat# | 79 80 81 82 83 84 85 86 87 88 89 90 91 92 93 94 95 96 97 98 99 100 101 102 103 104 105 106 107 108 |
|---|---|
| | Kabat - CDR L3 |
| | Chothia - CDR L3 |
| | Contact - CDR L3 |
| Ab40 | Q P E D F A T Y Y C Q Q S N R A P A T F G Q G T K V E I K R   SEQ ID NO:8 |
| Ab40.ΔTrp | Q P E D F A T Y Y C Q Q S N R A P A T F G Q G T K V E I K R   SEQ ID NO:8 |

*FIG. 16A*

Heavy Chain Variable Domain Sequence

| Kabat# | 1 2 3 4 5 6 7 8 9 10 11 12 13 14 15 16 17 18 19 20 21 22 23 24 25 26 27 28 29 30 31 32 33 34 35 A B 36 37 38 49 40 |
|---|---|
| Ab40 | E V Q L V E S G G G L V Q P G G S L R L S C A A S G F T F N G T Y I H - - W V R Q A |
| Ab40.ΔTrp | E V Q L V E S G G G L V Q P G G S L R L S C A A S G F T F N G T Y I H - - W V R Q A |

Kabat - CDR H1
Chothia - CDR H1
Contact - CDR H1

| Kabat# | 41 42 43 44 45 46 47 48 49 50 51 52 A 53 54 55 56 57 58 59 60 61 62 63 64 65 66 67 68 69 70 71 72 73 74 75 76 77 78 79 80 81 |
|---|---|
| Ab40 | P G K G L E W V G G I Y P A G G A T Y Y A D S V K G R F T I S R D N S K N T L Y L Q |
| Ab40.ΔTrp | P G K G L E W V G G I Y P A G G A T Y Y A D S V K G R F T I S R D N S K N T L Y L Q |

Kabat - CDR H2
Chothia - CDR H2
Contact - CDR H2

| Kabat# | 82 A B C 83 84 85 86 87 88 89 90 91 92 93 94 95 96 97 98 99 100 100A 102 103 104 105 106 107 108 109 110 111 112 113 |
|---|---|
| Ab40 | M N S L R A E D T A V Y Y C A K W W A W P A F D Y W G Q G T L V T V S S | SEQ ID NO:9 |
| Ab40.ΔTrp | M N S L R A E D T A V Y Y C A K W - A W P A F D Y W G Q G T L V T V S S | SEQ ID NO:42 |

Kabat - CDR H3
Chothia - CDR H3
Contact - CDR H3

FIG. 16B

MODULATORS OF HEPATOCYTE GROWTH FACTOR ACTIVATOR

CROSS-REFERENCE TO RELATED APPLICATIONS

This application claims the benefit of U.S. Provisional Patent Application No. 61/252,973, filed Oct. 19, 2009, the contents of which is incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 15, 2010, is named P4334RUS.txt and is 42,953 bytes in size.

TECHNICAL FIELD

The present invention relates generally to the fields of molecular biology and growth factor regulation. More specifically, the invention concerns modulators of hepatocyte growth factor activator function, and uses of said modulators.

BACKGROUND

Hepatocyte growth factor activator (HGFA) is a plasma trypsin-like serine protease secreted mainly by the liver that regulates the mitogenic, motogenic, and morphogenic activities of hepatocyte growth factor (HGF, also known as scatter factor (SF)) (Shimomura et al., *Cytotech.*, 8:219-229 (1992)). HGF is implicated in embryonic development, tissue regeneration and invasive tumor growth. This activity requires proteolytic processing of HGF into a two-chain, disulfide-linked α,β-heterodimeric form. HGFA is among the most potent activators of HGF identified so far. (Shimomura et al., *Eur. J. Biochem.* 229 (1995)). HGFA expression has been reported in normal gastrointestinal renal tissues, and in the central nervous system, as well as in pancreatic, hepatocellular, colorectal, prostatic, and lung cancer cells. (Itoh et al., *Biochim. Biophys. Acta,* 1491:295-302 (2000); van Adelsberg et al., *J. Biol. Chem.,* 276:15099-15106 (2001); Hayashi et al., *Brain Res.,* 799:311-316 (1998); Moriyama et al., *FEBS Lett.,* 372: 78-82 (1995); Parr et al., *Int. J. Oncol.,* 19:857-863 (2001); Kataoka et al., *Cancer Res.,* 60:6148-6159 (2000); Nagata et al., *Biochem. Biophys. Res. Comm.,* 289:205-211 (2001)). Recently, HGFA secretion from multiple myeloma cells has been linked to the potent para- and/or autocrine effect of HGF. (Tjin et al., *Blood,* 104:2172-2175 (2004)).

HGFA is secreted as a 96 kDa zymogen (proHGFA) with a domain structure like that of coagulation factor XII (FXIIa), comprising 6 domains. Those domains include an N-terminal fibronectin type II domain, an epidermal growth factor (EGF)-like domain, a fibronectin type 1 domain, another EGF-like domain, a kringle domain, and a C-terminal trypsin homology serine protease domain. (Miyazawa, et al., *J. Biol. Chem.,* 268:10024-10028 (1993)). Cleavage at a kallikrein-sensitive site between residues Arg372 and Va1373 can produce a short 34 kDa form that lacks the first 5 domains. Both the 96 kDa and 34 kDa forms of proHGFA can be cleaved between residues Arg407 and Ile408 into active HGFA by thrombin. (Shimomura et al., *J. Biol. Chem.,* 268, 22927-22932 (1993)). Thrombin is the ultimate effector of procoagulant stimuli and generation of active HGFA would be consistent with the activity of HGF in wound repair. (Bussolino et al., *J. Cell Biol.,* 119:625-641 (1992)).

Among factors influencing HGF/Met signaling are the activation of proHGFA and subsequent inhibition of HGFA. The identified physiological inhibitors of HGFA are the splice variants HAI-1 and HAI-1B (hepatocyte growth factor activator inhibitor-1), and HAI-2 (also known as placental bikunin) (Shimomura et al., *J. Biol. Chem.,* 272:6370-6376 (1997); Kawaguchi et al., *J. Biol. Chem.,* 272:27558-27564 (1997); Kirchhofer et al., *J. Biol. Chem.* 278:36341-36349 (2003)). HGFA has restricted substrate specificity (Kataoka et al., Cancer metastasis reviews 22, 223-239 (2005); Miyazawa et al., *J Biol Chem* 268, 10024-10028 (1993)): only two macromolecular substrates, pro-hepatocyte growth factor (pro-HGF) (Shinomura et al., *Eur J Biochem* 229, 257-261 (1995) and pro-macrophage stimulating protein (pro-MSP) (Kawaguchi et al, *Febs J* 276(13)3481-3490 (2009), are known to be processed by HGFA, exemplifying the enzyme's highly restricted substrate specificity. HGFA is inhibited by the Kunitz-type inhibitor HGFA inhibitor-1, which utilizes the N-terminal Kunitz domain-1 (KD1) to inhibit HGFA by a canonical inhibition mechanism (Shia et al., *J Mol Bio* 346, 1335-13492005). HGFA effects tissue regeneration and promotes cancer growth via pro-HGF processing and ensuing activation of the HGF/Met signaling pathway (Parr and Jiang, Int'l J of Oncol 19, 857-863 (2001)).

Allosteric regulation of an enzyme, by definition, involves an altered catalytic activity originating from a remote effector interaction site. In fact, all dynamic proteins (monomeric and multimeric) seem to have a potential for allosterism (Gunasekaran et al., *Proteins* 57, 433-443 (2004)). Elucidation of allosteric modulation and its pathways of communication have received considerable attention (Swain and Gierasch, *Curr Op in Structural Biol* 16, 102-108 (2006); Yu and Koshland, *PNAS* 98, 9517-9520 (2001)). A classic example of allostery is observed in hemoglobin (Perutz, *Nature* 228, 726-739 (1970)), which offered the first mechanistic insights on allosteric regulation. Several X-ray crystallographic studies emerged thereafter describing the conformational changes during allosteric regulation (Changeux and Edelstein, *Science* 308, 1424-1428 (2005); Di Cera, *J Biol Chem* 281, 1305-1308 (2006); Pellicena and Kuriyan, *Nature* 228, 726-739 (2006); Xu et al., *Nature* 388, 741-750 (1997)). Allostery is also a quite common and powerful mechanism to regulate the catalytic activity of proteases (Hauske et al., *Chembiochem* 9, 2920-2928 (2008); Turk, *Nature Reviews* 5, 785-799 (2006)). Unlike active sites, distally located allosteric sites are usually less conserved and can be exploited to achieve specificity (Hauske et al., supra). Allosteric anti-protease protein-based agents have great therapeutic potential, since they are potent and highly specific and are safeguarded from any inadvertent processing by their target protease. Examples of allosteric regulators in the serine protease family (Clan PA, Family S1 in MEROPS nomenclature (Rawlings et al., *Nucleic Acids Res* 36, D320-325 (2008))) are the accessory PDZ domains in the HtrA protease family (Sohn et al., Cell 131, 572-583 (2007)), calcium for many coagulation factors (Bjelke et al., *J Biol Chem* 283, 25863-25870 (2008)), sodium for thrombin (Huntington, *Biological chemistry* 389, 1025-1035 (2008); Wells and Di Cera, *Biochem* 31, 11721-11730 (1992)), cofactors such as tissue factor for coagulation factor VIIa (Eigenbrot and Kirchhofer, *Trends in Cardiovascular Med* 12, 19-26 (2002)) and N-terminal peptide insertion into the "activation pocket" (Friedrich et al., *Nature* 425, 535-539 (2003); Huber and Bode, *Acc Chem Res* 11, 114-122 (1978)).

Proteases have been implicated in many human pathological processes (Barrett et al., (1998). Handbook of Proteolytic Enzymes. San Diego: Academic Press (1998); Egeblad and Werb, Nature Rev Cancer 2, 161-174 (2002); Hooper, Proteases in Biology and Medicine. In Essays in Biochemistry, London: Portland Press (2002); Luttun et al., Curr Atheroscler. Rep 2, 407-416 (2000)). Therefore, regulation of proteolytic activity by allosteric inhibitors might represent a promising alternative approach to active site inhibitors (Peterson and Golemis, J Cell Biochem 93, 68-73 (2004)), which often suffer from inadequate specificity, since active site topologies are generally conserved among members of the same family (Hedstrom, Chem Revs 102, 4501-4524 (2002)). Unlike active sites, distally located allosteric sites are usually less conserved and can be exploited to achieve specificity (Hauske et al., supra). Excellent examples of specific and potent allosteric inhibitors have been described for coagulation factor VIIa and caspases (Hardy et al., PNAS 101, 12461-12466 (2004); Hardy and Wells, Curr Op Structural Biol 14, 706-715 (2009)).

Since activation of pro-HGF requires cleavage by a convertase such as HGFA, modulation of HGFA function and/or its interaction with its substrate could prove to be an efficacious therapeutic approach. In this regard, there is a clear need to identify clinically relevant agents capable of modulating activity of and/or specifically interacting with HGFA. The invention fulfills this need and provides other benefits.

All publications, patents, and patent documents are incorporated by reference herein, as though individually incorporated by reference.

DISCLOSURE OF THE INVENTION

The invention provides methods, compositions, kits and articles of manufacture for modulating hepatocyte growth factor activator (HGFA) function, thereby modulating physiological effects of HGFA activity. Modulation of HGFA function can be effected by the use of antibodies as described herein. Described herein are anti-HGFA antibodies which allosterically inhibit HGFA function. Allosteric anti-protease antibodies may have great therapeutic potential, since they are potent and highly specific and are safeguarded from any inadvertent processing by their target protease.

In one aspect, the invention provides anti-HGFA therapeutic agents suitable for therapeutic use and capable of effecting varying degrees of disruption of the HGF/c-met signaling pathway. For example, the invention provides an isolated anti-HGFA antibody, wherein a full length IgG form of the antibody specifically binds human HGFA with a binding affinity of less than or equal to 20 pm. In one embodiment, the isolated anti-HGFA antibody specifically binds human HGFA with a $K_{on}$ of about $10 \times 10^5$ $M^{-1}s^{-1}$ or faster. In one embodiment, the isolated anti-HGFA antibody specifically binds human HGFA with a $K_{off}$ of about $1.7 \times 10^{-4} s^{-1}$ or slower.

In one embodiment, the invention provides an affinity matured anti-HGFA antibody wherein the bivalent affinity of the antibody to human HGFA is lower, for example at least 3, 5, 7 or 10-fold lower, or more, such as forty-fold or sixty-fold or more than the bivalent affinity of an antibody comprising, consisting or consisting essentially of (a) HVR-L1 comprising sequence RASQDVSTAVA (SEQ ID NO:1); (b) HVR-L2 comprising sequence SASFLYS (SEQ ID NO:2); (c) HVR-L3 comprising sequence QQSYTTPPT (SEQ ID NO:7); (d) HVR-H1 comprising sequence GTYIH (SEQ ID NO:4); (e) HVR-H2 comprising sequence GIYPAGGATYYADSVKG (SEQ ID NO:5); and (f) HVR-H3 comprising sequence WWAWPAFDY (SEQ ID NO:6).

As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody of the invention (A) has an affinity that is "3-fold lower" than the affinity of a reference antibody (M), then if the Kd value for A is 3×, the Kd value of M would be 1×, and the ratio of Kd of A to Kd of M would be 3:1. Conversely, in one embodiment, if an antibody of the invention (C) has an affinity that is "3-fold greater" than the affinity of a reference antibody (R), then if the Kd value for C is 1×, the Kd value of R would be 3×, and the ratio of Kd of C to Kd of R would be 1:3. Any of a number of assays known in the art, including those described herein, can be used to obtain binding affinity measurements, including, for example, Biacore, radioimmunoassay (RIA) and ELISA.

In one aspect, the invention provides an isolated anti-HGFA antibody, wherein the antibody binds to at least one, two, three, four, or any number up to all of residues 446, 449, 450, 452, 453, 455, 480, 481, 482, 483, 484, 485, 486, 487, 488, 489, 490, 491, 496, 499, 501, 578, 579, 580, 636, 637, 640, 643, 644 of HGFA, and further wherein the antibody allosterically inhibits HGFA and competes for binding to HGFA with HGFA active site blocker KD1 or Ac-KQLR-chloromethyl ketone ("KQLR" disclosed as SEQ ID NO: 10), but does not compete for binding to HGFA with benzamidine. In some embodiments, the antibody binds HGFA in the absence of a compound that blocks HGFA active (catalytic) site, but does not bind HGFA in the presence of the compound that blocks HGFA active site. In some embodiments, the antibody competitively inhibits HGFA activation of HGFA substrate. In some embodiments, the antibody binds to at least one, two, three, four, or any number up to all of residues 449, 450, 452, 482, 484, 485, 486, 487, 488, 489, 490, 491 of HGFA. In some embodiments, the antibody binds to at least one, two, three, four, or any number up to all of residues 446, 482, 484, 490, 499, 501 of HGFA.

In one aspect, the invention provides an isolated anti-HGFA antibody comprising: at least one, two, three, four, five, and/or six hypervariable region (HVR) sequences selected from the group consisting of: (a) HVR-L1 comprising sequence RASQDVSTAVA (SEQ ID NO:1); (b) HVR-L2 comprising sequence SASFLYS (SEQ ID NO:2); (c) HVR-L3 comprising sequence QQSNRAPAT (SEQ ID NO:3); (d) HVR-H1 comprising sequence GTYIH (SEQ ID NO:4); (e) HVR-H2 comprising sequence GIYPAGGATYYADSVKG (SEQ ID NO:5); and (f) HVR-H3 comprising sequence WWAWPAFDY (SEQ ID NO:6). In some embodiments, HVR-H1 comprises sequence NGTYIH (SEQ ID NO: 43). In some embodiments, HVR-H1 comprises sequence GFTFNGTYIH (SEQ ID NO: 44). In some embodiments, HVR-H2 comprises sequence GGIYPAGGATYY (SEQ ID NO: 45). In some embodiments, HVR-H3 comprises sequence KWWAWPAFDY (SEQ ID NO: 46).

In one aspect, the invention provides an anti-HGFA antibody comprising a light chain comprising (a) HVR-L1 comprising sequence RASQDVSTAVA (SEQ ID NO:1); (b) HVR-L2 comprising sequence SASFLYS (SEQ ID NO:2); (c) HVR-L3 comprising sequence QQSNRAPAT (SEQ ID NO:3).

In one aspect, the invention provides an anti-HGFA antibody comprising a heavy chain comprising (a) HVR-H1 comprising sequence GTYIH (SEQ ID NO:4); (b) HVR-H2 comprising sequence GIYPAGGATYYADSVKG (SEQ ID NO:5); and (c) HVR-H3 comprising sequence WWAWPAFDY (SEQ ID NO:6)).

In one aspect, the invention provides an anti-HGFA antibody comprising a light chain comprising (a) HVR-L1 comprising sequence RASQDVSTAVA (SEQ ID NO:1); (b) HVR-L2 comprising sequence SASFLYS (SEQ ID NO:2); (c) HVR-L3 comprising sequence QQSNRAPAT (SEQ ID NO:3); and a heavy chain variable region comprising (d) HVR-H1 comprising sequence GTYIH (SEQ ID NO:4); (e) HVR-H2 comprising sequence GIYPAGGATYYADSVKG (SEQ ID NO:5); and (f) HVR-H3 comprising sequence WWAWPAFDY (SEQ ID NO:6).

In one embodiment, an anti-HGFA antibody of the invention comprises a light chain variable domain having the sequence:
DIQMTQSPSSLSASVGDRVTITCRASQD-VSTAVAWYQQKPGKAPKLLIYS ASFLYSGVPSRF-SGSGSGTDFTLTISSLQPEDFATYYC-QQSNRAPATFGQGTKVEI KR (SEQ ID NO:8); and further comprises a heavy chain variable domain.

In one embodiment, an anti-HGFA antibody of the invention comprises a heavy chain variable domain having the sequence: EVQLVESGGGLVQPGGSLRLSCAASGFT-FNGTYIHWVRQAPGKGLEWVGGIYPA GGATYYADS-VKGRFTISRDNSKNTLYLQMNSLRAED-TAVYYCAKWWAWPAFD YWGQGTLVTVSS (SEQ ID NO:9); and further comprises a light chain variable domain.

In one embodiment, an anti-HGFA antibody of the invention comprises a light chain variable domain having the sequence:
DIQMTQSPSSLSASVGDRVTITCRASQD-VSTAVAWYQQKPGKAPKLLIYS ASFLYSGVPSRF-SGSGSGTDFTLTISSLQPEDFATYYC-QQSNRAPATFGQGTKVEI KR (SEQ ID NO:8); and a heavy chain variable domain having the sequence:

```
                                           (SEQ ID NO: 9)
EVQLVESGGGLVQPGGSLRLSCAASGFTFNGTYIHWVRQAPGKGLEW

VGGIYPAGGATYYADSVKGRFTISRDNSKNTLYLQMNSLRAEDTAVY

YCAKWWAWPAFDYWGQGTLVTVSS.
```

Antibodies of the invention can further comprise any suitable framework and/or light chain variable domain sequences, provided HGFA binding activity is substantially retained. For example, in some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, these antibodies comprise heavy chain variable domain framework sequences of humanized 4D5 antibody (huMAb 4D5-8) (HERCEPTIN®, Genentech, Inc., South San Francisco, Calif., USA) (also referred to in U.S. Pat. No. 6,407,213 and Lee et al., J. Mol. Biol. (2004), 340(5):1073-93). In one embodiment, the humanized 4D5-8 antibody is as described in U.S. Pat. No. 6,407,213. In one embodiment, these antibodies further comprise a human κI light chain framework consensus sequence.

In one aspect, the invention provides an antibody that competes with any of the above-mentioned antibodies for binding to HGFA. In one aspect, the invention provides an antibody that binds to the same epitope on HGFA as any of the above-mentioned antibodies.

In one embodiment, an antibody of the invention is affinity matured, humanized, chimeric, or human. In one embodiment, an antibody of the invention is an antibody fragment (as described herein), or a substantially full length antibody. In one embodiment, an antibody of the invention comprises a wild type Fc region, or a variant thereof. In one embodiment, an antibody of the invention is an IgG (e.g., IgG1, IgG2, IgG3, IgG4), IgM, IgE or IgD.

In one aspect, an antibody of the invention is linked to a toxin such as a cytotoxic agent. These molecules/substances can be formulated or administered in combination with an additive/enhancing agent, such as a radiation and/or chemotherapeutic agent.

The HGF/c-met signaling pathway is involved in multiple biological and physiological functions, including, e.g., cell growth stimulation (e.g. cell proliferation, cell survival, cell migration, cell morphogenesis) and angiogenesis. Thus, in another aspect, the invention provides a method of inhibiting c-met activated cell growth (e.g. proliferation and/or survival), said method comprising contacting a cell or tissue with an antibody of the invention, whereby cell proliferation associated with c-met activation is inhibited. In yet another aspect, the invention provides a method of inhibiting angiogenesis, said method comprising administering to a cell, tissue, and/or subject with a condition associated with abnormal angiogenesis an antibody of the invention, whereby angiogenesis is inhibited.

In one aspect, the invention provides use of an antibody of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder In one aspect, the invention provides a method of inhibiting c-met activated cell proliferation, said method comprising contacting a cell or tissue with an effective amount of an antibody of the invention, whereby cell proliferation associated with c-met activation is inhibited.

In one aspect, the invention provides a method of treating a pathological condition associated with dysregulation of c-met activation in a subject, said method comprising administering to the subject an effective amount of an antibody of the invention, whereby said condition is treated.

In one aspect, the invention provides a method of inhibiting the growth of a cell that expresses c-met or hepatocyte growth factor, or both, said method comprising contacting said cell with an antibody of the invention thereby causing an inhibition of growth of said cell. In one embodiment, the cell is contacted by HGF expressed by a different cell (e.g., through a paracrine effect).

In one aspect, the invention provides a method of therapeutically treating a mammal having a cancerous tumor comprising a cell that expresses c-met or hepatocyte growth factor, or both, said method comprising administering to said mammal an effective amount of an antibody molecule of the invention, thereby effectively treating said mammal. In one embodiment, the cell is contacted by HGF expressed by a different cell (e.g., through a paracrine effect).

In one aspect, the invention provides a method for treating or preventing a cell proliferative disorder associated with increased expression or activity of HGFA, said method comprising administering to a subject in need of such treatment an effective amount of an antibody of the invention, thereby effectively treating or preventing said cell proliferative disorder. In one embodiment, said proliferative disorder is cancer.

In one aspect, the invention provides a method for treating or preventing a cell proliferative disorder associated with increased expression or activity of c-met or hepatocyte growth factor, or both, said method comprising administering to a subject in need of such treatment an effective amount of an antibody of the invention, thereby effectively treating or preventing said cell proliferative disorder. In one embodiment, said proliferative disorder is cancer.

In one aspect, the invention provides a method for inhibiting the growth of a cell, wherein growth of said cell is at least in part dependent upon a growth potentiating effect of HGFA, said method comprising contacting said cell with an effective amount of an antibody of the invention, thereby inhibiting the growth of said cell. In one embodiment, the cell is contacted by HGF expressed by a different cell (e.g., through a paracrine effect).

In one aspect, the invention provides a method for inhibiting the growth of a cell, wherein growth of said cell is at least in part dependent upon a growth potentiating effect of c-met or hepatocyte growth factor, or both, said method comprising contacting said cell with an effective amount of an antibody of the invention, thereby inhibiting the growth of said cell. In one embodiment, the cell is contacted by HGF expressed by a different cell (e.g., through a paracrine effect).

In one aspect, the invention provides a method of therapeutically treating a tumor in a mammal, wherein the growth of said tumor is at least in part dependent upon a growth potentiating effect of HGFA, said method comprising contacting said cell with an effective amount of an antibody of the invention, thereby effectively treating said tumor. In one embodiment, the cell is contacted by HGF expressed by a different cell (e.g., through a paracrine effect).

In one aspect, the invention provides a method of therapeutically treating a tumor in a mammal, wherein the growth of said tumor is at least in part dependent upon a growth potentiating effect of c-met or hepatocyte growth factor, or both, said method comprising contacting said cell with an effective amount of an antibody of the invention, thereby effectively treating said tumor. In one embodiment, the cell is contacted by HGF expressed by a different cell (e.g., through a paracrine effect).

Methods of the invention can be used to affect any suitable pathological state, for example, cells and/or tissues associated with dysregulation of the HGF/c-met signaling pathway, e.g. through increased HGF activity associated with HGFA activation of HGF. In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a prostate cancer cell, a gastric carcinoma cell, a head and neck squamous carcinoma cell, a mesothelioma cell, a melanoma cell and a leukemia cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

As described herein, HGF/c-met activation is an important biological process the dysregulation of which leads to numerous pathological conditions. Accordingly, in one embodiment of methods of the invention, a cell that is targeted (e.g., a cancer cell) is one in which activation of HGF/c-met is enhanced as compared to a normal cell of the same tissue origin. In one embodiment, a method of the invention causes the death of a targeted cell. For example, contact with a modulator molecule of the invention may result in a cell's inability to signal through the c-met pathway, which results in cell death.

Dysregulation of c-met activation (and thus signaling) can result from a number of cellular changes, including, for example, overexpression of HGF (c-met's cognate ligand) and/or HGFA, and/or increased activation of HGF by HGFA. Accordingly, in some embodiments, a method of the invention comprises targeting a tissue wherein one or more of HGFA, c-met and hepatoctye growth factor, is more abundantly expressed and/or present (e.g., a cancer) as compared to a normal tissue of the same origin. An HGF or c-met-expressing cell can be regulated by HGFA from a variety of sources, i.e. in an autocrine or paracrine manner. For example, in one embodiment of methods of the invention, a targeted cell is contacted/bound by hepatocyte growth factor activated by HGFA expressed in a different cell (e.g., via a paracrine effect). Said different cell can be of the same or of a different tissue origin. In one embodiment, a targeted cell is contacted/bound by HGF activated by HGFA expressed by the targeted cell itself (e.g., via an autocrine effect/loop).

In one aspect, the invention provides compositions comprising one or more antibody of the invention and a carrier. In one embodiment, the carrier is pharmaceutically acceptable.

In one aspect, the invention provides nucleic acids encoding an antibody of the invention. In one embodiment, a nucleic acid of the invention encodes a modulator molecule which is or comprises an antibody or fragment thereof.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antibody of the invention. For example, the invention provides a method of making a modulator molecule which is or comprises an antibody (or fragment thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (for e.g., the antibody) to a subject.

In one aspect, the invention provides a kit comprising a first container comprising a composition comprising one or more antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In one embodiment, a kit further comprises instructions for administering the composition (for e.g., the antibody) to a subject.

In one aspect the invention provides a method of diagnosing a disease comprising determining the level of HGFA in a test sample of tissue cells by contacting the sample with an antibody of the invention, whereby HGFA bound by the antibody indicates presence and/or amount of HGFA in the sample. In another aspect, the invention provides a method of determining whether an individual is at risk for a disease comprising determining the level of HGFA in a test sample of tissue cell by contacting the test sample with an antibody of the invention and thereby determining the amount of HGFA present in the sample, wherein a higher level of HGFA in the test sample, as compared to a control sample comprising normal tissue of the same cell origin as the test sample, is an indication that the individual is at risk for the disease. In one embodiment of methods of the invention, the level of HGFA is determined based on amount of HGFA polypeptide indicated by amount of HGFA bound by the antibody in the test sample. An antibody employed in the method may optionally be detectably labeled, attached to a solid support, or the like.

In one aspect, the invention provides a method of binding an antibody of the invention to HGFA present in a bodily fluid, for example blood.

In yet another aspect, the invention is directed to a method of binding an antibody of the invention to a cell that expresses and/or is responsive to HGFA, wherein the method comprises contacting said cell with said antibody under conditions which are suitable for binding of the antibody to HGFA and allowing binding therebetween. In one embodiment, binding of said antibody to HGFA on the cell inhibits an HGFA biological function. In one embodiment, said antibody does not inhibit interaction of HGFA with its substrate molecule. In one embodiment, said antibody binds to an HGFA molecule on the cell and inhibits binding of another molecule (such as pro-HGF) to the HGFA molecule.

In one aspect, the invention provides a method of targeting a therapeutic agent to an HGFA-associated tissue in a host, the method comprising administering to the host said therapeutic agent in a form that is linked to an antibody of the invention, whereby the agent is targeted to the HGFA-associated tissue in the host. In one embodiment, the antibody that binds HGFA is capable of specifically binding to HGFA located on a cell (either in vitro or in vivo), for example where HGFA is present on the surface of a cell.

BRIEF DESCRIPTION OF THE DRAWINGS

FIG. 1 discloses "CDR-L1" as SEQ ID NOS 1, 1, and 1, "CDR-L2" as SEQ ID NOS 2, 2, and 2, "CDR-L3" as SEQ ID NOS 22, 3, and 3, "CDR-H1" as SEQ ID NOS 23, 23, and 23, "CDR-H2" as SEQ ID NOS 47, 47, and 47, and "CDR-H3" as SEQ ID NOS 46, 46, and 24, all respectively, in order of appearance.

FIG. 3: Effects of active site inhibitors on antibody binding to HGFA. (a-b, e-f) Surface plasmon resonance (BIAcore) measurements of binding to immobilized antibodies, Ab40 (a-b) or Ab40.ΔTrp (e-f), after co-injection of HGFA (a,e) or HGFA-KQLR (b, f) complex ("KQLR" disclosed as SEQ ID NO: 10). (c) Competition binding (BIAcore) of HGFA to immobilized Ab40 in presence of different concentrations of KD1. (d) Competition binding ELISA measuring binding of HGFA to biotinylated KD1 in the presence of increasing antibody concentrations.

Figure 2A:
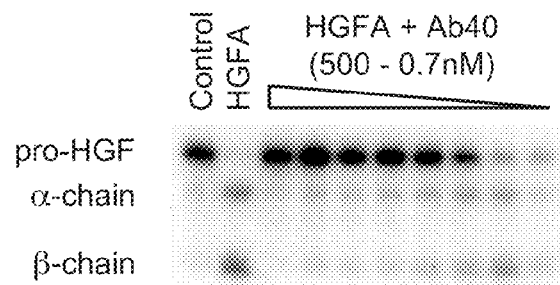
FIG. 2: Inhibition of HGFA enzymatic activity by Ab40. (a) Cleavage of $^{125}$I-pro-HGF by HGFA in presence of 3-fold serial dilutions of Ab40. The cleavage products HGF α- and β-chain were analyzed by SDS-PAGE (reducing conditions) and subsequently to X-ray film exposure. (b) Partial inhibition of chromogenic substrate, S-2266 hydrolysis (expressed as HGFA fractional activity $v_i/v_o$) by Ab40 and lack of inhibition by Ab40.ΔTrp. (c) Eadie-Hofstee plot of HGFA inhibition by Ab40 (1 µM-0.004 µM in 3-fold dilution steps; filled diamonds="no antibody" control) shows competitive inhibition ($V_{max}$=0.99 µM pNA/min and $K_m$=0.23 mM for control; $v_{max}^{app}$=0.99 µM pNA/min and $K_m^{app}$=0.82 mM for 1 µM Ab40).

(c) A close view of interactions of CDR-loops (L1-3, H1-3) of Fab40 with HGFA (surface representation). Critical residues involved in the interface interactions are highlighted and the 99-loop is indicated in red. Apart from several hydrogen bonds (dark grey dotted line), a single salt bridge between Asp241 of HGFA and Lys64H of Fab40 is observed.

FIG. 5: HGFA/Fab40 epitope and paratope, with HGFA (light grey) and Fab40 (light chain in light grey, heavy chain in dark grey) (a) Epitope of the Fab40 contact region (dark grey, 4 Å cutoff) on HGFA (light grey). The catalytic triad and the substrate binding subsites S1-S4 are indicated. (b) A different view of the Fab40 contact region on HGFA, which has a partial overlap with a region corresponding to exosite-II in thrombin (green) (c) The HGFA contact region on Fab40 (dotted lines, 4 Å cutoff). The heavy chain is involved in intimate contacts with HGFA and contributes to two-thirds of the total accessible surface area buried on HGFA upon Fab40 binding.

FIG. 6: The three structural snapshots of the 99-loop of HGFA. (a) The 'allosteric switch' in the conformation of the 99-loop leads to the formation of a deep hydrophobic pocket (colored in dark grey, residues Ala56, Pro90, Tyr88, Va196, Val105 and Ile107 of HGFA) allowing the binding of Trp96H of Fab40. (b) Size of the hydrophobic pocket (colored in dark grey) in HGFA/Fab40.ΔTrp is severely restricted due to movement of Va196 and other residues lining this pocket. (c) The 'relaxed' state conformation of the 99-loop of HGFA as found in other known structures (Shia et al., 2005; Wu et al., 2007). (d) Superposition of the 99-loop of HGFA (light grey and HGFA/Fab40 (dark grey) complex. Conformation transition of the 99-loop upon Fab40 binding, main chain of the 99-loop residues are shifted by >1 Å, while the side chain conformations are dislodged by >2.0. The CDR-H3 loop of Fab40 is highlighted in stick representation (upper). (e) Superposition of the 99-loop of HGFA/Fab40.ΔTrp with the 99-loop of HGFA and with the 99-loop of HGFA/Fab40. The conformation of the 99-loop (light grey) reverts almost back to 'relaxed' state in the Fab40.ΔTrp/HGFA complex structure. The CDR-H3 loop of Fab40.ΔTrp is highlighted in stick representation (dark grey). (f) Superposition of the 99-loop of HGFA/Fab40.ΔTrp with the 99-loop of HGFA/Fab40, indicating minor changes in CDR-H3 loop upon deletion of Trp96H of Fab40 (dotted circle).

FIG. 7: The allosteric mechanism. (a) Stereo view of the peptidic inhibitor Ac-KQLR-cmk ("KQLR" disclosed as SEQ ID NO: 10) (sticks embedded in CPK sphere representation in dark grey, lower) is covalently linked to active Ser195 and His57 of HGFA in the HGFA-KQLR/Fab40.ΔTrp complex ("KQLR" disclosed as SEQ ID NO: 10). The P2-Leu packs tightly against Pro99a of the 99-loop (sticks embedded in dots representation in light grey, upper) and a hydrogen bond with Ser99 stabilize the P4-Lys. (b) Stereo view of a model of HGFA-KQLR/Fab40 ("KQLR" disclosed as SEQ ID NO: 10) obtained by from the superposition of HGFA/Fab40 structure with HGFA-KQLR/Fab40.ΔTrp ("KQLR" disclosed as SEQ ID NO: 10) shows the allosteric inhibition is due to the steric clash between Pro99a and Ser99 with P2-Leu of the 99-loop (sticks embedded in dots representation in white). (c) Stereo view of the superposition of HGFA-KQLR/Fab40.ΔTrp ("KQLR" disclosed as SEQ ID NO: 10) with the model of HGFA-KQLR/Fab40 ("KQLR" disclosed as SEQ ID NO: 10) highlighting the critical conformational changes and disruption of hydrogen bond between Ser99 of HGFA and P4-Lys of the inhibitor.

Figure 8:
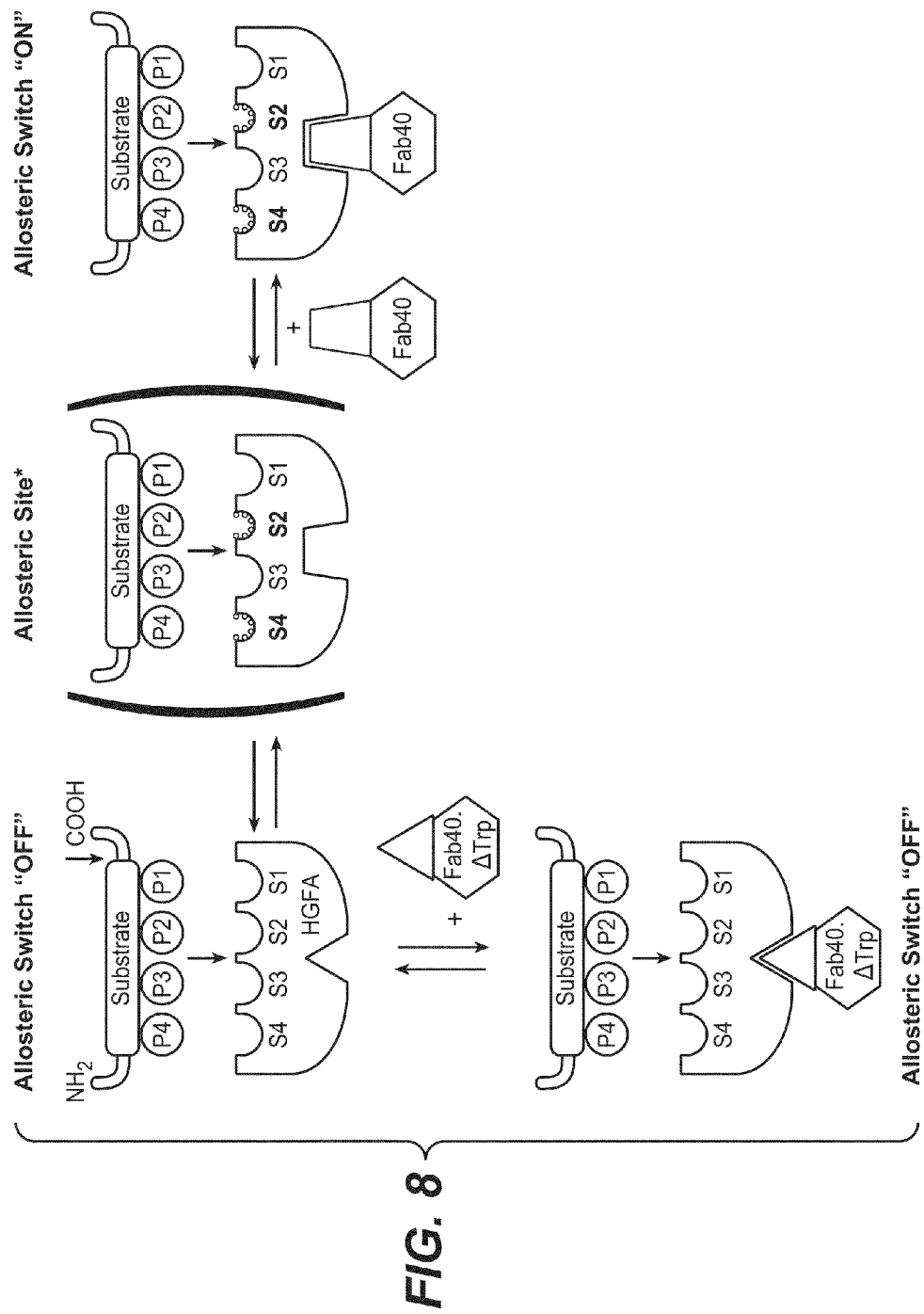

FIG. 8: A cartoon model illustrating the allosteric mechanism of inhibition. In the functionally active state, binding subsites are accessible to substrates and the 'allosteric switch' is in the "OFF" state. Fab40 preferentially samples one of the transiently formed conformations and shift the equilibrium away from the functionally active state thus driving the major population of enzyme molecules from the ' allosteric switch' "OFF" state to the "ON" state. In contrast, Fab40.ΔTrp which does inhibit enzyme activity might merely bind to the enzyme, without driving a change in state.

Figure 9A:
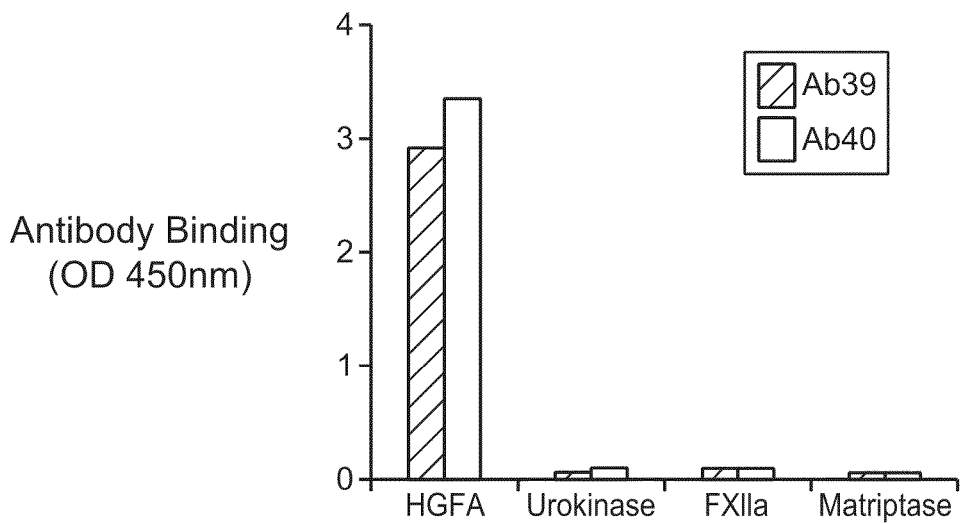

FIG. 9: (a) Antibody specificity. In a direct binding ELISA, 96-well plates were coated with 2 mg/ml of HGFA, matriptase (Kirchhofer et al. (2003) *J Biol Chem* 278:36341-36349), urokinase (American Diagnostica), or factor XIIa (American Diagnostica) and incubated with 10 mg/ml of anti-HGFA antibodies in PBS, 0.05% (v/v) Tween-20 (PBT) buffer. After washing, bound antibodies were detected by addition of anti-human antibody HRP conjugate (diluted 1:2, 500 in PBT buffer) and TMB substrate. Absorbance at 450 nm was measured on a microplate reader. (b) Eadie-Hofstee plot of HGFA inhibition by Ab39 (1 μM-0.004 μM in 3-fold dilution steps; filled diamonds="no antibody" control) shows competitive inhibition ($V_{max}$=0.99 μM pNA/min and $K_m$=0.25 mM for control; $V_{max}^{app}$=0.97 μM pNA/min and $K_m^{app}$=0.91 mM for 1 μM Ab39).

Figure 10:
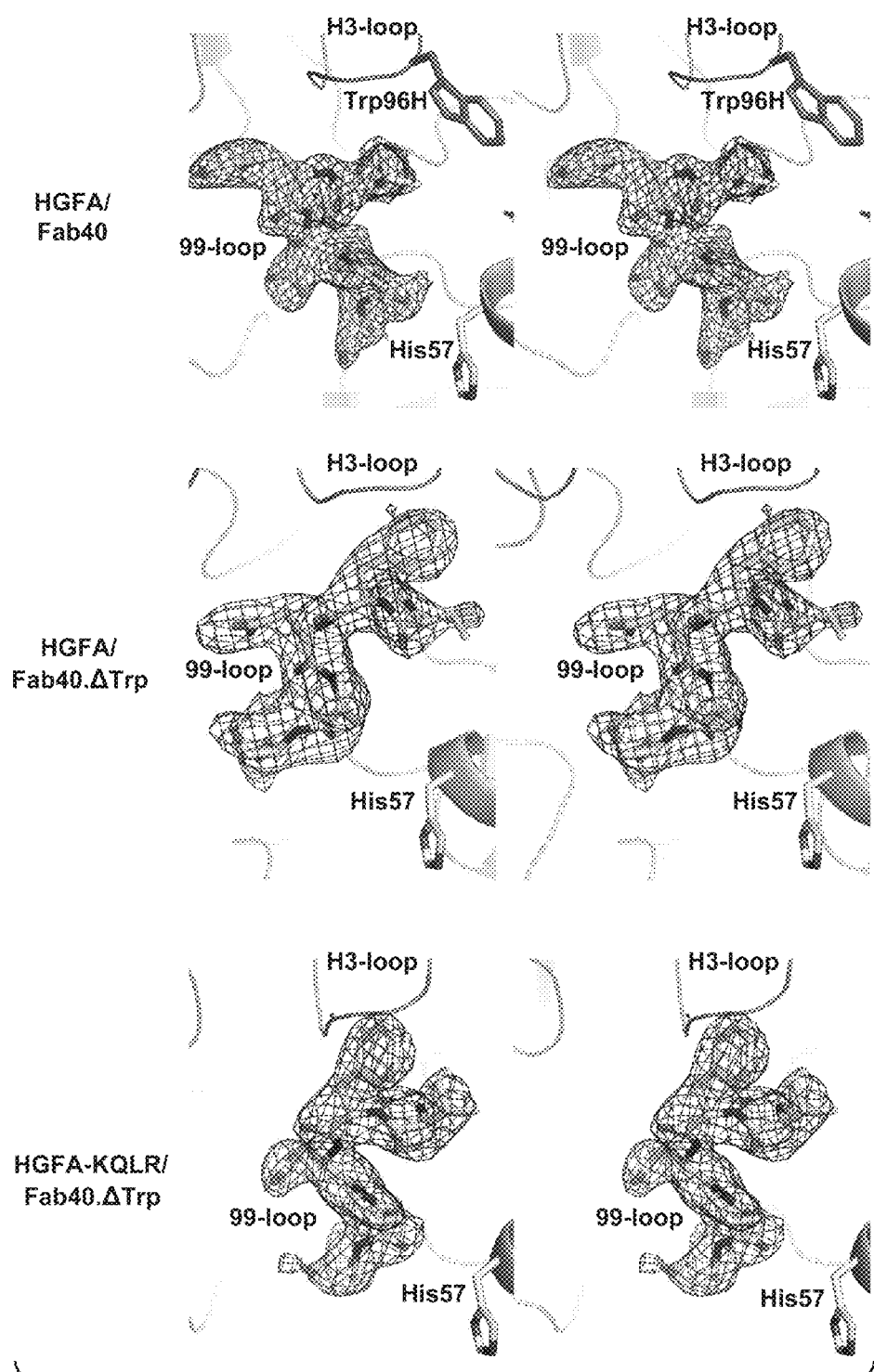

FIG. 10: Stereo images illustrating the quality of the electron density map (2fofc contoured at 1s). The 99-loop adopts a 'non-competent' conformation in HGFA/Fab40 structure. The 99-loop reverts to 'competent' conformation in HGFA/Fab40.ΔTrp structure. The covalently bound KQLR peptide (SEQ ID NO: 10) in the HGFA active site does not perturb the binding of Fab40ΔTrp as the 99-loop adopts a 'competent' conformation in the HGFA-KQLR/Fab40.ΔTrp ("KQLR" disclosed as SEQ ID NO: 10) structure.

Figure 11:
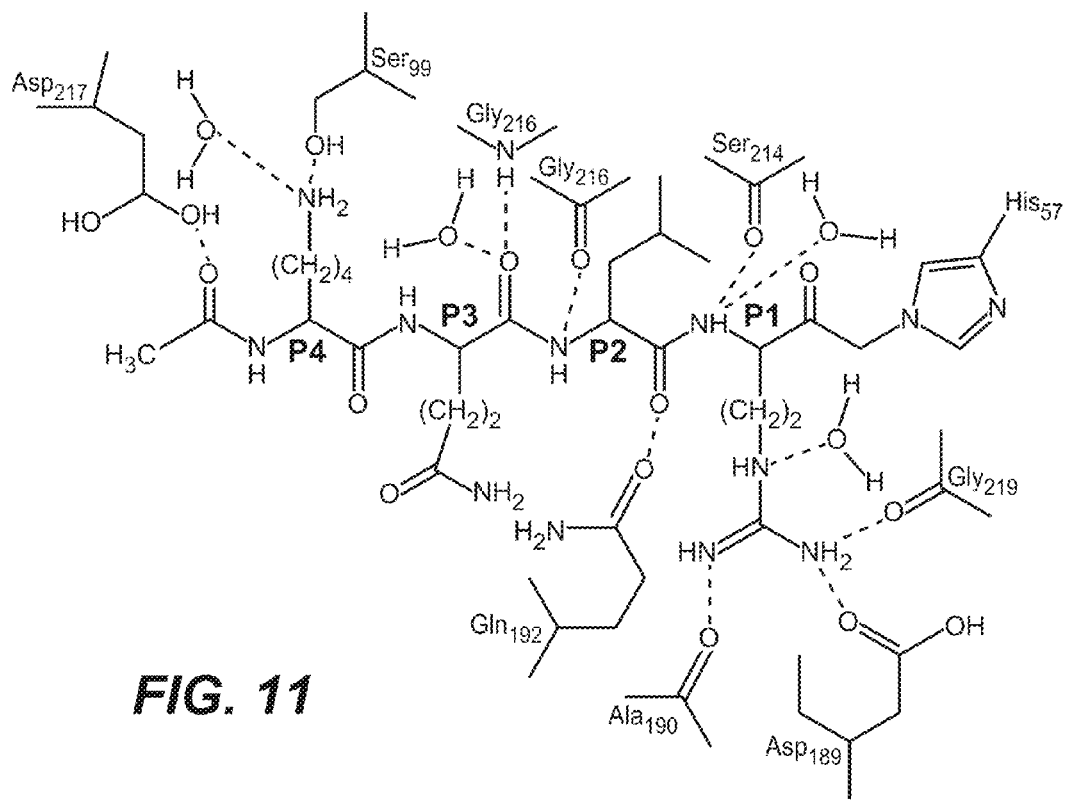

FIG. 11: Chemical structures and hydrogen bond networks at the active site in the HGFA-KQLR/Fab40.ΔTrp complex ("KQLR" disclosed as SEQ ID NO: 10) structure. Peptidic inhibitor KQLR (SEQ ID NO: 10) (center) is covalently bound to Ser195 and His57.

Figure 12:
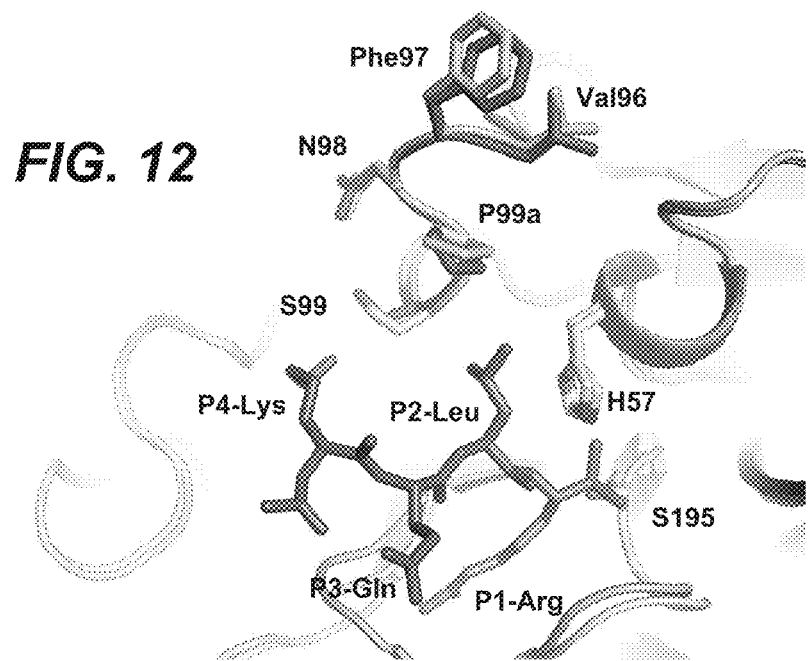

FIG. 12: Superposition of HGFA/Fab40.ΔTrp (light grey) and HGFA-KQLR/Fab40. ΔTrp ("KQLR" disclosed as SEQ ID NO: 10) (darker grey, KQLR (SEQ ID NO: 10)-darkest grey) complex structures. The conformation of the 99-loop is in 'competent' conformation as found in other known structures of HGFA.

Figure 13:
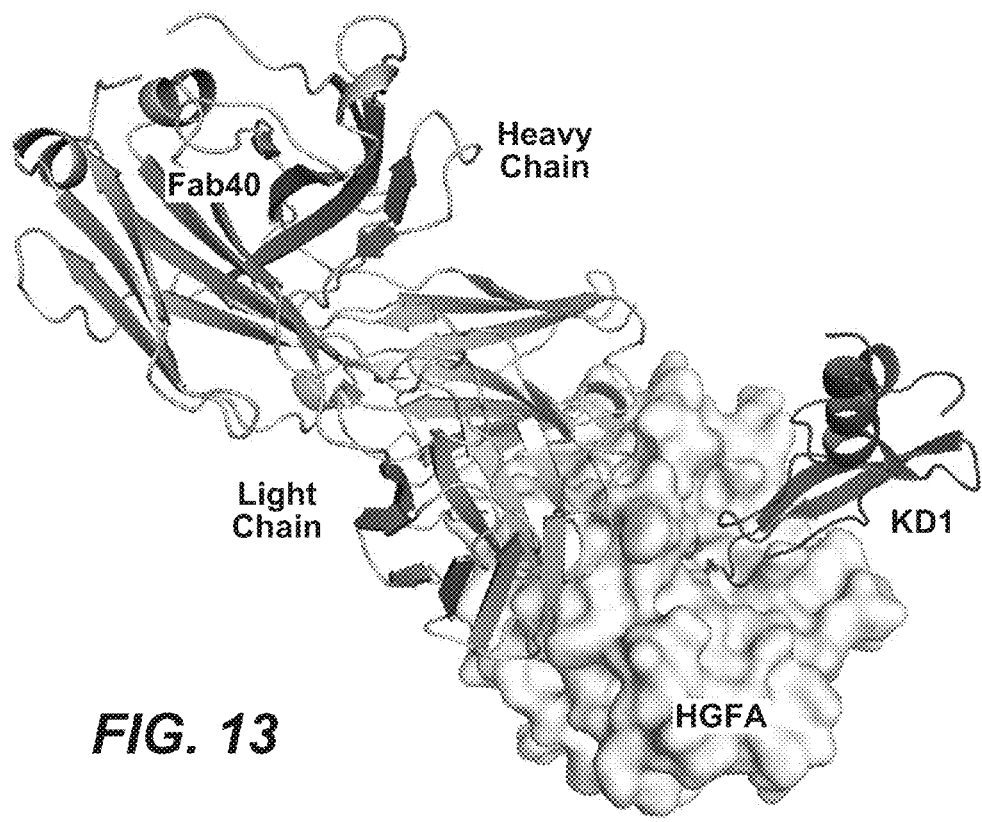

FIG. 13: Superposition of HGFA/Fab40 and HGFA/KD1 (Shia et al (2005) *J Mol Biol* 346(5): 1335-49) complex structures. The binding site of Fab40 (dark grey, ribbon) has no direct overlap with the binding site of KD1 (dark grey) but the movement of the 99-loop might cause some steric clash toward the binding of KD1 to HGFA/Fab40 complex.

Figure 14:
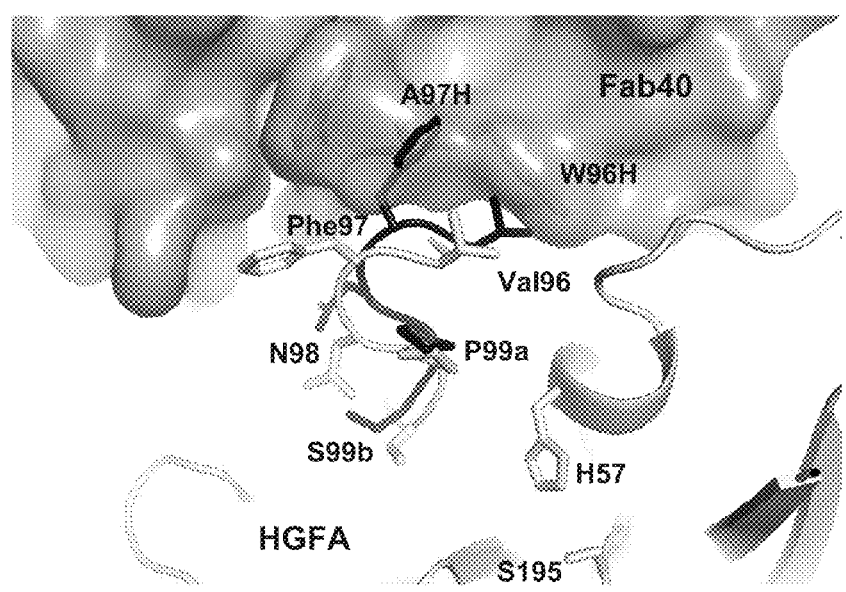

FIG. 14: Superposition of HGFA/Fab40 ('non-competent' conformation of 99-loop (interchangeably termed 'tense' conformation; light grey) complex and published HGFA ('competent' conformation (interchangeably termed 'relaxed' conformation) of 99-loop in black) structure. Steric clashes may occur between the 99-loop residues of HGFA in the 'competent' conformation with Trp96H, Ala97H and Trp98H in CDR-H3 loop residues of Fab40.

FIG. 15: Trypsin-like protease domains, aligned using structural homology. Native sequential residue numbering for HGFA appears above the sequences, and chymotrypsinogen numbering appears below the sequences. Chymotrypsinogen numbering includes insertions relative to the chymotrypsinogen sequence denoted with lower case letters (e.g. His60a) and deletions (e.g. there is no residue number 218, and so 217 is followed by 219). Residues 60a, 60b, 60c and 60d follow residue 60, and residues 111a, 111b, 111c and 111d follow residue 111, and residues 170a and 170b follow residue 170.

Figures 1, 15A:
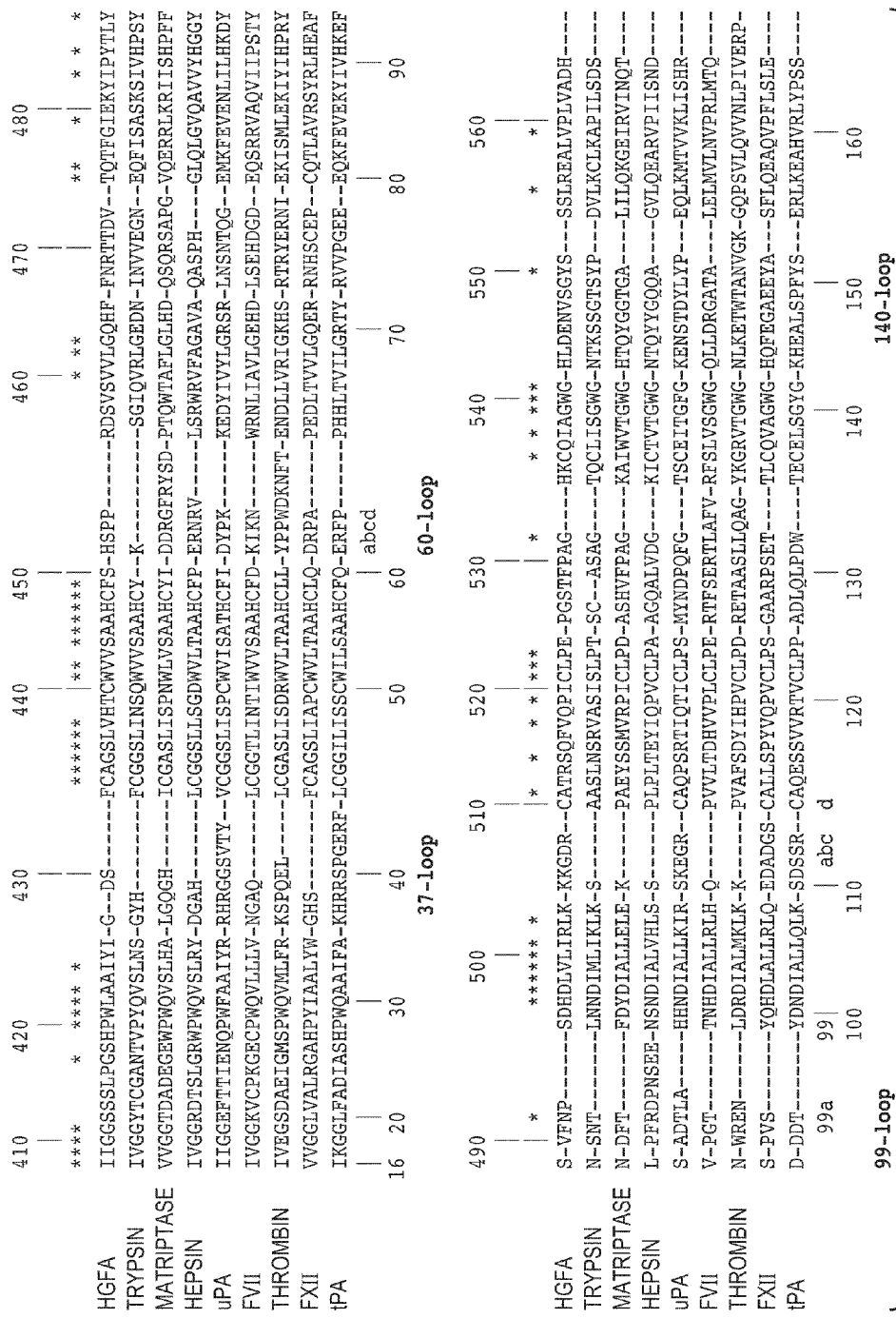
FIG. 1: CDR sequences of anti-HGFA antibodies. The residues are numbered according to the Kabat numbering system (Kabat et al., 1991). The sequence variations between Ab39 and Ab40 are shaded. A single residue deletion (Trp96H) of Fab40 is highlighted in bold.

But, residue 99a precedes residue 99, residue 184a precedes residue 184, residue 188a precedes residue 188, and residue 221a precedes residue 221. FIG. 15A discloses SEQ ID NOS 25-33, and FIG. 15B discloses SEQ ID NOS 34-41, all respectively, in order of appearance.

FIG. 16: A. Light chain variable domain sequences of anti-HGFA antibodies. B. Heavy chain variable domain sequences. The residues are numbered according to the Kabat numbering system and Kabat, Chothia and contact CDRs are diagrammatically depicted.

DETAILED DESCRIPTION OF THE INVENTION

The invention provides methods, compositions, kits and articles of manufacture comprising modulators of hepatocyte growth factor activator function, including methods of using such modulators.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

Definitions

The term "hepatocyte growth factor activator" or "HGFA", as used herein, refers, unless specifically or contextually indicated otherwise, to any native or variant (whether native or synthetic) HGFA polypeptide that is capable of binding to HGF and/or activating the HGF under conditions that permit such process to occur, for example, conditions that allow for the formation of the two chain form of HGF. The term "wild type HGFA sequence" generally refers to an amino acid sequence found in a naturally occurring HGFA and includes naturally occurring truncated or secreted forms, variant forms (e.g. alternatively spliced forms) and naturally occurring allelic variants. An example of a wild-type HGFA is a polypeptide comprising an amino acid sequence shown in Table 4 (SEQ ID NO: 19). The sequence numbering of HGFA is according to SWISS-PROT entry HGFA_HUMAN Accession No. Q04756 and as shown in Table 4. For residues within the protease domain, the alternate numbering scheme derived from chymotrypsinogen is sometimes used. For the interconversion of these two residue numbering schemes, refer to FIG. 15. Generally, throughout this application the numbering system utilized will be identified.

"Activated HGFA" or variations thereof, refers to any HGFA chain having one or more of the conformations that are adopted by wild type HGFA upon conversion of wild type HGFA protein from a single chain form to a 2 chain form. In some embodiments, the conversion results at least in part from cleavage between residue 407 and residue 408 of a HGFA protein. In some embodiments, the conformation refers specifically to the conformation of the protease domain. Activated HGFA may also be generated from fragments of full-length HGFA, such as the 34 kDa form. A 34 kDa form can be generated by cleavage between residues 372 and 373. The HGFA may be isolated from a variety of sources such as human tissue or human plasma or prepared by recombinant or synthetic methods. One embodiment of activated HGFA comprises an amino acid sequence shown in Table 5 (SEQ ID NO: 20). (Numbering is that of native HGFA as described herein.)

"HGFA variant" as used herein refers to polypeptide that has a different sequence than a reference polypeptide. In some embodiments, the reference polypeptide is a HGFA polypeptide comprising the sequence shown in Table 4. Variants include "non-naturally" occurring variants. In some embodiments, a variant has at least 80% amino acid sequence identity with the amino acid sequence shown in Table 4. The variants include those polypeptides that have substitutions, additions or deletions. In some embodiments, the variants have the biological activity of binding to the HGF and/or activating it. In other embodiments, the variant can bind to the HGF, but not activate it. Ordinarily, a HGFA variant polypeptide will have at least 80% sequence identity, more preferably will have at least 81% sequence identity, more preferably will have at least 82% sequence identity, more preferably will have at least 83% sequence identity, more preferably will have at least 84% sequence identity; more preferably will have at least 85% sequence identity, more preferably will have at least 86% sequence identity, more preferably will have at least 87% sequence identity, more preferably will have at least 88% sequence identity, more preferably will have at least 89% sequence identity, more preferably will have at least 90% sequence identity, more preferably will have at least 91% sequence identity, more preferably will have at least 92% sequence identity, more preferably will have at least 93% sequence identity, more preferably will have at least 94% sequence identity, more preferably will have at least 95% sequence identity, more preferably will have at least 96% sequence identity, more preferably will have at least 96% sequence identity, more preferably will have at least 97% sequence identity, more preferably will have at least 98% sequence identity, more preferably will have at least 99% sequence identity with a HGFA polypeptide comprising an amino acid sequence comprising the sequence shown in Table 4 or HGFA polypeptide comprising the sequence shown in Table 5.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. Unless indicated otherwise, numbering of all amino acid positions herein is according to the Kabat numbering system.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy chain subgroup III of Kabat et al. In one embodiment, the VH subgroup III consensus framework amino acid sequence comprises at least a portion or all of each of the following sequences:

| | |
|---|---|
| EVQLVESGGGLVQPGGSLRLSCAAS- | (SEQ ID NO: 11) |
| H1-WVRQAPGKGLEWV- | (SEQ ID NO: 12) |
| H2-RFTISRDNSKNTLYLQMNSLRAEDTAVYYC- | (SEQ ID NO: 13) |
| H3-WGQGTLVTVSS. | (SEQ ID NO: 14) |

A "VL subgroup I consensus framework" comprises the consensus sequence obtained from the amino acid sequences in variable light kappa subgroup I of Kabat et al. In one embodiment, the VL subgroup I consensus framework amino acid sequence comprises at least a portion or all of each of the following sequences:

| | |
|---|---|
| DIQMTQSPSSLSASVGDRVTITC- | (SEQ ID NO: 15) |
| L1-WYQQKPGKAPKLLIY- | (SEQ ID NO: 16) |
| L2-GVPSRFSGSGSGTDFTLTISSLQPEDFATYYC- | (SEQ ID NO: 17) |
| L3-FGQGTKVEIK. | (SEQ ID NO: 18) |

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

Dysregulation of angiogenesis can lead to many disorders that can be treated by compositions and methods of the invention. These disorders include both non-neoplastic and neoplastic conditions. Neoplastics include but are not limited to those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertrophic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromefihylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl) benzenesulfonamide; and pharmaceutically acceptable salts, acids or derivatives of any of the above.

A "growth inhibitory agent" when used herein refers to a compound or composition which inhibits growth of a cell whose growth is dependent upon HGF/c-met activation either in vitro or in vivo. Thus, the growth inhibitory agent may be one which significantly reduces the percentage of HGF/c-met-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

Generating Antibodies Using Prokaryotic Host Cells:
Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB⁻ strains) provide cytoplasm conditions that are favorable for disulfide bond formation, thereby permitting proper folding and assembly of expressed protein subunits. Proba and Pluckthun Gene, 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ (nmpc-fepE) degP41 kan$^R$ (U.S. Pat. No. 5,639,635). Other strains and derivatives thereof, such as E. coli 294 (ATCC 31,446), E. coli B, E. coli$_\lambda$1776 (ATCC 31,537) and E. coli RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, for e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Activity Assays

The antibodies of the present invention can be characterized for their physical/chemical properties and biological functions by various assays known in the art.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, for e.g. as described in Gazzano-Santoro et al., J. Immunol. Methods 202:163 (1996), may be performed. FcRn binding and in vivo clearance/half life determinations can also be performed using methods known in the art.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

In one aspect, the invention provides antibody comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, for e.g., as described in U.S. Pat. No. 5,731,168.

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, for e.g. in the Fc region. These antibodies would nonetheless retain substantially the same characteristics required for therapeutic utility as compared to their wild type counterpart. For e.g., it is thought that certain alterations can be made in the Fc region that would result in altered (i.e., either improved or diminished) C1q binding and/or Complement Dependent Cytotoxicity (CDC), for e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants.

Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5739116; 5767285; 5773001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623

(1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-Maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., Cancer Research 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab-(L-D)_p \quad (I)$$

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations comprising an antibody of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In certain embodiments, an immunoconjugate comprising an antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, for e.g. by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. One typical daily dosage might range from about 1 µg/kg to 100 mg/kg or more, depending on the factors mentioned above, whether, for example, by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, for e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Materials and Methods

Antibody phage display: Synthetic antibody libraries displayed bivalent Fab fragments on the M13 phage and the diversity was generated by use of oligo-directed mutagenesis in three CDRs of the heavy chain. The details of the Fab libraries were described previously (Lee et al, 2004a; Lee et al, 2004b). Nunc 96-well Maxisorp immunoplates were coated overnight at 4° C. with HGFA (10 µg/ml) and then blocked for 1 hour at room temperature with phage blocking buffer PBST (PBS, 1% (w/v) BSA, 0.05% (v/v) Tween 20). The antibody phage libraries were added to the HGFA-coated plates and incubated overnight at room temperature. The plates were washed with PBT (PBS, 0.05% (v/v) Tween-20) buffer and bound phage were eluted with 50 mM HCl-500 mM NaCl for 30 min and neutralized with an equal volume of 1 M Tris-HCl, pH 7.5. Recovered phage was amplified in *E. coli* XL-1 blue cells. During subsequent selection rounds, incubation of antibody phage with the antigen-coated plates was reduced to 2-3 hours and the stringency of plate washing was gradually increased.

Affinity maturation of Ab39: Ab39 was affinity-matured by the use of monovalent Fab instead of bivalent Fab to reduce potential avidity effects during selection. To improve the efficiency of affinity maturation, stop codons were introduced to CDR-L3. Three different CDR combinatorial libraries, L1/L2/L3, L3/H1/H2 and L3/H3 were targeted for randomization using a "soft randomization" strategy that maintains a wild-type sequence bias such that selected positions are mutated only 50% of the time (Liang et al., 2007). For selecting affinity-matured clones, phage libraries were subjected to plate sorting for the first round and followed by four rounds of solution phase sorting as described before (Liang et al., 2007). Increased stringency was used during four rounds of solution phase sorting by decreasing the amount of biotinylated HGFA. Excess amounts of unlabelled HGFA (500~2000-fold) were added into the last two rounds of selections to compete off the fast off-rate binders. Off-rate selection strategies were used since Ab39 has a relatively high association rate constant ($k_{on}$) but a relatively fast dissociation rate constant ($k_{off}$) (Table 1). The anti-HGFA Fabs were subsequently reformatted to IgGs.

Antibody reformatting and determination of dissociation rate constants to HGFA: Anti-HGFA Fabs were reformatted into human IgG1 by cloning the $V_L$ and $V_H$ regions of individual clones into LPG3 and LPG4 vector, respectively (Liang et al, 2007). The full-length antibodies were transiently expressed in Chinese Hamster Ovary cells and purified on a protein-A column. To determine binding affinities of the reformatted anti-HGFA antibodies, surface plasmon resonance measurements on a BIAcore™-3000 instrument (GE Health Care, NJ) were performed. Rabbit anti-human IgG were chemically immobilized (amine coupling) on CM5 biosensor chips and the anti-HGFA antibodies were captured to give approximately 250 response units (RU). For kinetics measurements, two-fold serial dilutions of HGFA or active site-blocked HGFA (0.9 nM to 250 nM) were injected in PBT buffer at 25° C. with a flow rate of 30 µl/min. HGFA-KQLR ("KQLR" disclosed as SEQ ID NO: 10) was produced by incubating HGFA with two fold molar excess of Ac-KQLR-cmk ("KQLR" disclosed as SEQ ID NO: 10) for 2 hours at room temperature, followed by size exclusion chromatography to remove non-incorporated Ac-KQLR-cmk ("KQLR" disclosed as SEQ ID NO: 10). Association rates ($k_{on}$) and dissociation rates ($k_{off}$) were obtained by using a simple one-to-one Langmuir binding model (BIAEvaluation) and the equilibrium dissociation constants ($K_D$) were calculated ($k_{off}/k_{on}$). Longer injection (5 min) of 2-fold serial dilution of HGFA or HGFA-KQLR ("KQLR" disclosed as SEQ ID NO: 10) (1.5 nM to 3000 nM) over captured antibody (Ab40.ΔTrp) sensor chip was implemented to achieve maximal binding ($R_{max}$) and reach the steady state. The values of $R_{eq}$ (20-80% of $R_{max}$) were calculated and plotted individually against C (concentration of HGFA or HGFA-KQLR ("KQLR" disclosed as SEQ ID NO: 10)) using BIAEvaluation Software to determine KD at the steady state analysis.

HGFA purification, enzymatic kinetic assays and competition ELISA: HGFA (Val373-Ser655) was produced by use of a baculovirus—insect cell expression system and purified on a Ni-NTA-agarose column, followed by size exclusion chromatography as described (Kirchhofer et al, 2003). Pro-HGF activation assays with active site-titrated HGFA were carried out essentially as described (Kirchhofer et al., 2003) using serial dilutions of antibody incubated with 1 nM HGFA and 25 µg/ml of $^{125}$I-pro-HGF. For chromogenic substrate assays with Chromogenix S-2266 (H-D-Valyl-L-leucyl-L-arginine-paranitroanilide) (Diapharma, Westchester, Ohio), 5 nM HGFA was incubated for 40 min in 96-well plates with increasing concentrations of antibodies in TNCT buffer (20 mM Tris, pH 8.0, 150 mM NaCl, 5 mM $CaCl_2$, 0.01%-Triton X-100). After addition of S-2266 (0.24 mM~$K_m$) the linear rates of the increase in absorbance at 405 nm were measured on a kinetic microplate reader (Spectramax-M5, Molecular devices, Sunnyvale, Calif.). Enzyme kinetic measurements for Ab39 and Ab40 were carried out with 3 nM HGFA incubated with various antibody concentration (1 µM-0.004 µM in 3-fold dilutions) in TNCT buffer for 40 min. Various concentrations of Chromogenix S-2266 were added and the linear rates of absorbance increase at 405 nm were measured. Eadie-Hofstee plots of the data obtained (v versus v/[S]) were indicative of a competitive inhibition mechanism. Competition ELISA experiments were performed to evaluate effect of Ab40 on KD1 binding to HGFA. 96-well Maxisorp plate coated with HGFA (1 µg/ml) were incubated with increasing concentrations of Ab40 in PBST buffer for 2 hours, followed by addition of 1 nM biotinylated KD1 for 15 minutes. Biotinylated KD1 that was bound to HGFA was detected by streptavidin-HRP conjugates.

Competition HGFA binding ELISA experiments: For binding specificity measurements, 96-well Maxisorp plates were coated with 2 µg/ml of HGFA, matriptase, urokinase-type plasminogen activator or factor XIIa and incubated with 10 µg/ml of anti-HGFA IgG in PBST buffer for at least 1 hour at room temperature. The plates were washed with PBT buffer and bound antibodies were detected with anti-human antibody HRP conjugate diluted 1:2500 in PBST buffer, developed with TMB substrate for approximately 5 minutes, quenched with 1 M $H_3PO_4$, and absorbance was measured on a microplate reader at 450 nm.

Crystallography: Fab40 and Fab40.ΔTrp was expressed in *E. coli* and purified by using protein-G sepharose followed by cation exchange chromatography. Fab40 and Fab40.ΔTrp comprise the heavy and light chain variable regions depicted in FIG. 1. Complexes between (a) HGFA protease domain (Table 6) and Fab40 (b) HGFA protease domain (Table 6) and Fab40.ΔTrp or (c) HGFA protease domain (Table 6)-KQLR (SEQ ID NO: 10) and Fab40.ΔTrp were formed by mixing in a 1:2 molar ratio and purified by size exclusion chromatography (Superdex 200). The complexes were concentrated to 10 mg/ml in 10 mM HEPES pH 7.2, 150 mM NaCl. HGFA/Fab40 and HGFA-KQLR/Fab40.ΔTrp complexes ("KQLR" disclosed as SEQ ID NO: 10) yielded crystals under 14% PEG 10,000, 100 mM HEPES pH 7.2, while HGFA/Fab40.ΔTrp yielded crystals under 10% PEG 10,000, 100 mM HEPES pH 7.5. For X-ray data collection, the crystals were transferred to 14% PEG 10,000, 100 mM HEPES pH 7.2, 20% glycerol and immersed in liquid nitrogen. X-ray data were collected at 100 K, either at beam line 9-2 at SSRL/SLAC(HGFA/Fab40) or at ALS beamline 5.0.2 (HGFA/Fab40.ΔTrp and HGFA-KQLR/Fab40.ΔTrp ("KQLR" disclosed as SEQ ID NO: 10)) and reduced using HKL2000 (Otwinowski and Minor, 1997). The structure was solved by molecular replacement using PHASER (McCoy et al, 2005) and refined using CNX (Accelrys) together with elements of the CCP4 suite (CCP4, 1994)(CCP4, 1994). Data reduction and model refinement statistics appear in Table 2. Molecular graphics figures were prepared using PyMOL (DeLano, W. L. The PyMOL Molecular Graphics System, 2002). Coordinates for the three complexes are shown in co-pending co-owned U.S. provisional patent application No. 61/253,014, filed Oct. 19, 2009 and in the RCSB Protein Data Bank with access codes 3K2U, 2WUB, and 2WUC (the contents of which are incorporate by reference in its entirety).

TABLE 1

Antibody binding to HGFA ("KQLR" disclosed as SEQ ID NO: 10)

| | HGFA | | | HGFA-KQLR complex | | |
|---|---|---|---|---|---|---|
| | $k_{on}$ ($\times 10^5 M^{-1} s^{-1}$) | $k_{off}$ ($\times 10^{-4} s^{-1}$) | $K_D$ (nM) | $k_{on}$ ($\times 10^5 M^{-1} s^{-1}$) | $k_{off}$ ($\times 10^{-4} s^{-1}$) | $K_D$ (nM) |
| Ab39 | 5.2 ± 0.5 | 53.0 ± 2.0 | 10.3 ± 1.3 | n.d. | n.d. | n.d. |
| Ab40 | 10.8 ± 0.46 | 1.75 ± 0.08 | 0.16 ± 0.01 | 3.2 ± 0.14 | 4.3 ± 0.13 | 1.35 ± 0.1 |
| $^a$Ab40.ΔTrp | — | — | 150 ± 9.1 | — | — | 161 ± 7.6 | n.d. not determined $^a$the $K_D$ values were determined using steady state affinity measurements Generally throughout this application, IgG form of antibody is designated with prefix Ab and Fab form is designated with prefix Fab. Generally, the amino acids of Fab are indicated with a letter-code followed by the residue number, followed by H for heavy chain and L for light chain

TABLE 2

Data Collection and Refinement ("KQLR" disclosed as SEQ ID NO: 10)

| | HGFA/Fab40 | HGFA/Fab40.ΔTrp | HGFA-KQLR/Fab40.ΔTrp |
|---|---|---|---|
| Data collection | | | |
| Space group | P1 | P2₁ | C222₁ |
| Cell dimensions | | | |
| a, b, c (Å) | a = 38.94, b = 48.93, c = 96.03 | a = 72.36, b = 89.53, c = 118.47 | a = 80.36, b = 147.89, c = 146.37 |
| α, β, γ (°) | α = 98.10, β = 95.01, γ = 103.89 | β = 91.08 | |
| Resolution (Å) | 50-2.35 (2.43-2.35) | 50-2.90 (3.00-2.90) | 50-2.70 (2.8-2.7) |
| Rsym$^{a,b}$ | 0.050 (0.198) | 0.094 (0.505) | 0.143 (0.652) |
| I/σI$^b$ | 15 (2.9) | 14.0 (2.7) | 15 (2.9) |
| Completeness (%)$^b$ | 94.9 (86.9) | 98.8 (98.3) | 99.4 (97.3) |
| Redundancy | 2.0 (1.9) | 3.7 (3.6) | 7.3 (7.4) |
| Refinement | | | |
| Resolution (Å) | 20-2.35 | 20-2.90 | 20-2.70 |
| No. of reflections | 25746 | 32630 | 23158 |
| Final R$^c$, R$_{FREE}$ | 0.237, 0.291 | 0.216, 0.275 | 0.227, 0.278 |
| No. of atoms | | | |
| Protein | 5046 | 9927 | 5138 |
| Ligand | 28 | 56 | 68 |
| Water | 168 | 153 | 133 |
| B-factors (average) | | | |
| Protein | 65.27 | 68.92 | 35.86 |
| Ligand | 91.72 | 138.26 | 76.06 |
| Water | 58.37 | 39.42 | 29.65 |
| R.m.s. deviations | | | |
| Bond lengths (Å) | 0.008 | 0.008 | 0.007 |
| Bond angles (°) | 1.330 | 1.231 | 1.420 |

$^a$Rsym = Σ||I| − |<I>||/Σ|<I>|, where I is the intensity of a single observation and <I> is the average intensity for symmetry equivalent observations.
$^b$In parenthesis, for the highest resolution shell.
$^c$R = Σ|Fo − Fc|/Σ|Fo|, where Fo and Fc are observed and calculated structure factor amplitudes, respectively.

TABLE 3

Contact distances between HGFA and Fab residues ("KQLR" disclosed as SEQ ID NO: 10)

| | | | Contact distance (Å) | | |
|---|---|---|---|---|---|
| # | Fab residue | HGFA residue | HGFA/Fab40 | HGFA/Fab40 · ΔTrp | HGFA-KQLR/Fab40 · ΔTrp |
| 1 | H:Tyr 52 [OH] | Phe 59 [O] | 3.3 | 3.4 | >3.5 |
| 2 | H:Tyr 52 [OH] | Ser 60b [Oγ] | 2.6 | 3.0 | 2.5 |
| 3 | H:Tyr 58 [OH] | Pro 90 [O] | 2.7 | 2.6 | 2.7 |
| 4 | H:Tyr 33 [OH] | Tyr 91 [O] | 2.6 | >3.5 | >3.5 |
| 5 | H:Trp 95 [Nε1] | Tyr 94 [O] | 3.0 | 2.7 | 2.9 |
| 6 | H:Lys 64 [Nζ] | Asp 240 [Oδ2] | 3.4 | >3.5 | >3.5 |
| 7 | H:Ala 53 [O] | Arg 61 [Nε] | 3.5 | 3.2 | 3.1 |
| 8 | H:Gly 54 [O] | Tyr 88 [N] | 3.1 | 2.9 | 3.0 |
| 9 | H:Gly 55 [O] | Lys 87 [Nζ] | 2.9 | 2.9 | 2.9 |
| 10 | H:Thr 57 [O] | Arg 241 [Nω'] | 2.5 | 2.3 | 2.3 |
| 11 | H:Trp 96 [O] | Ser 95 [Oγ] | 3.0 | >3.5 | >3.5 |
| 12 | H:Trp 96 [O] | Val 96 [N] | 3.2 | >3.5 | >3.5 |

TABLE 3-continued

Contact distances between HGFA and Fab residues ("KQLR" disclosed as SEQ ID NO: 10)

| # | Fab residue | HGFA residue | HGFA/Fab40 | HGFA/ Fab40 · ΔTrp | HGFA-KQLR/ Fab40 · ΔTrp |
|---|---|---|---|---|---|
| 13 | H:Gly 31 [O] | Ser 60b [Oγ] | >3.5 | 3.5 | >3.5 |
| 14 | H:Pro 52a [O] | Arg 61 [Nω'] | >3.5 | 3.5 | 3.5 |
| 15 | H:Ala 97 [O] | Ser 95 [Oγ] | >3.5 | >3.5 | 2.6 |
| 16 | H:Ala 97 [O] | Phe 97 [N] | >3.5 | >3.5 | 3.4 |
| 17 | H:Ala 97 [O] | Val 96 [N] | >3.5 | >3.5 | 3.5 |
| 18 | L:Arg 93 [Nω] | Asn 179 [Oδ1] | 2.7 | >3.5 | >3.5 |
| 19 | L:Arg 93 [Nω'] | Asn 179 [Oδ1] | 2.7 | >3.5 | >3.5 |
| 20 | L:Ala 94 [N] | Tyr 91 [OH] | 2.9 | 2.6 | 2.9 |
| 21 | L:Ser 91 [O] | His 101 [Nε2] | 3.0 | 3.0 | 3.0 |
| 22 | L:Asn 92 [Oδ1] | Asn 179 [Nδ2] | 3.0 | 3.1 | 3.2 |
| 23 | L:Arg 93 [Nω] | Asn 233 [O] | >3.5 | >3.5 | 3.5 |
| 24 | L:Arg 93 [Nω'] | Asp 236 [Oδ2] | >3.5 | >3.5 | 3.3 |

TABLE 4

HGFA (SEQ ID NO: 19)

```
MGRWAWVPSP WPPPGLGPFL LLLLLLLLLP RGFQPQPGGN
RTESPEPNAT ATPAIPTILV TSVTSETPAT SAPEAEGPQS
GGLPPPPRAV PSSSSPQAQA LTEDGRPCRF PFRYGGRMLH
ACTSEGSAHR KWCATTHNYD RDRAWGYCVE ATPPPGGPAA
LDPCASGPCL GSCSNTQD PQSYHCSCPR AFTGKDCGTE
KCFDETRYEY LEGGDRWARV RQGHVEQCEC GRTWCEGT
RHTACLSSPC LNGGTCHLIV ATGTTVCACP PGFAGRLCNI
EPDERCFLGN GTGYRGVAST SASGLSCLAW NSDLLYQELH
VDSVGAAALL GLGPHAYCRN PDNDERPWCY VKDSALSWE
YCRLEACESL TRVQLSPDLL ATLPEPASPG RQACGRRHKK
RTFLRPRIIG GSSSLPGSHP WLAAIYIGDS FCAGSLVHTC
WVVSAAHCFS HSPPRDSVSV VLGQHFFNRT TDVTQTFGIE
KYIPYTLYSV FNPSDHDLVL IRLKKKGDRC ATRSQFVQPI
CLPEPGSTFP AGHKCQIAGW GHLDENVSGY SSSLREALVP
LVADHKCSSP EVYGADISPN MLCAGYFDCK SDACQGDSGG
PLACEKNGVA YLYGIISWGD GCGRLHKPGV YTRVANYVDW
INDRIRPPRR LVAPS
```

TABLE 5

Activated HGFA (SEQ ID NO: 20)

```
373  vqlspdll atlpepaspg rqacgrrhkk rtflrpriig
     gssslpgshpwlaaiyigds fcagslvhtc wvvsaahcfs
     hspprdsysv vlgqhffnrt tdvtqtfgiekyipytlysv
     fnpsdhdlvl irlkkkgdrc atrsqfvqpi clpepgstfp
     aghkcqiagwghldenvsgy ssslrealvp lvadhkcssp
     evygadispn mlcagyfdck sdacqgdsggplacekngva
     ylygiiswgd gcgrlhkpgv ytrvanyvdw indrirpprr
     lvaps
```

TABLE 6

HGFA serine protease domain (SEQ ID NO: 21)

```
IIGGSSSLPGSHPWLAAIYIGDSFCAGSLVHTCWVVSAAHCFSHSPPR
DSVSVVLGQHFFNRTTDVTQTFGIEKYIPYTLYSVFNPSDHDLVLIRL
KKKGDRCATRSQFVQPICLPEPGSTFPAGHKCQIAGWGHLDENVSGYS
SSLREALVPLVADHKCSSPEVYGADISPNMLCAGYFDCKSDACQGDSG
GPLACEKNGVAYLYGIISWGDGCGRLHKPGVYTRVANYVDWINDRIR
```

Results

Generation of Anti-HGFA Phage Antibody

Ab39 was identified by screening of a synthetic F(ab)$_2$ phage display library (Wu et al, 2000). Ab39 was subsequently affinity-matured as described in the methods. The improvement in binding affinity as measured by surface plasmon resonance experiments was 64-fold (Table 1), due to four changes in the sequence of CDR-L3(FIG. 1). The binding specificities of both Ab39 and Ab40 were assessed by using an ELISA to measure binding to structurally related proteases, including the closest homologues factor XIIa and urokinase (Miyazawa et al., 1993). The results demonstrated a complete lack of binding to factor XIIa, urokinase and matriptase, suggesting good specificity (FIG. 9).

Enzyme kinetics and effect of active-site occupancy by Ab40 binding

Ab40 inhibited the cleavage of pro-HGF into the α/β-heterodimer mediated by HGFA (FIG. 2a) with a potency that agreed with its binding affinity (Table 1). The inhibitory effects of Ab40 and Ab39 were also assessed in enzymatic assays using the synthetic para-nitroanilide substrate Chromogenix S-2266 (H-D-Val-Leu-Arg-pNA). The enzymatic activity of HGFA was only partially inhibited by Ab40 (FIG.

Figure 2B:
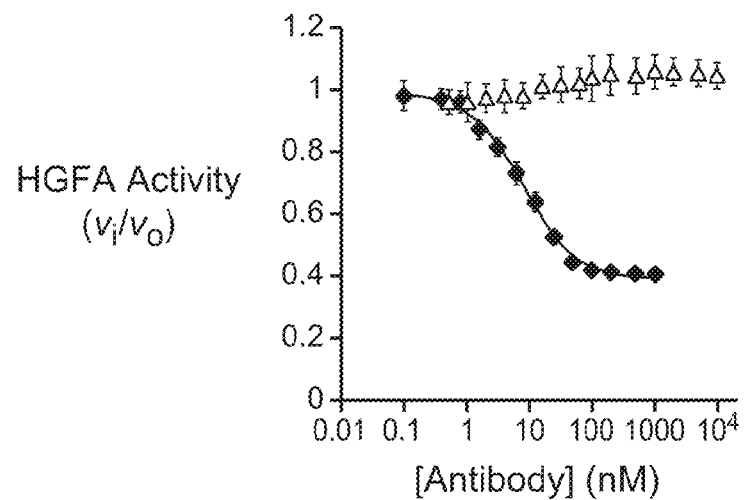
Figure 2C:
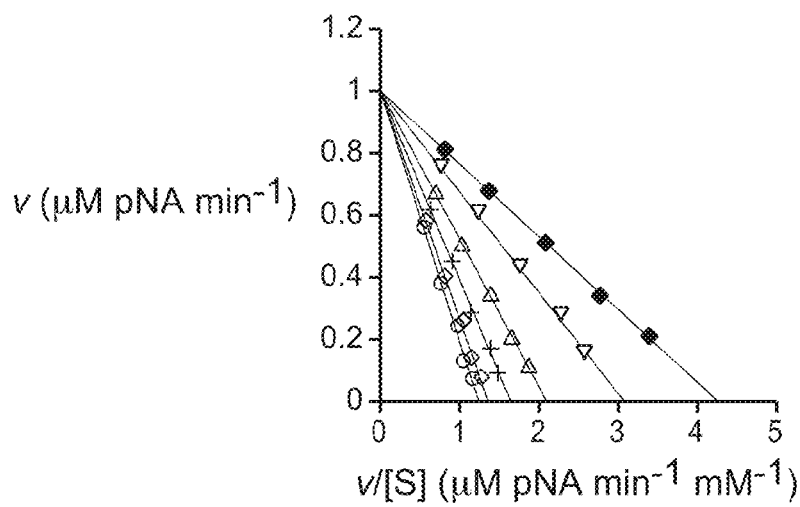
Figure 9B:
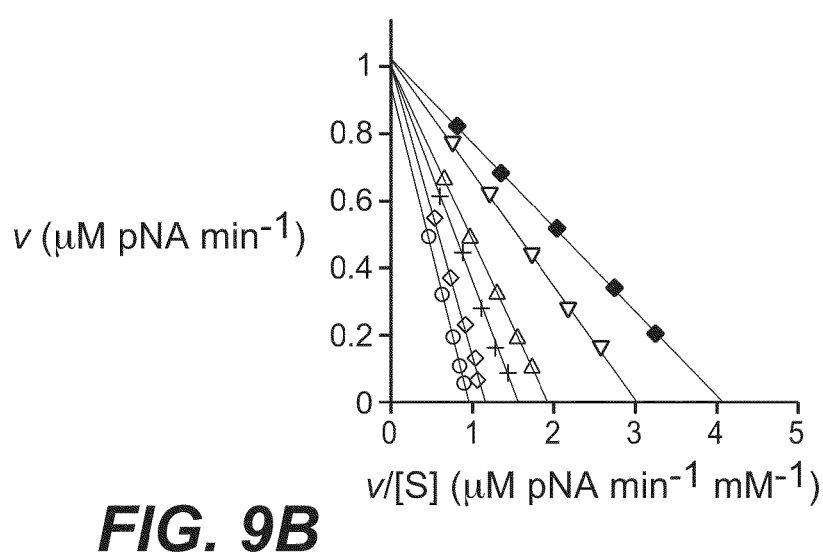

2b), with a maximum inhibition of about 60% under the chosen experimental conditions. Eadie—Hofstee plots demonstrated that the inhibition mechanism was competitive since Ab40 (and Ab39) increased the $K_m^{app}$ but not $V_{max}^{app}$ values (FIG. 2c, 9b). In accordance with partial inhibition, the slopes ($-Kr_m^{app}$) approached a finite limit at high Ab40 concentration. Similar results were obtained with the parental Ab39 (data not shown), demonstrating that Ab39 and Ab40 were partial competitive inhibitors of HGFA. To analyze the influence of active site occupancy on the antibody binding, we measured antibody binding to HGFA in the presence of small molecule and macromolecular inhibitors. Benzamidine, which only binds in the S1 pocket of trypsin-like serine proteases, did not interfere with binding of Ab40 to HGFA (data not shown). A peptidic inhibitor matching the pro-HGF cleavage sequence coupled to a war-head group (Ac-KQLR-cmk ("KQLR" disclosed as SEQ ID NO: 10)) was used to covalently modify HGFA in the active site, where it occupied the S4-S1 subsites. Surface plasmon resonance studies with HGFA-KQLR complex ("KQLR" disclosed as SEQ ID NO: 10) showed that the irreversibly bound peptidic inhibitor interfered with the binding of Ab40 (FIG. 3a-b). An 8-fold decrease in affinity of Ab40 binding to HGFA-KQLR complex ("KQLR" disclosed as SEQ ID NO: 10) compared to HGFA was observed (Table 1). The Kunitz domain inhibitor KD1, which interacts with the extended active-site region (Shia et al, 2005), also interfered with Ab40 binding in surface plasmon resonance experiments (FIG. 3c). In agreement, a competition ELISA showed moderate inhibition of KD1 binding to HGFA by Ab40 (FIG. 3d). In summary, binding of Ab40 to HGFA was influenced by inhibitor occupancy at extended subsites, including S2-S4 but not S1.

Structure of the HGFA/Fab40 Complex Reveals the 'Allosteric Switch'

Figure 4A:
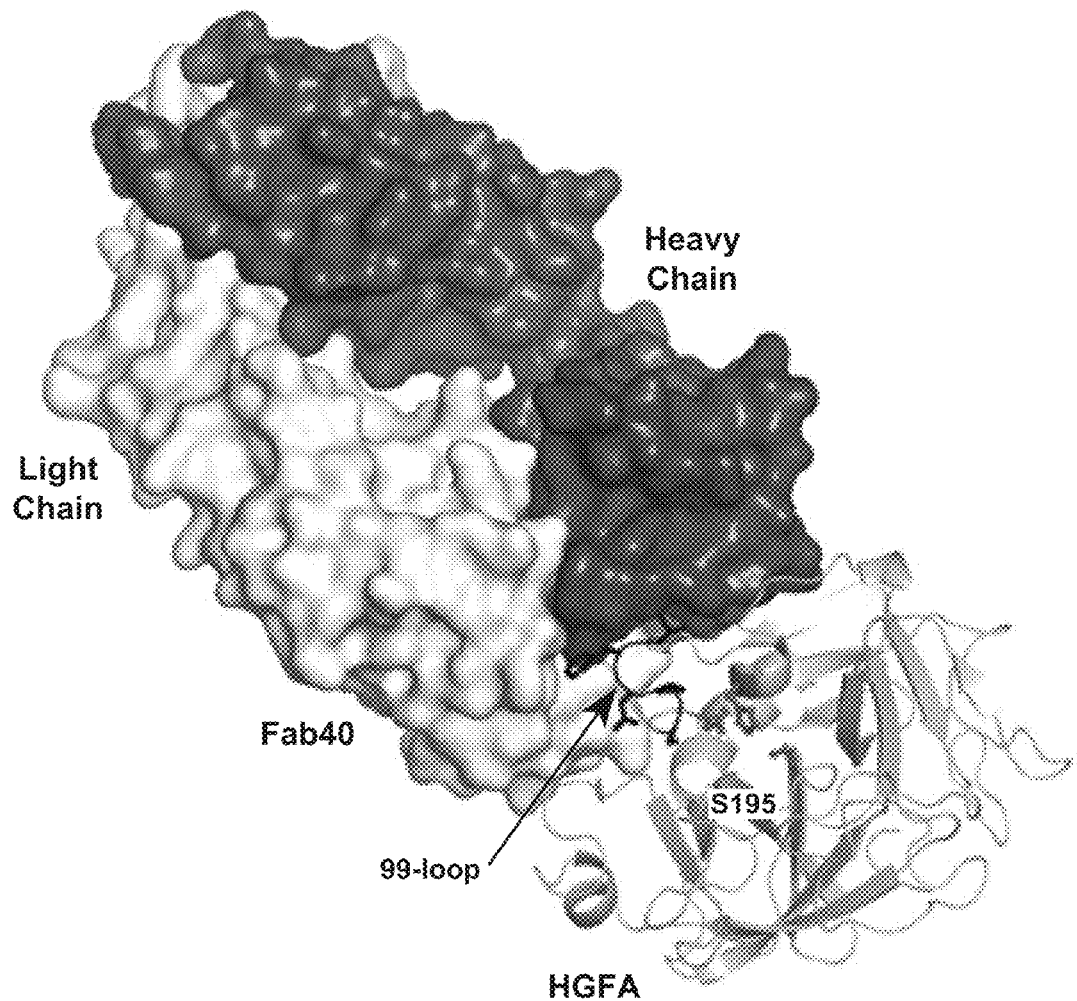
FIG. 4: Structure of HGFA/Fab40 complex. (a) Surface representation with secondary structure highlighted for the complex between HGFA (ribbon) and Fab40 (light chain: light grey and heavy chain: dark grey). The catalytic triad (His57-Asp 102-Ser195) residues are shown and the 99-loop is highlighted by the arrow. (b) Superposition of HGFA/Fab40 (light grey) structure with HGFA/Fab75 (Wu et al, 2007) (dark grey) showing no significant changes in the conformation of HGFA except for changes in the 99-loop (black).
Figure 4B:
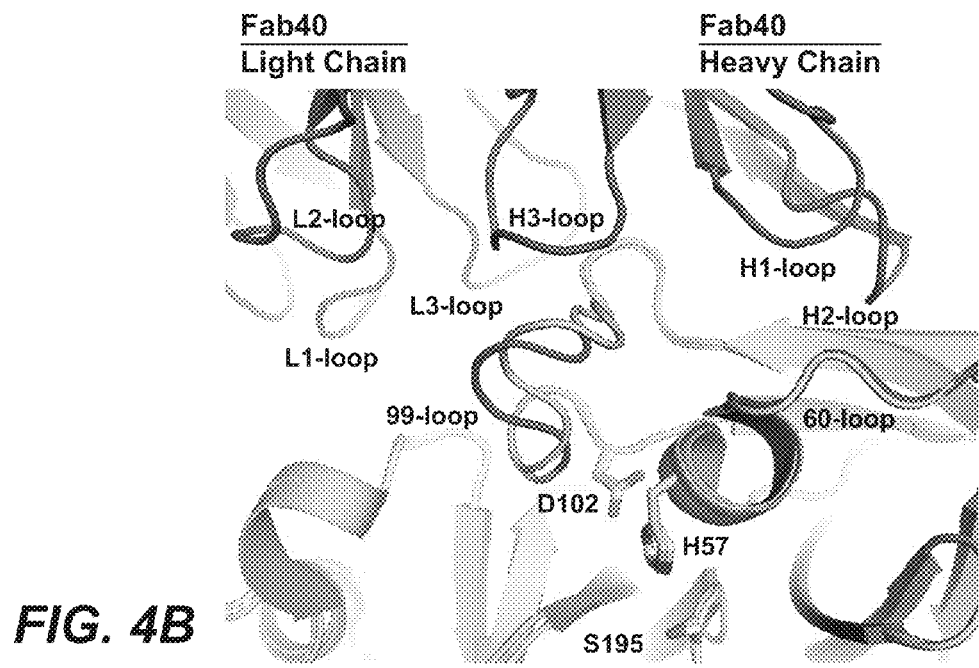
Figure 4C:
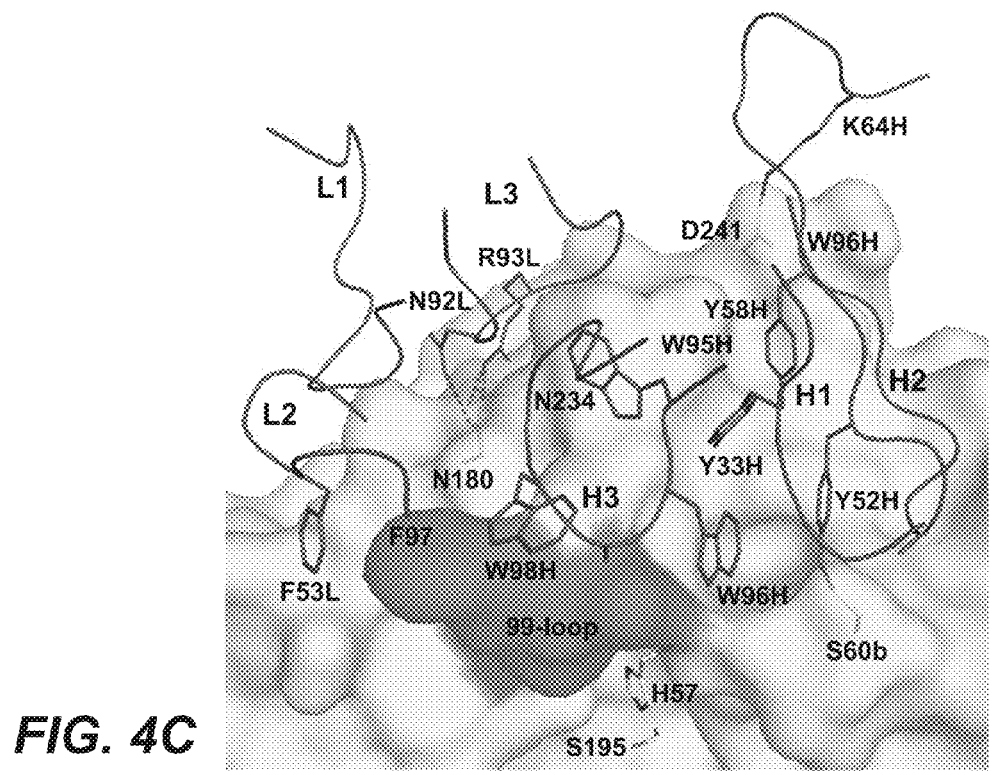
Figure 5A:
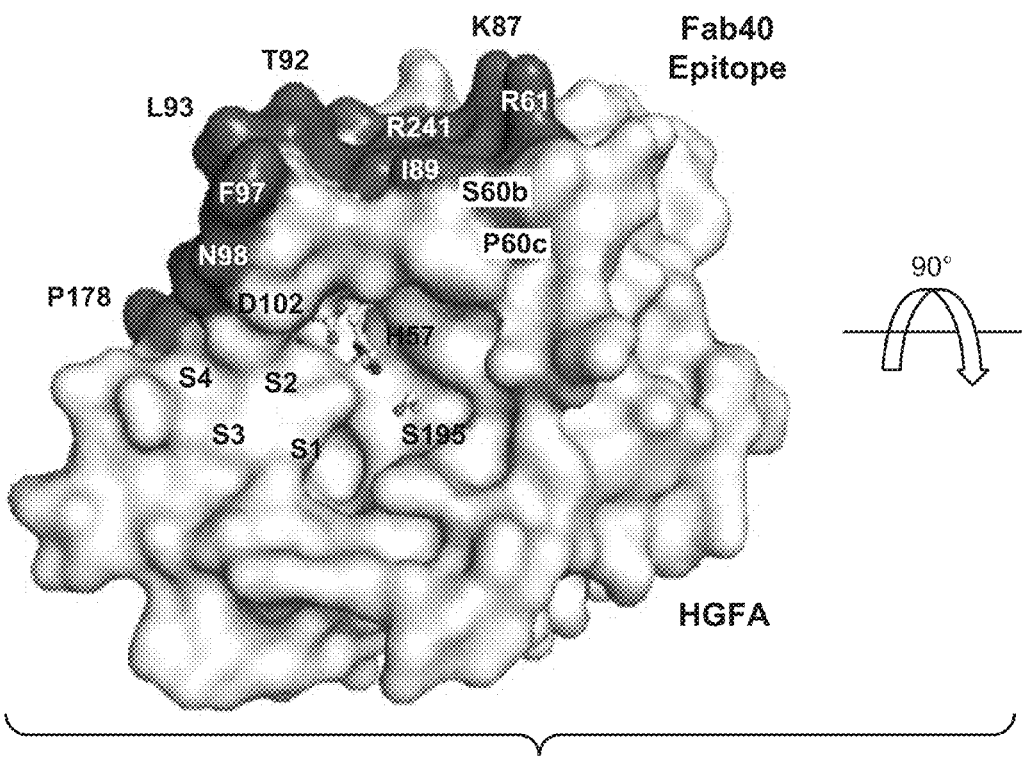

The 2.35 Å resolution structure of the HGFA/Fab40 complex shows that Fab40 uses all six CDR loops to bind to a flat epitope at the periphery of the substrate binding cleft, encompassing the 60-loop (e.g., native number 451-454; chymotrypsin numbers 60A-D) and 99-loop (e.g., native numbers 490-493; chymotrypsin numbers 96, 97, 98, and 99a) (FIG. 4a-b). The conformation of the catalytic triad (His-57, Asp-102 and Ser-195) has no significant changes compared to other known structures of HGFA (FIG. 4b) and the substrate subsites S1-S4 are unoccupied (FIG. 5a). The closest atom of Fab40 is >15 Å from the active site Ser195 residue indicating an allosteric mode of inhibition. The key feature of the HGFA/Fab40 complex is a large conformational change in the 99-loop (FIG. 4b and FIG. 10, illustrating the quality of the electron density map). No other significant changes in the HGFA structure are observed suggesting that this is the reason for antibody induced inhibition. The 'allosteric switch', embodied in the conformation of the 99-loop, is evident from the comparison of the HGFA/Fab40 structure with other structures of HGFA (Shia et al, 2005; Wu et al, 2007), in which the 99-loop is in a 'competent' conformation (catalytically active form of HGFA) state. The Phe97 of the 99-loop in the new conformation ('non-competent' conformation, catalytically inactive form of HGFA) is buried in a hydrophobic groove formed at the interface of light chain (Tyr49L, Ser50L and Phe53L) and heavy chain (Trp98H and Pro99H) of Fab40 (FIG. 4c). The epitope is centered on Leu-93 of the protruding 99-loop (FIG. 5a,b), which is sandwiched in a cleft between the CDR loops L3 and H3. The 99-loop and 60-loop are involved in intimate contacts mostly with heavy chain CDR residues. The heavy and light chains contribute 65% and 35% of buried surface area to the complex, respectively (FIG. 5c).

Figure 5B:
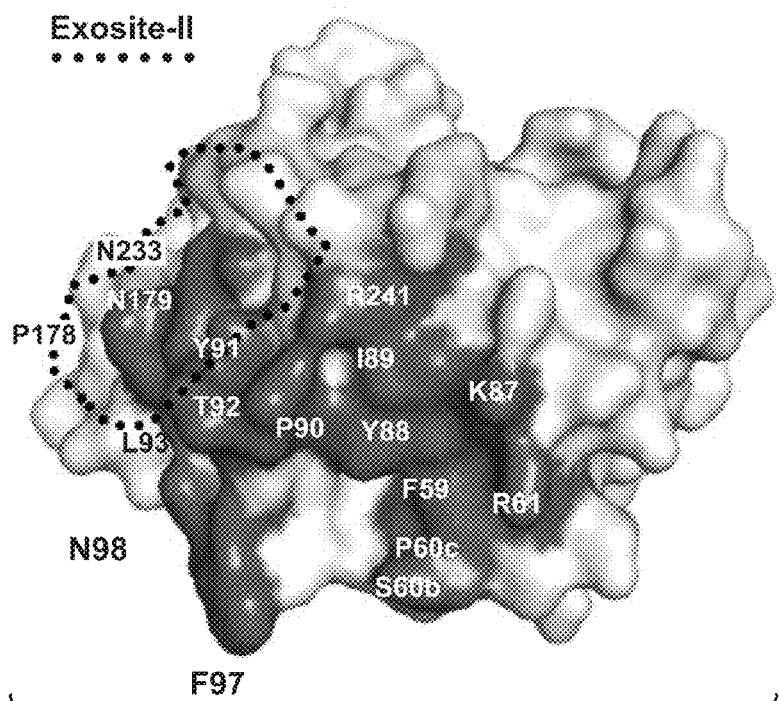

The total solvent-accessible surface area of HGFA buried upon Fab40 binding is ~1030 Å$^2$. Altogether, 18 hydrogen bonds and one electrostatic interaction (Asp241-Lys64H) are formed between HGFA and Fab40 (Table 3). Several hydrophobic residues like Trp95H, Trp96H, Trp98H and Tyr33H, Tyr52H, Tyr58H bind into small pockets at the back side of the 60- and 99-loops (FIG. 4c). The Fab40 epitope on HGFA has significant overlap with a region corresponding to exosite II in thrombin, an electropositive region that interacts with thrombin regulators (FIG. 5b). However, unlike exosite II interactions in coagulation proteases which are primarily electrostatic in nature (Bock et al, 2007), the binding of Fab40 to HGFA involves mainly hydrogen bonding and van der Waals interactions.

Figure 6C:
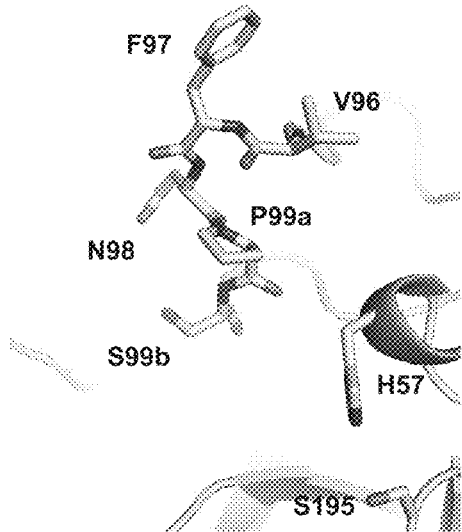
Figure 6D:
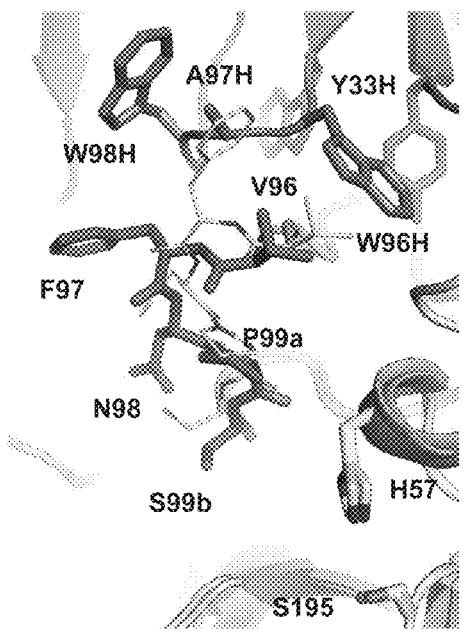

Flipping the 'Allosteric Switch': Engineering Ab40 to remove the Allosteric Inhibitory Activity The CDR-H3 loop of Fab40 contains three tryptophan residues (Trp95H, Trp96H and Trp98H) that form the core of the paratope (FIG. 5c). Trp96H is central to the observed conformational change in 99-loop, by docking its large indole side chain in a deep hydrophobic pocket formed by Ala56, Pro90, Tyr88, Val96, Val105 and Ile107 of HGFA (FIG. 6a). A small shift in the main chain as well as the side chain conformation of Val96 is transmitted through the rest of the 99-loop residues (Val96-Asp100), ultimately leading to >1 Å rmsd shift in $C_\alpha$ (99-loop) (FIG. 6c,d). To investigate the role of Trp96H in the conformational change and the associated allosteric inhibitory activity, we deleted this residue (Fab40.ΔTrp) to shorten the CDR-H3 loop (FIG. 1). The complex of HGFA with Fab40.ΔTrp was crystallized as described for the wild-type antibody.

Figure 6E:
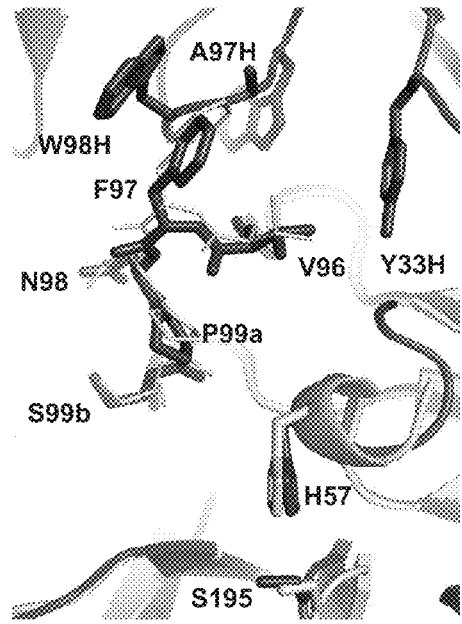
Figure 6F:
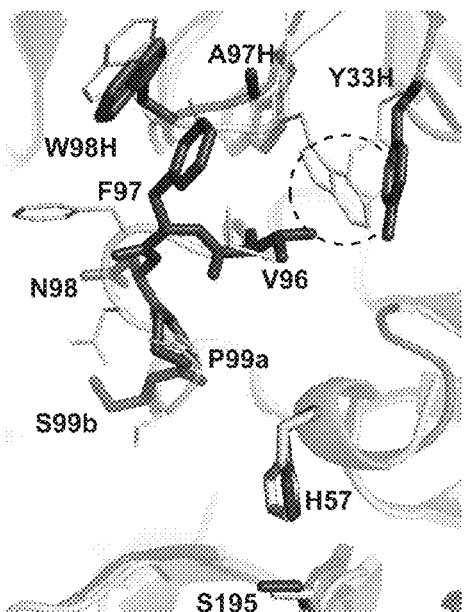

The overall structure of HGFA/Fab40.ΔTrp (2.90 Å) is very similar to that of HGFA/Fab40. The changes are very minimal and confined to residues Ala97H and Trp98H in the CDR-H3 loop (FIG. 6e-f). The side chain of Tyr33H flips around its $\chi^1$ torsion angle and partly fills the deep hydrophobic pocket which was occupied by Trp96H in the HGFA/Fab40 structure (FIG. 6b). The size of this hydrophobic pocket is now reduced due to the movement of residues lining this pocket, principally Ser60, Pro90 and Tyr94 of HGFA. Remarkably the 99-loop reverted to the 'competent' state, as observed in other structures of HGFA (FIG. 6e-f). Ab40.ΔTrp was no longer an inhibitor of HGFA as determined by enzymatic assays (FIG. 2b). It was striking that such a subtle change was enough to remove the inhibitory activity while retaining binding, albeit with much reduced affinity (Table 1). Moreover, unlike Ab40, presence of the KQLR (SEQ ID NO: 10) inhibitor in the HGFA active site did not affect Ab40.ΔTrp binding as indicated by the similar $K_D$ values for either HGFA or HGFA-KQLR complex ("KQLR" disclosed as SEQ ID NO: 10) (FIG. 3e,f). Thus, the data support our hypothesis that the mechanism of allosteric inhibitory activity by Ab40 is primarily driven by a significant change of the 99-loop conformation.

Structural Determinants for the Allosteric Mechanism of Inhibition

The 99-loop of HGFA is a critical substrate specificity determinant by contributing to interactions with substrate residues P2 and P4. Therefore, to obtain a detailed understanding on how the Ab40-induced movement of the 99-loop impacted these substrate subsite interactions, we attempted to determine the structure of the HGFA-KQLR complex ("KQLR" disclosed as SEQ ID NO: 10). The KQLR sequence (SEQ ID NO: 10) corresponds to the P4-P1 residues of the natural HGFA substrate pro-HGF. Unfortunately, these attempts were not successful in producing crystals of sufficient diffraction quality despite several attempts to optimize the crystallization conditions. As an alternative approach, we then focused our attention on solving the structure of HGFA-KQLR ("KQLR" disclosed as SEQ ID NO: 10) in complex Fab40.ΔTrp, which readily crystallized.

Figure 7A:
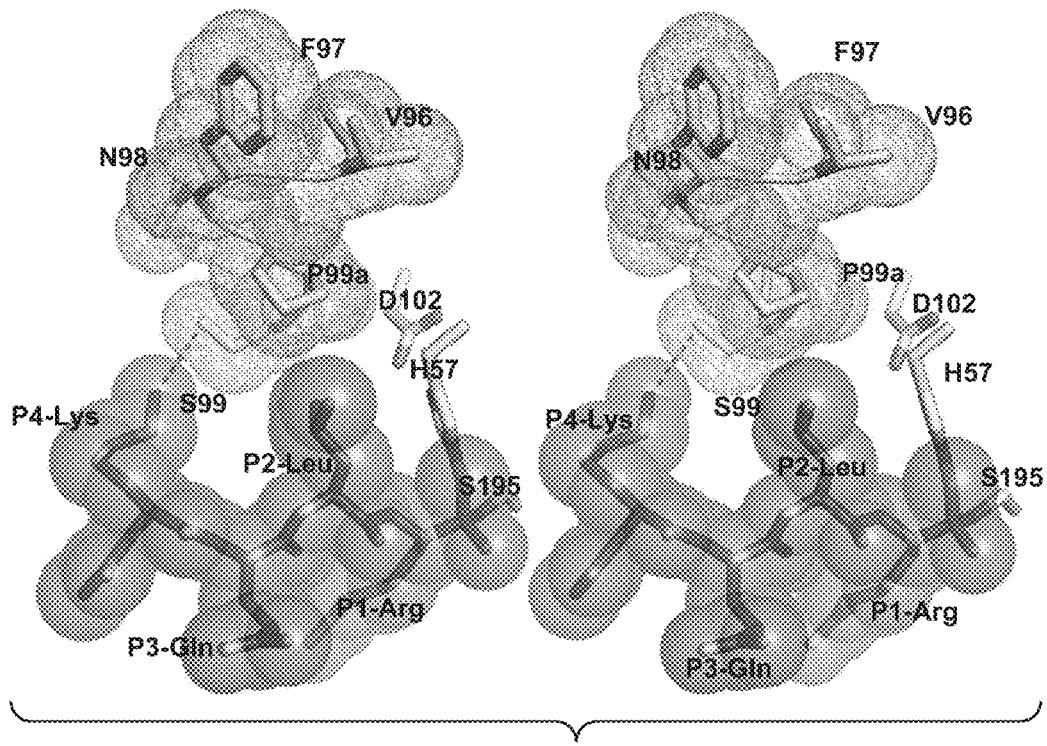
Figure 7B:
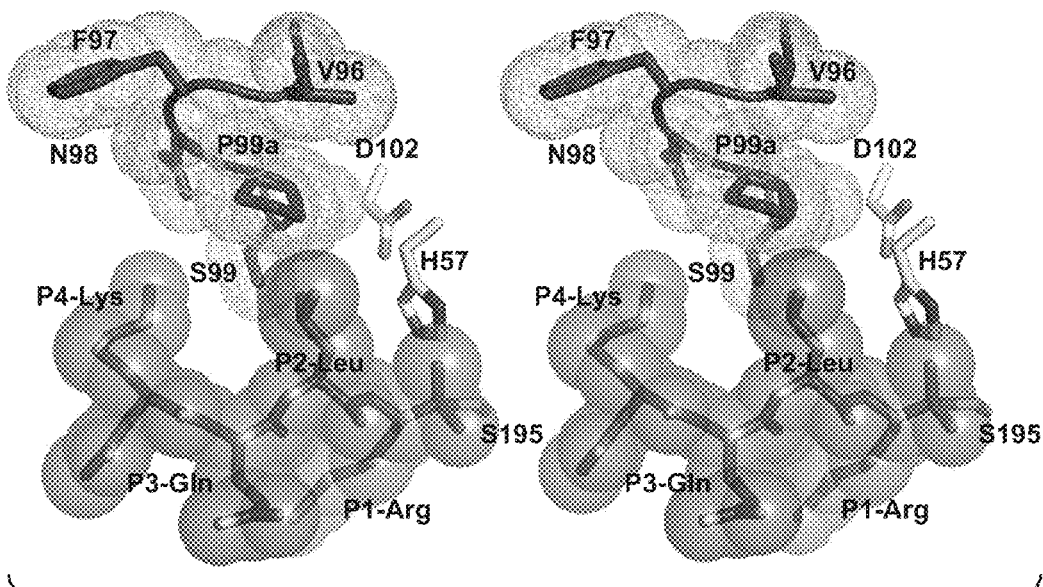
Figure 7C:
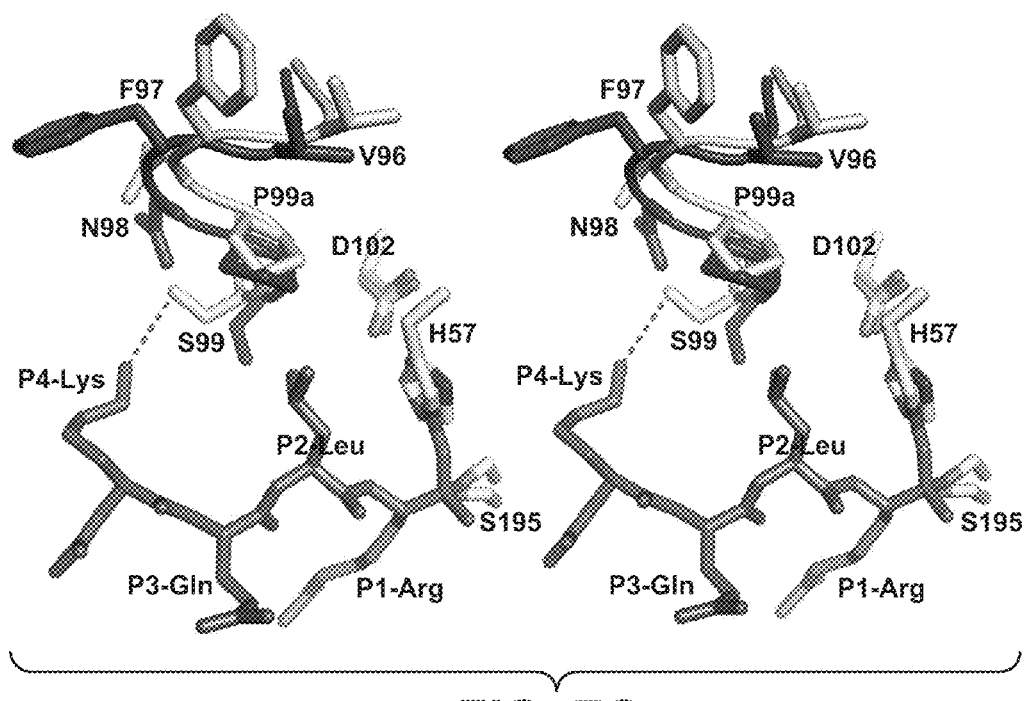

The electron density for peptidic inhibitor, Ac-KQLR-cmk ("KQLR" disclosed as SEQ ID NO: 10) was unambiguous in this 2.70 Å resolution structure. The peptidic inhibitor aligned in the active site groove in a twisted anti-parallel conformation forming the characteristic inter-main chain hydrogen bonds between P1-Arg and Ser214 and between P3-Gln and Gly216 (FIG. 11). The inhibitor was covalently linked to the catalytic Ser195 and His57 and the mode of binding at S4-S1 subsites are very similar to those observed in the complex of KQLR (SEQ ID NO: 10) with hepsin, another S1A protease family member (Herter et al, 2005). A salt bridge interaction pairs the P1-Arg of the peptidic inhibitor with Asp189 in the S1 subsite. There appears to be a strong preference for a Leucine at the P2 position, because the S2 subsite is a small hydrophobic pocket formed by residues Pro99a, Ser99, Trp215 and His57. The P2-Leu side chain tightly packs against the Pro99a, suggesting that minor changes in the conformation of Pro99a could have a major influence on P2 specificity (FIG. 7a). Thus the specificity at the S2 subsite for HGFA appears to be a distinguishing feature as is the case for many coagulation proteases. Selectivity for the P3 residue is poor in nearly all S1 peptidases as the enzyme—substrate interaction is limited due to solvent exposure of the P3 side chain. The P3-Glu points outward towards the solvent exposed region of the active site. Unlike most S1 peptidases, which possess poor selectivity for a P4 residue, in HGFA a hydrogen bond with Ser99 stabilizes the P4-Lys (FIG. 7a). Additionally, hydrophobic stabilization to the side chain of P4-Lys is offered by Trp215 of HGFA. The carbonyl oxygen from the N-terminal acetyl group is interacting with Asp217 of HGFA through a hydrogen bond.

The structure of the protease domain of HGFA in HGFA-KQLR/Fab40.ΔTrp complex ("KQLR" disclosed as SEQ ID NO: 10) is very similar to HGFA/Fab40.ΔTrp complex with rmsd (for all atoms) of 0.39 Å (FIG. 12). The conformation of the 99-loop in HGFA-KQLR/Fab40.ΔTrp ("KQLR" disclosed as SEQ ID NO: 10) structure is in the 'competent' state as found in HGFA/Fab40.ΔTrp and other structures of HGFA. Thus, the HGFA-KQLR/Fab40.ΔTrp ("KQLR" disclosed as SEQ ID NO: 10) is a good alternative in the absence of a HGFA-KQLR ("KQLR" disclosed as SEQ ID NO: 10) structure, to define the substrate binding subsites in HGFA. Superposition of HGFA/Fab40 structure with HGFA-KQLR/Fab40.ΔTrp ("KQLR" disclosed as SEQ ID NO: 10) revealed a plausible cause for the allosteric inhibition. The movement of the 99-loop lead to a partial collapse of the subsite S2 and the reorganization of subsite S4, perturbing the interactions with substrate residues P2 and P4. First, the movement of the 99-loop residues Pro99a and Ser99, which are part of the S2 pocket, positions them too close to the P2-Leu (FIG. 7b), creating a steric clash. Secondly, the repositioned hydroxyl side chain of the S4 residue Ser99 can no longer form the hydrogen bond with P4-Lys (FIG. 7a,b) and is positioned too close to P2-Leu. Furthermore, the movement of the S2 pocket residue Pro99a also plays a key role in defining the allosteric nature of the inhibition of KD1 binding to HGFA by Ab40. Superposition of HGFA/Fab40 and HGFA/KD1 (Shia et al, 2005) complexes showed that there was no overlap between the KD1-and Fab40 epitopes (FIG. 13). A model of HGFA/Fab40/KD1 predicts a possibility of Pro99a to sterically clash with Cys38 and Leu39 of KD1 at the S2 subsite.

Discussion

Allosteric regulation of an enzyme, by definition, involves an altered catalytic activity originating from a remote effector interaction site (Tsai et al, 2009). A variety of effectors including binding of small molecules or macromolecules, phosphorylation, etc., result in a signal, which may result in a signal, which may either activate or inhibit a particular function of the protein (Swain and Gierasch, 2006). Very few such systems are understood beyond knowledge of the effector interaction site and the site of altered activity. The exact route by which amino acids transmit the allosteric effect is, in general, very poorly known. Recent studies have provided new insight into the structural basis of protease inhibition by antibodies that target the enzyme active site (Farady et al, 2008; Wu et al, 2007). In contrast, the exact molecular mechanisms by which allosteric antibodies interfere with enzyme catalysis remain elusive. The findings presented herein, derived from comprehensive structural and kinetic studies, now provide a detailed view of how an allosteric antibody inhibits protease catalysis. Enzyme kinetic analysis demonstrates that the phage display-derived Ab40 is a competitive inhibitor of HGFA. Yet, Ab40 did not inhibit by 'classical' steric hindrance, since it bound to an epitope distant from the active site, thus defining a competitive inhibition mechanism that is allosteric in nature. Most importantly, the structure of Fab40/HGFA complex revealed the underlying conformational changes, i.e. the movement of the 99-loop, thereby establishing the structural basis for a functional conduit between epitope and active site.

The observed 99-loop flexibility is unusual in the family of trypsin-like serine proteases, since is not a part of the so-called 'activation domain', which comprises several intrinsically mobile surface loops (Huber and Bode, 1978). A known example of conformational flexibility is observed in the serine protease prostasin (Spraggon et al, 1990).

Ab40 binding was not accompanied by any major structural changes other than the 99-loop movement, strongly indicating that this was the cause for enzyme inhibition. To test this hypothesis, we removed one of the key interactions at the Ab40/HGFA interface, i.e. the hydrophobic contact between Trp96H and Val96 of HGFA. The structure of the generated Trp96H-deletion mutant Ab40.ΔTrp in complex with HGFA showed that the 99-loop had flipped back to the functionally 'competent' state, consistent with assay results showing that the Ab40.ΔTrp/HGFA complex was enzymatically active. Therefore, the 99-loop movement could be considered as an 'allosteric switch' regulating enzyme activity: the 'allosteric switch' is turned ON upon Ab40 binding locking the 99-loop in the 'non-competent' conformation, whereas antibody removal or binding of the Ab40.ΔTrp mutant turns the 'allosteric switch' OFF allowing the 99-loop to adopt the 'competent' conformation.

The question arose as to exactly how the 'non-competent' 99-loop conformation interferes with the catalytic machinery. That is, which amino acids are changed when Ab40 binds, and why do those changes alter enzyme activity? The 99-loop does not contribute to the formation of the Si specificity pocket and binding experiments confirmed that S1-P1 interactions were not affected by Ab40 binding. However, the 'front' side of the 99-loop in respect to the Ab40 epitope participates in shaping important substrate subsites and this is the region where obstructions likely arose. The structure of HGFA with the irreversibly bound KQLR peptide (SEQ ID NO: 10) provided a plausible answer. The KQLR peptide (SEQ ID NO: 10) constitutes the P4-P1 sequence of the natural substrate pro-HGF and also contains the P2-P1 residues, i.e. LR, of the synthetic pNA substrate S-2266 used in our enzyme assays.

Structural analysis showed that the 'non-competent' conformation of the 99-loop obstructed substrate access to S2 and S4 subsites, due to a steric clash between the P2-Leu and the S2 subsite (Pro99a and Ser99) and the loss of stabilizing interactions between P4-Lys and the S4 subsite. The hydrozyl side chain of Ser99 residue was found to adopt two different conformations, thus acting as a key specificity determinant at the S2 subsite. This observation is analogous to the conformational changes observed in Tyr99 of coagulation factor IX1 (Hopfner et al, 1999). In the 'competent' conformation the hydrophobic S2 pocket is ideally shaped to recognize Leu as a P2 residue, consistent with the presence of P2-Leu in the natural substrates pro-HGF and pro-MSP, as well as the synthetic S-2266 substrate. Therefore, the partial collapse of the S2 subsite by Ab40 binding may have sufficed to cause inhibition of enzyme catalysis towards both macromolecular and synthetic substrates. A caveat associated with this structural interpretation is our use of the HGFA-KQLR/Fab40. ΔTrp ("KQLR" disclosed as SEQ ID NO: 10) structure as a surrogate for that of HGFA-KQLR ("KQLR" disclosed as SEQ ID NO: 10), which we failed to crystallize. However, the 99-loop in the HGFA-KQLR/Fab40. ΔTrp ("KQLR" disclosed as SEQ ID NO: 10) structure adopts the 'competent' conformation and, therefore, we take this structure as to provide a very good approximation of the S4-S1 interactions with substrate. This view is supported by the observation that the conformation of the KQLR peptide (SEQ ID NO: 10) is virtually identical with that in the related KQLR-hepsin complex ("KQLR" disclosed as SEQ ID NO: 10) (Herter et al 2005). We thoroughly evaluated the influence of inter-molecular contacts on the interpretation of our results. The catalytic triad (H57-D102-S195) is not involved in crystal contacts in any of the three structures. Additionally, the 99-loop is not involved in crystal contacts in the structure of HGFA/Fab40 or HGFA-KQLR/Fab40. ΔTrp ("KQLR" disclosed as SEQ ID NO: 10). However, the 99-loop is stabilized by a symmetry related molecule in the case of HGFA/Fab40. ΔTrp (both molecules in the asymmetric unit). Since the conformation of the 99-loop in HGFA-KQLR/Fab40. ΔTrp ("KQLR" disclosed as SEQ ID NO: 10) is similar as in HGFA/Fab40. ΔTrp, we considered the impact from crystal contacts negligible.

The switch of the 99-loop can be considered as a mobile conduit that connects the inhibitor (i.e. Ab40) binding site with the substrate binding site. Such a view would also provide a suitable framework for understanding the competitive inhibition mode determined in enzymatic assays. Both inhibitor and substrate can apply forces on the 99-loop, albeit from opposite directions, resulting in 99-loop conformations that are sub-optimal with either substrate binding (non-competent' state) or inhibitor binding (competent' state). Structural models indicate that steric clashes occur in both situations, i.e. between the 99-loop and P2-Leu of substrate in the 'non-competent' state (FIG. 7c) and between the 99-loop and Trp96H, Ala97H and Trp98H in CDR-H3 of Fab40 in the 'competent' state (FIG. 14). Based on classical enzyme kinetics several models of competitive inhibition have been proposed, among them allosteric models, as illustrated by Segel (Segel, 1993). The elucidated allosteric mechanism is a refinement of the model-5 by Segel, as it provides the structural basis of the molecular linkage between inhibitor binding site and active site. The model in FIG. 8 shows the catalytically competent and inhibited states of enzyme in an equilibrium favoring the competent state. In this model, the binding of Ab40 to the transient 'non-competent' state (allosteric site*) simply shifts the equilibrium away from the functionally active state, thus driving the major population of enzyme molecules from the 'allosteric switch' "OFF" state to the "ON" state. The model also accounts for the competitive nature of HGFA inhibition, in that an increase of substrate concentration will shift the equilibrium to the left, i.e. to the 'competent' state of HGFA allowing catalysis to proceed. The mutated Ab40.ΔTrp does not impede catalysis, because it only binds to the 'competent' state in which the 'allosteric switch' is turned OFF. This interpretation is consistent with the generally accepted view of allostery in that effector binding leads to a shift in the ensemble of protein conformations, thus altering the relative populations of particular states. Ab40 binding to HGFA effectively resulted in a shift/redistribution from the 'competent' to a 'non-competent' state and thus to a functionally impaired enzyme. Extending this view to the Ab40. ΔTrp, it can also be regarded as allosteric effector, which imposes only small or negligible effects on the binding site, thereby sampling the 'competent' enzyme conformation.

The 'allosteric switch' is a relatively simple allosteric mechanism. It involves only one mobile surface loop, which directly links allosteric effector binding site with the active site. It contrasts with other more complex and less understood allosteric mechanisms, such as cofactor-induced enzyme activation (Olsen and Persson, 2008) or PDZ-domain mediated inhibition/activation of HtrA1 family members (Sohn et al, 2007), where effector binding is associated with multiple, short- and long-range conformational changes. Nevertheless, despite its relative simplicity it may replicate a naturally occurring allosteric regulation mechanism of HGFA activity by yet unknown effector molecules. In particular, the Ab40 binding site significantly overlaps with the exosite II of thrombin and the corresponding region of coagulation factors IX and X, which are docking sites for various allosteric effectors, including heparin. However, the corresponding region of HGFA appears ill-suited to bind heparin, because the prominent cluster of Arg and Lys residues that mediate exosite-heparin interactions in coagulation factors is minimally represented in HGFA.

Research on allosteric inhibitors have been actively pursued for kinases (Vajpai et al., 2008) and GPCR's (Raddatz et al., 2007) among others. It is interesting to note that the mechanism of allosteric inhibition by Ab40 is similar to some of the other known allosteric small molecule inhibitors, in either case, the allosteric inhibitor act by restricting the conformational flexibility in the enzyme active site (Goodey and Benkovic, 2008; Lee and Craik, 2009).

Allosteric anti-protease antibodies may have great therapeutic potential, since they are potent and highly specific and are safeguarded from any inadvertent processing by their target protease. However, their use as therapeutic agents is currently limited to extracellular proteases, while intracellular proteases are primarily targeted by orthosteric small molecule inhibitors. In this respect, our findings may suggest new approaches to identify allosteric 'hot spots' that might be amenable to structure-based design of allosterically acting peptidic or small molecule inhibitor (Hardy and Wells, 2004). Specifically, the herein described interaction of Trp96H with a large hydrophobic pocket (hot spot') is critical in stabilizing the non-competent 99-loop conformation, yet the existence of this pocket could not have been predicted from other HGFA structures. Thus, large scale screening of Fab phage display libraries in conjunction with Fab/protease structure determination may identify promising allosteric 'hot spots'. Such an approach should further benefit from the intrinsic property of Fabs to facilitate crystallization of proteins (Tereshko et al, 2008).

Another aspect of our study is the potential usefulness of the anti-HGFA antibody to experimentally address the roles of HGFA in pathologic pathways. For instance, it was suggested that the ability of HGFA to efficiently process pro-HGF and consequently stimulate the HGF/Met signaling pathway may contribute to cancer growth (Kataoka et al., 2003a). Ab40 binds to and blocks mouse HGFA equally well as human HGFA (data not shown), making it an ideal reagent for further investigation of HGFA function in mouse tumor models.

PARTIAL REFERENCE LIST

Adams, G. P., and Weiner, L. M. (2005). Monoclonal antibody therapy of cancer. Nat Biotech 23, 1147-1157.

Barrett, A. J., Rawlings, N. D., and Woessner, J. F. (1998). Handbook of Proteolytic Enzymes. (San Diego: Academic Press).

Bjelke, J. R., Olsen, O. H., Fodje, M., Svensson, L. A., Bang, S., Bolt, G., Kragelund, B. B., and Persson, E. (2008). Mechanism of the Ca2+-induced Enhancement of the Intrinsic Factor VIIa Activity. J Biol Chem 283, 25863-25870.

Bock, P. E., Panizzi, P., and Verhamme, I. M. (2007). Exosites in the substrate specificity of blood coagulation reactions. J Thromb Haemost 5 Suppl 1, 81-94.

CCP4 (1994). The CCP4 suite: Programs for protein crystallography. Acta Crystallogr D50, 760-763.

Changeux, J. P., and Edelstein, S. J. (2005). Allosteric mechanisms of signal transduction. Science 308, 1424-1428.

del Sol, A., Tsai, C. J., Ma, B., and Nussinov, R. (2009). The origin of allosteric functional modulation: multiple preexisting pathways. Structure 17, 1042-1050.

Di Cera, E. (2006). A structural perspective on enzymes activated by monovalent cations. J Biol Chem 281, 1305-1308.

Egeblad, M., and Werb, Z. (2002). New functions for the matrix metalloproteinases in cancer progression. Nature Rev. Cancer 2, 161-174.

Eigenbrot, C., and Kirchhofer, D. (2002). New Insight into How Tissue Factor Allosterically Regulates Factor VIIa. Trends in Cardiovascular Medicine 12, 19-26.

Farady, C. J., Egea, P. F., Schneider, E. L., Darragh, M. R., and Craik, C. S. (2008). Structure of an Fab-Protease Complex Reveals a Highly Specific Non-canonical Mechanism of Inhibition. Journal of Molecular Biology 380, 351-360.

Fenton, A. W. (2008). Allostery: an illustrated definition for the 'second secret of life'. Trends in biochemical sciences 33, 420-425.

Friedrich, R., Panizzi, P., Fuentes-Prior, P., Richter, K., Verhamme, I., Anderson, P. J., Kawabata, S.-I., Huber, R., Bode, W., and Bock, P. E. (2003). Staphylocoagulase is a prototype for the mechanism of cofactor-induced zymogen activation. Nature 425, 535-539.

Goodey, N. M., and Benkovic, S. J. (2008). Allosteric regulation and catalysis emerge via a common route. Nature chemical biology 4, 474-482.

Gunasekaran, K., Ma, B., and Nussinov, R. (2004). Is allostery an intrinsic property of all dynamic proteins? Proteins 57, 433-443.

Hardy, J. A., Lam, J., Nguyen, J. T., O'Brien, T., and Wells, J. A. (2004). Discovery of an allosteric site in the caspases. Proceedings of the National Academy of Sciences of the United States of America 101, 12461-12466.

Hardy, J. A., and Wells, J. A. (2004). Searching for new allosteric sites in enzymes. Current opinion in structural biology 14, 706-715.

Hardy, J. A., and Wells, J. A. (2009). Dissecting an allosteric switch in caspase-7 using chemical and mutational probes. J Biol. Chem.

Hauske, P., Ottmann, C., Meltzer, M., Ehrmann, M., and Kaiser, M. (2008). Allosteric regulation of proteases. Chembiochem 9, 2920-2928.

Hedstrom, L. (2002). Serine protease mechanism and specificity. Chemical reviews 102, 4501-4524.

Herter, S., *Piper*, D. E., Aaron, W., Gabriele, T., Cutler, G., Cao, P., Bhatt, A. S., Choe, Y., Craik, C. S., Walker, N., et al. (2005). Hepatocyte growth factor is a preferred in vitro substrate for human hepsin, a membrane-anchored serine protease implicated in prostate and ovarian cancers. Biochem J 390, 125-136.

Hooper, N. M. (2002). Proteases in Biology and Medicine. In Essays in Biochemistry (London: Portland Press).

Hopfner, K. P., Lang, A., Karcher, A., Sichler, K., Kopetzki, E., Brandstetter, H., Huber, R., Bode, W., and Engh, R. A. (1999). Coagulation factor IXa: the relaxed conformation of Tyr99 blocks substrate binding. Structure 7, 989-996.

Huber, R., and Bode, W. (1978). Structural basis of the activation and action of trypsin. Acc. Chem. Res. 11, 114-122.

Huntington, J. A. (2008). How Na+ activates thrombin—a review of the functional and structural data. Biological chemistry 389, 1025-1035.

Kabat, E. A., Wu, T. T., Perry, H. M., Gottesman, K. S., and Foeller, C. (1991). Sequences of proteins of immunological interest, fifth edition. (National Institutes of Health, Bethesda Md.).

Kataoka, H., Miyata, S., Uchinokura, S., and Itoh, H. (2003a). Roles of hepatocyte growth factor (HGF) activator and HGF activator inhibitor in the pericellular activation of HGF/scatter factor. Cancer and Metastasis Reviews 22, 223-236.

Kataoka, H., Miyata, S., Uchinokura, S., and Itoh, H. (2003b). Roles of hepatocyte growth factor (HGF) activator and HGF activator inhibitor in the pericellular activation of HGF/scatter factor. Cancer metastasis reviews 22, 223-236.

Kawaguchi, M., Orikawa, H., Baba, T., Fukushima, T., and Kataoka, H. (2009). Hepatocyte growth factor activator is a serum activator of single-chain precursor macrophage-stimulating protein. The FEBS journal 276, 3481-3490.

Kirchhofer, D., Peek, M., Li, W., Stamos, J., Eigenbrot, C., Kadkhodayan, S., Elliott, J. M., Corpuz, R. T., Lazarus, R. A., and Moran, P. (2003). Tissue expression, protease specificity, and Kunitz domain functions of hepatocyte growth factor activator inhibitor-1B (HAI-1B), a new splice variant of HAI-1. J Biol Chem 278, 36341-36349.

Krauss, G. (2003). Biochemistry of Signal Transduction and Regulation. G. Krauss, ed. (New York: Wiley and Sons), pp. 89-114.

Lee, C. V., Liang, W. C., Dennis, M. S., Eigenbrot, C., Sidhu, S. S., and Fuh, G. (2004a). High-affinity human antibodies from phage-displayed synthetic Fab libraries with a single framework scaffold. J Mol Biol 340, 1073-1093.

Lee, C. V., Sidhu, S. S., and Fuh, G. (2004b). Bivalent antibody phage display mimics natural immunoglobulin. J Immunol Methods 284, 119-132.

Lee, G. M., and Craik, C. S. (2009). Trapping moving targets with small molecules. Science 324, 213-215.

Liang, W. C., Dennis, M. S., Stawicki, S., Chanthery, Y., Pan, Q., Chen, Y., Eigenbrot, C., Yin, J., Koch, A. W., Wu, X., et al. (2007). Function blocking antibodies to neuropilin-1 generated from a designed human synthetic antibody phage library. J Mol Biol 366, 815-829.

Luttun, A., Dewerchin, M., Collen, D., and Carmeliet, P. (2000). The role of proteinases in angiogenesis, heart development, restenosis, atherosclerosis, myocardial ischemia, and stroke: insights from genetic studies. Curr. Atheroscler. Rep. 2, 407-416.

McCoy, A. J., Grosse-Kunstleve, R. W., Storoni, L. C., and Read, R. J. (2005). Likelihood-enhanced fast translation functions. Acta Crystallogr D Biol Crystallogr 61, 458-464.

Miyazawa, K., Shimomura, T., Kitamura, A., Kondo, J., Morimoto, Y., and Kitamura, N. (1993). Molecular cloning and sequence analysis of the cDNA for a human serine protease responsible for activation of hepatocyte growth factor. Structural similarity of the protease precursor to blood coagulation factor XII. J Biol Chem 268, 10024-10028.

Monod, J. (1977). Chance and Necessity: Essay on the Natural Philosophy of Modern Biology (Penguin Books).

Olsen, O., and Persson, E. (2008). Cofactor-induced and mutational activity enhancement of coagulation factor VIIa. Cellular and Molecular Life Sciences (CMLS) 65, 953-963.

Otwinowski, Z., and Minor, W. (1997). Processing of X-ray diffraction data collected in oscillation mode. In: Macromolecular Crystallography Part A. Methods in Enzymol. 276, 307-326.

Parr, C., and Jiang, W. G. (2001). Expression of hepatocyte growth factor/scatter factor, its activator, inhibitors and the c-Met receptor in human cancer cells. International journal of oncology 19, 857-863.

Pellicena, P., and Kuriyan, J. (2006). Protein-protein interactions in the allosteric regulation of protein kinases. Current opinion in structural biology 16, 702-709.

Perutz, M. F. (1970). Stereochemistry of cooperative effects in haemoglobin. Nature 228, 726-739.

Peterson, J. R., and Golemis, E. A. (2004). Autoinhibited proteins as promising drug targets. J Cell Biochem 93, 68-73.

Raddatz, R., Schaffhauser, H., and Marino, M. J. (2007). Allosteric approaches to the targeting of G-protein-coupled receptors for novel drug discovery: a critical assessment. Biochemical pharmacology 74, 383-391.

Rawlings, N. D., Morton, F. R., Kok, C. Y., Kong, J., and Barrett, A. J. (2008). MEROPS: the peptidase database. Nucleic Acids Res 36, D320-325.

Segel, I. (1993). Enzyme Kinetics: Behavior and Analysis of Rapid Equilibrium and Steady-State Enzyme Systems, Vol pp 161-226 (New York: Wiley).

Shia, S., Stamos, J., Kirchhofer, D., Fan, B., Wu, J., Corpuz, R. T., Santell, L., Lazarus, R. A., and Eigenbrot, C. (2005). Conformational lability in serine protease active sites: structures of hepatocyte growth factor activator (HGFA) alone and with the inhibitory domain from HGFA inhibitor-1B. J Mol Bio1346, 1335-1349.

Shimomura, T., Miyazawa, K., Komiyama, Y., Hiraoka, H., Naka, D., Morimoto, Y., and Kitamura, N. (1995). Activation of hepatocyte growth factor by two homologous proteases, blood-coagulation factor XIIa and hepatocyte growth factor activator. Eur J Biochem 229, 257-261.

Sohn, J., Grant, R. A., and Sauer, R. T. (2007). Allosteric Activation of DegS, a Stress Sensor PDZ Protease. Cell 131, 572-583.

Spraggon, G., Hornsby, M., Shipway, A., Tully, D. C., Bursulaya, B., Danahay, H., Harris, J. L., and Lesley, S. A. (2009). Active site conformational changes of prostasin provide a new mechanism of protease regulation by divalent cations. Protein Sci 18, 1081-1094.

Swain, J. F., and Gierasch, L. M. (2006). The changing landscape of protein allostery. Current opinion in structural biology 16, 102-108.

Tereshko, V., Uysal, S., Koide, A., Margalef, K., Koide, S., and Kossiakoff, A. A. (2008). Toward chaperone-assisted crystallography: protein engineering enhancement of crystal packing and X-ray phasing capabilities of a camelid single-domain antibody (VHH) scaffold. Protein Sci 17, 1175-1187.

Tsai, C. J., Del Sol, A., and Nussinov, R. (2009). Protein allostery, signal transmission and dynamics: a classification scheme of allosteric mechanisms. Molecular bioSystems 5, 207-216.

Turk, B. (2006). Targeting proteases: successes, failures and future prospects. Nature reviews 5, 785-799.

Vajpai, N., Strauss, A., Fendrich, G., Cowan-Jacob, S. W., Manley, P. W., Grzesiek, S., and Jahnke, W. (2008). Solution conformations and dynamics of ABL kinase-inhibitor complexes determined by NMR substantiate the different binding modes of imatinib/nilotinib and dasatinib. J Biol Chem 283, 18292-18302.

Wells, C. M., and Di Cera, E. (1992). Thrombin is a Na(+)-activated enzyme. Biochemistry 31, 11721-11730.

Wu, Y., Eigenbrot, C., Liang, W.-C., Stawicki, S., Shia, S., Fan, B., Ganesan, R., Lipari, M. T., and Kirchhofer, D. (2007). Structural insight into distinct mechanisms of protease inhibition by antibodies. Proceedings of the National Academy of Sciences 104, 19784-19789.

Xu, Z., Horwich, A. L., and Sigler, P. B. (1997). The crystal structure of the asymmetric GroEL-GroES-(ADP)7 chaperonin complex. Nature 388, 741-750.

Yu, E. W., and Koshland, D. E., Jr. (2001). Propagating conformational changes over long (and short) distances in proteins. Proceedings of the National Academy of Sciences of the United States of America 98, 9517-9520.

The invention claimed is:

1. An isolated anti-HGFA antibody, wherein the antibody comprises a light chain variable region comprising (a) HVR-L1 comprising sequence RASQDVSTAVA (SEQ ID NO:1); (b) HVR-L2 comprising sequence SASFLYS (SEQ ID NO:2); (c) HVR-L3 comprising sequence QQSNRAPAT (SEQ ID NO:3); and a heavy chain variable region comprising (d) HVR-H1 comprising sequence GTYIH (SEQ ID NO:4); (e) HVR-H2 comprising sequence GIYPAGGATYYADSVKG (SEQ ID NO:5); and (f) HVR-H3 comprising sequence WWAWPAFDY (SEQ ID NO:6).

2. The antibody of claim 1, wherein a full length IgG form of the antibody specifically binds human HGFA with a binding affinity of 20 pm or lower.

3. The antibody of claim 1, wherein the antibody binds to at least one, two, three, four, or any number up to all of residues 449, 450, 452, 453, 455, 480, 481, 482, 483, 484, 485, 486, 487, 488, 489, 490, 491, 496, 578, 579, 580, 636, 637, 640, 643, 644 of HGFA according to native sequential residue numbering, and further wherein the antibody allosterically inhibits HGFA and competes for binding to HGFA with HGFA active site blocker KD1 or Ac-KQLR-chloromethyl ketone ("KQLR" disclosed as SEQ ID NO: 10), but does not compete for binding to HGFA with benzamidine.

4. The antibody of claim 1, comprising a light chain variable domain having the sequence:
DIQMTQSPSSLSASVGDRVTITCRASQD-VSTAVAWYQQKPGKAPKLLIYSASFLYSG VPSRFSGSGSGTDFTLTISSLQPEDFA-TYYCQQSNRAPATFGQGTKVEIKR (SEQ ID NO:8); and further comprising a heavy chain variable domain.

5. The antibody of claim 1, comprising a heavy chain variable domain having the sequence:
EVQLVESGGGLVQPGGSLRLSCAASGFT-FNGTYIHWVRQAPGKGLEWVGGIYPAGGATYY ADSVKGRFTISRDNSKNTLYLQMNSL-RAEDTAVYYCAKWWAWPAFDYWGQGTLVTVSS (SEQ ID NO:9); and further comprising a light chain variable domain.

6. The antibody of claim 1, comprising a light chain variable domain having the sequence:

DIQMTQSPSSLSASVGDRVTITCRASQD-VSTAVAWYQQKPGKAPKLLIYSASFLYSG VPSRFSGSGSGTDFTLTISSLQPEDFA-TYYCQQSNRAPATFGQGTKVEIKR (SEQ ID NO:8); and a heavy chain variable domain having the sequence:

EVQLVESGGGLVQPGGSLRLSCAASGFT-FNGTYIHWVRQAPGKGLEWVGGIYPAGGATYY ADSVKGRFTISRDNSKNTLYLQMNSL-RAEDTAVYYCAKWWAWPAFDYWGQGTLVTVSS (SEQ ID NO:9).

7. The antibody of claim 1, wherein the antibody comprises human κ subgroup consensus framework sequence.

8. The antibody of claim 1, wherein the antibody comprises heavy chain human subgroup III consensus framework sequence.

9. The antibody of claim 8, wherein the antibody comprises a substitution at one or more of position 71, 73, or 78 according to Kabat numbering.

10. The antibody of claim 9, wherein the substitution is one or more of R71A, N73T, or N78A.

11. The antibody of claim 1, wherein the antibody is a monoclonal antibody.

12. The antibody of claim 1, wherein the antibody is an IgG1 antibody.

13. The antibody of claim 1, wherein the antibody is an antibody fragment.

14. An immunoconjugate comprising the antibody of claim 1 and a cytotoxic agent.

15. A pharmaceutical formulation comprising the antibody of claim 1 and a pharmaceutically acceptable carrier.

16. The pharmaceutical formulation of claim 15, further comprising an additional therapeutic agent.

* * * * *

SEQUENCE LISTING

```
<160> NUMBER OF SEQ ID NOS: 47

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Asp Val Ser Thr Ala Val Ala
1               5                   10
```

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Ser Asn Arg Ala Pro Ala Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Thr Tyr Ile His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ile Tyr Pro Ala Gly Gly Ala Thr Tyr Tyr Ala Asp Ser Val Lys
1               5                   10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Trp Ala Trp Pro Ala Phe Asp Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Gln Gln Ser Tyr Thr Thr Pro Pro Thr
1               5

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Arg Ala Pro Ala
                85                  90                  95

Thr Phe Gly Gln Gly Thr Lys Val Glu Ile Lys Arg
            100                 105

<210> SEQ ID NO 9
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Gly Thr
            20                  25                  30

Tyr Ile His Trp Val Arg Gln Ala Pro Gly Lys Gly Leu Glu Trp Val
        35                  40                  45

Gly Gly Ile Tyr Pro Ala Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Trp Ala Trp Pro Ala Phe Asp Tyr Trp Gly Gln Gly Thr
            100                 105                 110

Leu Val Thr Val Ser Ser
        115

<210> SEQ ID NO 10
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 10

Lys Gln Leu Arg
1

<210> SEQ ID NO 11
<211> LENGTH: 25
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 12
<211> LENGTH: 13
<212> TYPE: PRT
<213> ORGANISM: Homo sapiens

<400> SEQUENCE: 12

Trp Val Arg Gln Ala Pro Gly Lys Gly Leu Glu Trp Val
1               5                   10

<210> SEQ ID NO 13
<211> LENGTH: 30
<212> TYPE: PRT
<213> ORGANISM: Homo sapiens

<400> SEQUENCE: 13

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 14
<211> LENGTH: 11
<212> TYPE: PRT
<213> ORGANISM: Homo sapiens

<400> SEQUENCE: 14

Trp Gly Gln Gly Thr Leu Val Thr Val Ser Ser
1               5                   10

<210> SEQ ID NO 15
<211> LENGTH: 23
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
```

```
<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Homo sapiens

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 10
<212> TYPE: PRT
<213> ORGANISM: Homo sapiens

<400> SEQUENCE: 18

Phe Gly Gln Gly Thr Lys Val Glu Ile Lys
1               5                   10

<210> SEQ ID NO 19
<211> LENGTH: 650
<212> TYPE: PRT
<213> ORGANISM: Homo sapiens

<400> SEQUENCE: 19

Met Gly Arg Trp Ala Trp Val Pro Ser Pro Trp Pro Pro Pro Gly Leu
1               5                   10                  15

Gly Pro Phe Leu Leu Leu Leu Leu Leu Leu Leu Leu Pro Arg Gly
            20                  25                  30

Phe Gln Pro Gln Pro Gly Gly Asn Arg Thr Glu Ser Pro Glu Pro Asn
        35                  40                  45

Ala Thr Ala Thr Pro Ala Ile Pro Thr Ile Leu Val Thr Ser Val Thr
    50                  55                  60

Ser Glu Thr Pro Ala Thr Ser Ala Pro Glu Ala Gly Pro Gln Ser
65                  70                  75                  80

Gly Gly Leu Pro Pro Pro Arg Ala Val Pro Ser Ser Ser Pro
            85                  90                  95

Gln Ala Gln Ala Leu Thr Glu Asp Gly Arg Pro Cys Arg Phe Pro Phe
            100                 105                 110

Arg Tyr Gly Gly Arg Met Leu His Ala Cys Thr Ser Glu Gly Ser Ala
            115                 120                 125

His Arg Lys Trp Cys Ala Thr Thr His Asn Tyr Asp Arg Asp Arg Ala
        130                 135                 140

Trp Gly Tyr Cys Val Glu Ala Thr Pro Pro Gly Gly Pro Ala Ala
145                 150                 155                 160

Leu Asp Pro Cys Ala Ser Gly Pro Cys Leu Gly Ser Cys Ser Asn Thr
            165                 170                 175

Gln Asp Pro Gln Ser Tyr His Cys Ser Cys Pro Arg Ala Phe Thr Gly
            180                 185                 190

Lys Asp Cys Gly Thr Glu Lys Cys Phe Asp Glu Thr Arg Tyr Glu Tyr
            195                 200                 205

Leu Glu Gly Gly Asp Arg Trp Ala Arg Val Arg Gln Gly His Val Glu
        210                 215                 220
```

```
Gln Cys Glu Cys Gly Arg Thr Trp Cys Glu Gly Thr Arg His Thr Ala
225                 230                 235                 240

Cys Leu Ser Ser Pro Cys Leu Asn Gly Gly Thr Cys His Leu Ile Val
            245                 250                 255

Ala Thr Gly Thr Thr Val Cys Ala Cys Pro Pro Gly Phe Ala Gly Arg
        260                 265                 270

Leu Cys Asn Ile Glu Pro Asp Glu Arg Cys Phe Leu Gly Asn Gly Thr
    275                 280                 285

Gly Tyr Arg Gly Val Ala Ser Thr Ser Ala Ser Gly Leu Ser Cys Leu
290                 295                 300

Ala Trp Asn Ser Asp Leu Leu Tyr Gln Glu Leu His Val Asp Ser Val
305                 310                 315                 320

Gly Ala Ala Ala Leu Leu Gly Leu Gly Pro His Ala Tyr Cys Arg Asn
                325                 330                 335

Pro Asp Asn Asp Glu Arg Pro Trp Cys Tyr Val Lys Asp Ser Ala Leu
            340                 345                 350

Ser Trp Glu Tyr Cys Arg Leu Glu Ala Cys Glu Ser Leu Thr Arg Val
        355                 360                 365

Gln Leu Ser Pro Asp Leu Leu Ala Thr Leu Pro Glu Pro Ala Ser Pro
370                 375                 380

Gly Arg Gln Ala Cys Gly Arg Arg His Lys Lys Arg Thr Phe Leu Arg
385                 390                 395                 400

Pro Arg Ile Ile Gly Gly Ser Ser Ser Leu Pro Gly Ser His Pro Trp
                405                 410                 415

Leu Ala Ala Ile Tyr Ile Gly Asp Ser Phe Cys Ala Gly Ser Leu Val
            420                 425                 430

His Thr Cys Trp Val Val Ser Ala Ala His Cys Phe Ser His Ser Pro
        435                 440                 445

Pro Arg Asp Ser Val Ser Val Val Leu Gly Gln His Phe Phe Asn Arg
450                 455                 460

Thr Thr Asp Val Thr Gln Thr Phe Gly Ile Glu Lys Tyr Ile Pro Tyr
465                 470                 475                 480

Thr Leu Tyr Ser Val Phe Asn Pro Ser Asp His Asp Leu Val Leu Ile
                485                 490                 495

Arg Leu Lys Lys Lys Gly Asp Arg Cys Ala Thr Arg Ser Gln Phe Val
            500                 505                 510

Gln Pro Ile Cys Leu Pro Glu Pro Gly Ser Thr Phe Pro Ala Gly His
        515                 520                 525

Lys Cys Gln Ile Ala Gly Trp Gly His Leu Asp Glu Asn Val Ser Gly
530                 535                 540

Tyr Ser Ser Ser Leu Arg Glu Ala Leu Val Pro Leu Val Ala Asp His
545                 550                 555                 560

Lys Cys Ser Ser Pro Glu Val Tyr Gly Ala Asp Ile Ser Pro Asn Met
                565                 570                 575

Leu Cys Ala Gly Tyr Phe Asp Cys Lys Ser Asp Ala Cys Gln Gly Asp
            580                 585                 590

Ser Gly Gly Pro Leu Ala Cys Glu Lys Asn Gly Val Ala Tyr Leu Tyr
        595                 600                 605

Gly Ile Ile Ser Trp Gly Asp Gly Cys Gly Arg Leu His Lys Pro Gly
610                 615                 620

Val Tyr Thr Arg Val Ala Asn Tyr Val Asp Trp Ile Asn Asp Arg Ile
625                 630                 635                 640
```

```
Arg Pro Pro Arg Arg Leu Val Ala Pro Ser
            645                 650

<210> SEQ ID NO 20
<211> LENGTH: 283
<212> TYPE: PRT
<213> ORGANISM: Homo sapiens

<400> SEQUENCE: 20

Val Gln Leu Ser Pro Asp Leu Leu Ala Thr Leu Pro Glu Pro Ala Ser
1               5                   10                  15

Pro Gly Arg Gln Ala Cys Gly Arg Arg His Lys Lys Arg Thr Phe Leu
            20                  25                  30

Arg Pro Arg Ile Ile Gly Gly Ser Ser Leu Pro Gly Ser His Pro
        35                  40                  45

Trp Leu Ala Ala Ile Tyr Ile Gly Asp Ser Phe Cys Ala Gly Ser Leu
    50                  55                  60

Val His Thr Cys Trp Val Val Ser Ala Ala His Cys Phe Ser His Ser
65                  70                  75                  80

Pro Pro Arg Asp Ser Val Ser Val Leu Gly Gln His Phe Phe Asn
            85                  90                  95

Arg Thr Thr Asp Val Thr Gln Thr Phe Gly Ile Glu Lys Tyr Ile Pro
            100                 105                 110

Tyr Thr Leu Tyr Ser Val Phe Asn Pro Ser Asp His Asp Leu Val Leu
            115                 120                 125

Ile Arg Leu Lys Lys Lys Gly Asp Arg Cys Ala Thr Arg Ser Gln Phe
        130                 135                 140

Val Gln Pro Ile Cys Leu Pro Glu Pro Gly Ser Thr Phe Pro Ala Gly
145                 150                 155                 160

His Lys Cys Gln Ile Ala Gly Trp Gly His Leu Asp Glu Asn Val Ser
                165                 170                 175

Gly Tyr Ser Ser Ser Leu Arg Glu Ala Leu Val Pro Leu Val Ala Asp
            180                 185                 190

His Lys Cys Ser Ser Pro Glu Val Tyr Gly Ala Asp Ile Ser Pro Asn
        195                 200                 205

Met Leu Cys Ala Gly Tyr Phe Asp Cys Lys Ser Asp Ala Cys Gln Gly
    210                 215                 220

Asp Ser Gly Gly Pro Leu Ala Cys Glu Lys Asn Gly Val Ala Tyr Leu
225                 230                 235                 240

Tyr Gly Ile Ile Ser Trp Gly Asp Gly Cys Gly Arg Leu His Lys Pro
                245                 250                 255

Gly Val Tyr Thr Arg Val Ala Asn Tyr Val Asp Trp Ile Asn Asp Arg
            260                 265                 270

Ile Arg Pro Pro Arg Arg Leu Val Ala Pro Ser
        275                 280

<210> SEQ ID NO 21
<211> LENGTH: 239
<212> TYPE: PRT
<213> ORGANISM: Homo sapiens

<400> SEQUENCE: 21

Ile Ile Gly Gly Ser Ser Leu Pro Gly Ser His Pro Trp Leu Ala
1               5                   10                  15

Ala Ile Tyr Ile Gly Asp Ser Phe Cys Ala Gly Ser Leu Val His Thr
            20                  25                  30
```

```
Cys Trp Val Val Ser Ala Ala His Cys Phe Ser His Ser Pro Pro Arg
            35                  40                  45

Asp Ser Val Ser Val Val Leu Gly Gln His Phe Phe Asn Arg Thr Thr
 50                  55                  60

Asp Val Thr Gln Thr Phe Gly Ile Glu Lys Tyr Ile Pro Tyr Thr Leu
 65                  70                  75                  80

Tyr Ser Val Phe Asn Pro Ser Asp His Asp Leu Val Leu Ile Arg Leu
                 85                  90                  95

Lys Lys Lys Gly Asp Arg Cys Ala Thr Arg Ser Gln Phe Val Gln Pro
            100                 105                 110

Ile Cys Leu Pro Glu Pro Gly Ser Thr Phe Pro Ala Gly His Lys Cys
            115                 120                 125

Gln Ile Ala Gly Trp Gly His Leu Asp Glu Asn Val Ser Gly Tyr Ser
            130                 135                 140

Ser Ser Leu Arg Glu Ala Leu Val Pro Leu Val Ala Asp His Lys Cys
145                 150                 155                 160

Ser Ser Pro Glu Val Tyr Gly Ala Asp Ile Ser Pro Asn Met Leu Cys
                165                 170                 175

Ala Gly Tyr Phe Asp Cys Lys Ser Asp Ala Cys Gln Gly Asp Ser Gly
            180                 185                 190

Gly Pro Leu Ala Cys Glu Lys Asn Gly Val Ala Tyr Leu Tyr Gly Ile
            195                 200                 205

Ile Ser Trp Gly Asp Gly Cys Gly Arg Leu His Lys Pro Gly Val Tyr
            210                 215                 220

Thr Arg Val Ala Asn Tyr Val Asp Trp Ile Asn Asp Arg Ile Arg
225                 230                 235

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Ser Tyr Thr Thr Pro Pro Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Gly Thr Tyr Ile His
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Trp Ala Trp Pro Ala Phe Asp Tyr
```

<210> SEQ ID NO 25
<211> LENGTH: 248
<212> TYPE: PRT
<213> ORGANISM: Homo sapiens

<400> SEQUENCE: 25

```
Ile Ile Gly Gly Ser Ser Leu Pro Gly Ser His Pro Trp Leu Ala
1               5                   10                  15

Ala Ile Tyr Ile Gly Asp Ser Phe Cys Ala Gly Ser Leu Val His Thr
            20                  25                  30

Cys Trp Val Val Ser Ala Ala His Cys Phe Ser His Ser Pro Pro Arg
        35                  40                  45

Asp Ser Val Ser Val Val Leu Gly Gln His Phe Phe Asn Arg Thr Thr
    50                  55                  60

Asp Val Thr Gln Thr Phe Gly Ile Glu Lys Tyr Ile Pro Tyr Thr Leu
65                  70                  75                  80

Tyr Ser Val Phe Asn Pro Ser Asp His Asp Leu Val Leu Ile Arg Leu
                85                  90                  95

Lys Lys Lys Gly Asp Arg Cys Ala Thr Arg Ser Gln Phe Val Gln Pro
            100                 105                 110

Ile Cys Leu Pro Glu Pro Gly Ser Thr Phe Pro Ala Gly His Lys Cys
        115                 120                 125

Gln Ile Ala Gly Trp Gly His Leu Asp Glu Asn Val Ser Gly Tyr Ser
    130                 135                 140

Ser Ser Leu Arg Glu Ala Leu Val Pro Leu Val Ala Asp His Lys Cys
145                 150                 155                 160

Ser Ser Pro Glu Val Tyr Gly Ala Asp Ile Ser Pro Asn Met Leu Cys
                165                 170                 175

Ala Gly Tyr Phe Asp Cys Lys Ser Asp Ala Cys Gln Gly Asp Ser Gly
            180                 185                 190

Gly Pro Leu Ala Cys Glu Lys Asn Gly Val Ala Tyr Leu Tyr Gly Ile
        195                 200                 205

Ile Ser Trp Gly Asp Gly Cys Gly Arg Leu His Lys Pro Gly Val Tyr
    210                 215                 220

Thr Arg Val Ala Asn Tyr Val Asp Trp Ile Asn Asp Arg Ile Arg Pro
225                 230                 235                 240

Pro Arg Arg Leu Val Ala Pro Ser
                245
```

<210> SEQ ID NO 26
<211> LENGTH: 223
<212> TYPE: PRT
<213> ORGANISM: Homo sapiens

<400> SEQUENCE: 26

```
Ile Val Gly Gly Tyr Thr Cys Gly Ala Asn Thr Val Pro Tyr Gln Val
1               5                   10                  15

Ser Leu Asn Ser Gly Tyr His Phe Cys Gly Gly Ser Leu Ile Asn Ser
            20                  25                  30

Gln Trp Val Val Ser Ala Ala His Cys Tyr Lys Ser Gly Ile Gln Val
        35                  40                  45

Arg Leu Gly Glu Asp Asn Ile Asn Val Val Glu Gly Asn Glu Gln Phe
    50                  55                  60

Ile Ser Ala Ser Lys Ser Ile Val His Pro Ser Tyr Asn Ser Asn Thr
```

```
            65                  70                  75                  80
Leu Asn Asn Asp Ile Met Leu Ile Lys Leu Lys Ser Ala Ala Ser Leu
                    85                  90                  95

Asn Ser Arg Val Ala Ser Ile Ser Leu Pro Thr Ser Cys Ala Ser Ala
                100                 105                 110

Gly Thr Gln Cys Leu Ile Ser Gly Trp Gly Asn Thr Lys Ser Ser Gly
                115                 120                 125

Thr Ser Tyr Pro Asp Val Leu Lys Cys Leu Lys Ala Pro Ile Leu Ser
        130                 135                 140

Asp Ser Ser Cys Lys Ser Ala Tyr Pro Gly Gln Ile Thr Ser Asn Met
145                 150                 155                 160

Phe Cys Ala Gly Tyr Leu Glu Gly Gly Lys Asp Ser Cys Gln Gly Asp
                165                 170                 175

Ser Gly Gly Pro Val Val Cys Ser Gly Lys Leu Gln Gly Ile Val Ser
                180                 185                 190

Trp Gly Ser Gly Cys Ala Gln Lys Asn Lys Pro Gly Val Tyr Thr Lys
        195                 200                 205

Val Cys Asn Tyr Val Ser Trp Ile Lys Gln Thr Ile Ala Ser Asn
    210                 215                 220

<210> SEQ ID NO 27
<211> LENGTH: 241
<212> TYPE: PRT
<213> ORGANISM: Homo sapiens

<400> SEQUENCE: 27

Val Val Gly Gly Thr Asp Ala Asp Glu Gly Glu Trp Pro Trp Gln Val
1               5                   10                  15

Ser Leu His Ala Leu Gly Gln Gly His Ile Cys Gly Ala Ser Leu Ile
                20                  25                  30

Ser Pro Asn Trp Leu Val Ser Ala Ala His Cys Tyr Ile Asp Asp Arg
            35                  40                  45

Gly Phe Arg Tyr Ser Asp Pro Thr Gln Trp Thr Ala Phe Leu Gly Leu
    50                  55                  60

His Asp Gln Ser Gln Arg Ser Ala Pro Gly Val Gln Glu Arg Arg Leu
65                  70                  75                  80

Lys Arg Ile Ile Ser His Pro Phe Phe Asn Asp Phe Thr Phe Asp Tyr
                85                  90                  95

Asp Ile Ala Leu Leu Glu Leu Glu Lys Pro Ala Glu Tyr Ser Ser Met
                100                 105                 110

Val Arg Pro Ile Cys Leu Pro Asp Ala Ser His Val Phe Pro Ala Gly
            115                 120                 125

Lys Ala Ile Trp Val Thr Gly Trp Gly His Thr Gln Tyr Gly Gly Thr
    130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
    195                 200                 205

Val Val Ser Trp Gly Asp Gly Cys Ala Gln Arg Asn Lys Pro Gly Val
    210                 215                 220
```

Tyr Thr Arg Leu Pro Leu Phe Arg Asp Trp Ile Lys Glu Asn Thr Gly
225                 230                 235                 240

Val

<210> SEQ ID NO 28
<211> LENGTH: 255
<212> TYPE: PRT
<213> ORGANISM: Homo sapiens

<400> SEQUENCE: 28

Ile Val Gly Gly Arg Asp Thr Ser Leu Gly Arg Trp Pro Trp Gln Val
1               5                   10                  15

Ser Leu Arg Tyr Asp Gly Ala His Leu Cys Gly Gly Ser Leu Leu Ser
                20                  25                  30

Gly Asp Trp Val Leu Thr Ala Ala His Cys Phe Pro Glu Arg Asn Arg
            35                  40                  45

Val Leu Ser Arg Trp Arg Val Phe Ala Gly Ala Val Ala Gln Ala Ser
50                  55                  60

Pro His Gly Leu Gln Leu Gly Val Gln Ala Val Val Tyr His Gly Gly
65                  70                  75                  80

Tyr Leu Pro Phe Arg Asp Pro Asn Ser Glu Glu Asn Ser Asn Asp Ile
                85                  90                  95

Ala Leu Val His Leu Ser Ser Pro Leu Pro Leu Thr Glu Tyr Ile Gln
            100                 105                 110

Pro Val Cys Leu Pro Ala Ala Gly Gln Ala Leu Val Asp Gly Lys Ile
        115                 120                 125

Cys Thr Val Thr Gly Trp Gly Asn Thr Gln Tyr Tyr Gly Gln Gln Ala
130                 135                 140

Gly Val Leu Gln Glu Ala Arg Val Pro Ile Ile Ser Asn Asp Val Cys
145                 150                 155                 160

Asn Gly Ala Asp Phe Tyr Gly Asn Gln Ile Lys Pro Lys Met Phe Cys
                165                 170                 175

Ala Gly Tyr Pro Glu Gly Gly Ile Asp Ala Cys Gln Gly Asp Ser Gly
            180                 185                 190

Gly Pro Phe Val Cys Glu Asp Ser Ile Ser Arg Thr Pro Arg Trp Arg
        195                 200                 205

Leu Cys Gly Ile Val Ser Trp Gly Thr Gly Cys Ala Leu Ala Gln Lys
210                 215                 220

Pro Gly Val Tyr Thr Lys Val Ser Asp Phe Arg Glu Trp Ile Phe Gln
225                 230                 235                 240

Ala Ile Lys Thr His Ser Glu Ala Ser Gly Met Val Thr Gln Leu
                245                 250                 255

<210> SEQ ID NO 29
<211> LENGTH: 253
<212> TYPE: PRT
<213> ORGANISM: Homo sapiens

<400> SEQUENCE: 29

Ile Ile Gly Gly Glu Phe Thr Thr Ile Glu Asn Gln Pro Trp Phe Ala
1               5                   10                  15

Ala Ile Tyr Arg Arg His Arg Gly Gly Ser Val Thr Tyr Val Cys Gly
                20                  25                  30

Gly Ser Leu Ile Ser Pro Cys Trp Val Ile Ser Ala Thr His Cys Phe
            35                  40                  45

Ile Asp Tyr Pro Lys Lys Glu Asp Tyr Ile Val Tyr Leu Gly Arg Ser

Arg Leu Asn Ser Asn Thr Gln Gly Glu Met Lys Phe Glu Val Glu Asn
65                  70                  75                  80

Leu Ile Leu His Lys Asp Tyr Ser Ala Asp Thr Leu Ala His His Asn
                85                  90                  95

Asp Ile Ala Leu Leu Lys Ile Arg Ser Lys Glu Gly Arg Cys Ala Gln
            100                 105                 110

Pro Ser Arg Thr Ile Gln Thr Ile Cys Leu Pro Ser Met Tyr Asn Asp
            115                 120                 125

Pro Gln Phe Gly Thr Ser Cys Glu Ile Thr Gly Phe Gly Lys Glu Asn
            130                 135                 140

Ser Thr Asp Tyr Leu Tyr Pro Glu Gln Leu Lys Met Thr Val Val Lys
145                 150                 155                 160

Leu Ile Ser His Arg Glu Cys Gln Gln Pro His Tyr Tyr Gly Ser Glu
                165                 170                 175

Val Thr Thr Lys Met Leu Cys Ala Ala Asp Pro Gln Trp Lys Thr Asp
                180                 185                 190

Ser Cys Gln Gly Asp Ser Gly Gly Pro Leu Val Cys Ser Leu Gln Gly
                195                 200                 205

Arg Met Thr Leu Thr Gly Ile Val Ser Trp Gly Arg Gly Cys Ala Leu
210                 215                 220

Lys Asp Lys Pro Gly Val Tyr Thr Arg Val Ser His Phe Leu Pro Trp
225                 230                 235                 240

Ile Arg Ser His Thr Lys Glu Glu Asn Gly Leu Ala Leu
                245                 250

<210> SEQ ID NO 30
<211> LENGTH: 254
<212> TYPE: PRT
<213> ORGANISM: Homo sapiens

<400> SEQUENCE: 30

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
                20                  25                  30

Thr Ile Trp Val Val Ser Ala Ala His Cys Phe Asp Lys Ile Lys Asn
            35                  40                  45

Trp Arg Asn Leu Ile Ala Val Leu Gly Glu His Asp Leu Ser Glu His
    50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                85                  90                  95

His Gln Pro Val Val Leu Thr Asp His Val Val Pro Leu Cys Leu Pro
            100                 105                 110

Glu Arg Thr Phe Ser Glu Arg Thr Leu Ala Phe Val Arg Phe Ser Leu
            115                 120                 125

Val Ser Gly Trp Gly Gln Leu Leu Asp Arg Gly Ala Thr Ala Leu Glu
            130                 135                 140

Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

-continued

Cys Ala Gly Tyr Ser Asp Gly Ser Lys Asp Ser Cys Lys Gly Asp Ser
                180                 185                 190

Gly Gly Pro His Ala Thr His Tyr Arg Gly Thr Trp Tyr Leu Thr Gly
            195                 200                 205

Ile Val Ser Trp Gly Gln Gly Cys Ala Thr Val Gly His Phe Gly Val
210                 215                 220

Tyr Thr Arg Val Ser Gln Tyr Ile Glu Trp Leu Gln Lys Leu Met Arg
225                 230                 235                 240

Ser Glu Pro Arg Pro Gly Val Leu Leu Arg Ala Pro Phe Pro
                245                 250

<210> SEQ ID NO 31
<211> LENGTH: 259
<212> TYPE: PRT
<213> ORGANISM: Homo sapiens

<400> SEQUENCE: 31

Ile Val Glu Gly Ser Asp Ala Glu Ile Gly Met Ser Pro Trp Gln Val
1               5                   10                  15

Met Leu Phe Arg Lys Ser Pro Gln Glu Leu Leu Cys Gly Ala Ser Leu
            20                  25                  30

Ile Ser Asp Arg Trp Val Leu Thr Ala Ala His Cys Leu Leu Tyr Pro
        35                  40                  45

Pro Trp Asp Lys Asn Phe Thr Glu Asn Asp Leu Leu Val Arg Ile Gly
    50                  55                  60

Lys His Ser Arg Thr Arg Tyr Glu Arg Asn Ile Glu Lys Ile Ser Met
65                  70                  75                  80

Leu Glu Lys Ile Tyr Ile His Pro Arg Tyr Asn Trp Arg Glu Asn Leu
                85                  90                  95

Asp Arg Asp Ile Ala Leu Met Lys Leu Lys Lys Pro Val Ala Phe Ser
            100                 105                 110

Asp Tyr Ile His Pro Val Cys Leu Pro Asp Arg Glu Thr Ala Ala Ser
        115                 120                 125

Leu Leu Gln Ala Gly Tyr Lys Gly Arg Val Thr Gly Trp Gly Asn Leu
    130                 135                 140

Lys Glu Thr Trp Thr Ala Asn Val Gly Lys Gly Gln Pro Ser Val Leu
145                 150                 155                 160

Gln Val Val Asn Leu Pro Ile Val Glu Arg Pro Val Cys Lys Asp Ser
                165                 170                 175

Thr Arg Ile Arg Ile Thr Asp Asn Met Phe Cys Ala Gly Tyr Lys Pro
            180                 185                 190

Asp Glu Gly Lys Arg Gly Asp Ala Cys Glu Gly Asp Ser Gly Gly Pro
        195                 200                 205

Phe Val Met Lys Ser Pro Phe Asn Asn Arg Trp Tyr Gln Met Gly Ile
    210                 215                 220

Val Ser Trp Gly Glu Gly Cys Asp Arg Asp Gly Lys Tyr Gly Phe Tyr
225                 230                 235                 240

Thr His Val Phe Arg Leu Lys Lys Trp Ile Gln Lys Val Ile Asp Gln
                245                 250                 255

Phe Gly Glu

<210> SEQ ID NO 32
<211> LENGTH: 243
<212> TYPE: PRT
<213> ORGANISM: Homo sapiens

<400> SEQUENCE: 32

```
Val Val Gly Gly Leu Val Ala Leu Arg Gly Ala His Pro Tyr Ile Ala
1               5                   10                  15
Ala Leu Tyr Trp Gly His Ser Phe Cys Ala Gly Ser Leu Ile Ala Pro
            20                  25                  30
Cys Trp Val Leu Thr Ala Ala His Cys Leu Gln Asp Arg Pro Ala Pro
        35                  40                  45
Glu Asp Leu Thr Val Val Leu Gly Gln Glu Arg Arg Asn His Ser Cys
50                  55                  60
Glu Pro Cys Gln Thr Leu Ala Val Arg Ser Tyr Arg Leu His Glu Ala
65                  70                  75                  80
Phe Ser Pro Val Ser Tyr Gln His Asp Leu Ala Leu Leu Arg Leu Gln
                85                  90                  95
Glu Asp Ala Asp Gly Ser Cys Ala Leu Leu Ser Pro Tyr Val Gln Pro
            100                 105                 110
Val Cys Leu Pro Ser Gly Ala Ala Arg Pro Ser Glu Thr Thr Leu Cys
        115                 120                 125
Gln Val Ala Gly Trp Gly His Gln Phe Glu Gly Ala Glu Glu Tyr Ala
130                 135                 140
Ser Phe Leu Gln Glu Ala Gln Val Pro Phe Leu Ser Leu Glu Arg Cys
145                 150                 155                 160
Ser Ala Pro Asp Val His Gly Ser Ser Ile Leu Pro Gly Met Leu Cys
                165                 170                 175
Ala Gly Phe Leu Glu Gly Gly Thr Asp Ala Cys Gln Gly Asp Ser Gly
            180                 185                 190
Gly Pro Leu Val Cys Glu Asp Gln Ala Ala Glu Arg Arg Leu Thr Leu
        195                 200                 205
Gln Gly Ile Ile Ser Trp Gly Ser Gly Cys Gly Asp Arg Asn Lys Pro
210                 215                 220
Gly Val Tyr Thr Asp Val Ala Tyr Tyr Leu Ala Trp Ile Arg Glu His
225                 230                 235                 240
Thr Val Ser
```

<210> SEQ ID NO 33
<211> LENGTH: 252
<212> TYPE: PRT
<213> ORGANISM: Homo sapiens

<400> SEQUENCE: 33

```
Ile Lys Gly Gly Leu Phe Ala Asp Ile Ala Ser His Pro Trp Gln Ala
1               5                   10                  15
Ala Ile Phe Ala Lys His Arg Arg Ser Pro Gly Glu Arg Phe Leu Cys
            20                  25                  30
Gly Gly Ile Leu Ile Ser Ser Cys Trp Ile Leu Ser Ala Ala His Cys
        35                  40                  45
Phe Gln Glu Arg Phe Pro Pro His His Leu Thr Val Ile Leu Gly Arg
50                  55                  60
Thr Tyr Arg Val Val Pro Gly Glu Glu Glu Gln Lys Phe Glu Val Glu
65                  70                  75                  80
Lys Tyr Ile Val His Lys Glu Phe Asp Asp Asp Thr Tyr Asp Asn Asp
                85                  90                  95
Ile Ala Leu Leu Gln Leu Lys Ser Asp Ser Ser Arg Cys Ala Gln Glu
            100                 105                 110
Ser Ser Val Val Arg Thr Val Cys Leu Pro Pro Ala Asp Leu Gln Leu
```

```
                    115                 120                 125
Pro Asp Trp Thr Glu Cys Glu Leu Ser Gly Tyr Gly Lys His Glu Ala
    130                 135                 140

Leu Ser Pro Phe Tyr Ser Glu Arg Leu Lys Glu Ala His Val Arg Leu
145                 150                 155                 160

Tyr Pro Ser Ser Arg Cys Thr Ser Gln His Leu Leu Asn Arg Thr Val
                165                 170                 175

Thr Asp Asn Met Leu Cys Ala Gly Asp Thr Arg Ser Gly Gly Pro Gln
            180                 185                 190

Ala Asn Leu His Asp Ala Cys Gln Gly Asp Ser Gly Gly Pro Leu Val
            195                 200                 205

Cys Leu Asn Asp Gly Arg Met Thr Leu Val Gly Ile Ile Ser Trp Gly
210                 215                 220

Leu Gly Cys Gly Gln Lys Asp Val Pro Gly Val Tyr Thr Lys Val Thr
225                 230                 235                 240

Asn Tyr Leu Asp Trp Ile Arg Asp Asn Met Arg Pro
                245                 250
```

<210> SEQ ID NO 34
<211> LENGTH: 51
<212> TYPE: PRT
<213> ORGANISM: Homo sapiens

<400> SEQUENCE: 34

```
Cys Leu Ala Ser Asn Lys Val Gly Arg Cys Arg Gly Ser Phe Pro Arg
1               5                   10                  15

Trp Tyr Tyr Asp Pro Thr Glu Gln Ile Cys Lys Ser Phe Val Tyr Gly
                20                  25                  30

Gly Cys Leu Gly Asn Lys Asn Asn Tyr Leu Arg Glu Glu Glu Cys Ile
            35                  40                  45

Leu Ala Cys
    50
```

<210> SEQ ID NO 35
<211> LENGTH: 51
<212> TYPE: PRT
<213> ORGANISM: Homo sapiens

<400> SEQUENCE: 35

```
Cys Leu Val Ser Lys Val Val Gly Arg Cys Arg Ala Ser Met Pro Arg
1               5                   10                  15

Trp Trp Tyr Asn Val Thr Asp Gly Ser Cys Gln Leu Phe Val Tyr Gly
                20                  25                  30

Gly Cys Asp Gly Asn Ser Asn Asn Tyr Leu Thr Lys Glu Glu Cys Leu
            35                  40                  45

Lys Lys Cys
    50
```

<210> SEQ ID NO 36
<211> LENGTH: 51
<212> TYPE: PRT
<213> ORGANISM: Homo sapiens

<400> SEQUENCE: 36

```
Cys Val Asp Leu Pro Asp Thr Gly Leu Cys Lys Glu Ser Ile Pro Arg
1               5                   10                  15

Trp Tyr Tyr Asn Pro Phe Ser Glu His Cys Ala Arg Phe Thr Tyr Gly
                20                  25                  30
```

Gly Cys Tyr Gly Asn Lys Asn Phe Glu Glu Gln Gln Cys Leu
        35                  40                  45
Glu Ser Cys
    50

<210> SEQ ID NO 37
<211> LENGTH: 51
<212> TYPE: PRT
<213> ORGANISM: Homo sapiens

<400> SEQUENCE: 37

Cys Thr Ala Asn Ala Val Thr Gly Pro Cys Arg Ala Ser Phe Pro Arg
1               5                   10                  15
Trp Tyr Phe Asp Val Glu Arg Asn Ser Cys Asn Asn Phe Ile Tyr Gly
                20                  25                  30
Gly Cys Arg Gly Asn Lys Asn Ser Tyr Arg Ser Glu Glu Ala Cys Met
        35                  40                  45
Leu Arg Cys
    50

<210> SEQ ID NO 38
<211> LENGTH: 51
<212> TYPE: PRT
<213> ORGANISM: Homo sapiens

<400> SEQUENCE: 38

Cys Ala Phe Lys Ala Asp Asp Gly Pro Cys Lys Ala Ile Met Lys Arg
1               5                   10                  15
Phe Phe Phe Asn Ile Phe Thr Arg Gln Cys Glu Glu Phe Ile Tyr Gly
                20                  25                  30
Gly Cys Glu Gly Asn Gln Asn Arg Phe Glu Ser Leu Glu Glu Cys Lys
        35                  40                  45
Lys Met Cys
    50

<210> SEQ ID NO 39
<211> LENGTH: 51
<212> TYPE: PRT
<213> ORGANISM: Homo sapiens

<400> SEQUENCE: 39

Cys Phe Leu Glu Glu Asp Pro Gly Ile Cys Arg Gly Tyr Ile Thr Arg
1               5                   10                  15
Tyr Phe Tyr Asn Asn Gln Thr Lys Gln Cys Glu Arg Phe Lys Tyr Gly
                20                  25                  30
Gly Cys Leu Gly Asn Met Asn Asn Phe Glu Thr Leu Glu Glu Cys Lys
        35                  40                  45
Asn Ile Cys
    50

<210> SEQ ID NO 40
<211> LENGTH: 51
<212> TYPE: PRT
<213> ORGANISM: Homo sapiens

<400> SEQUENCE: 40

Cys Leu Thr Pro Ala Asp Arg Gly Leu Cys Arg Ala Asn Glu Asn Arg
1               5                   10                  15
Phe Tyr Tyr Asn Ser Val Ile Gly Lys Cys Arg Pro Phe Lys Tyr Ser

```
                20                  25                  30
Gly Cys Gly Gly Asn Glu Asn Asn Phe Thr Ser Lys Gln Glu Cys Leu
            35                  40                  45

Arg Ala Cys
        50

<210> SEQ ID NO 41
<211> LENGTH: 51
<212> TYPE: PRT
<213> ORGANISM: Homo sapiens

<400> SEQUENCE: 41

Cys Leu Glu Pro Pro Tyr Thr Gly Pro Cys Lys Ala Arg Ile Ile Arg
1               5                   10                  15

Tyr Phe Tyr Asn Ala Lys Ala Gly Leu Cys Gln Thr Phe Val Tyr Gly
                20                  25                  30

Gly Cys Arg Ala Lys Arg Asn Asn Phe Lys Ser Ala Glu Asp Cys Met
            35                  40                  45

Arg Thr Cys
        50

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Gly Thr
                20                  25                  30

Tyr Ile His Trp Val Arg Gln Ala Pro Gly Lys Gly Leu Glu Trp Val
            35                  40                  45

Gly Gly Ile Tyr Pro Ala Gly Gly Ala Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ala Trp Pro Ala Phe Asp Tyr Trp Gly Gln Gly Thr Leu
            100                 105                 110

Val Thr Val Ser Ser
        115

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Gly Thr Tyr Ile His
1               5

<210> SEQ ID NO 44
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Phe Thr Phe Asn Gly Thr Tyr Ile His
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Ile Tyr Pro Ala Gly Gly Ala Thr Tyr Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Trp Trp Ala Trp Pro Ala Phe Asp Tyr
1               5                   10

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Ile Tyr Pro Ala Gly Gly Ala Thr Tyr Tyr Ala Asp Ser Val
1               5                   10                  15

Lys Gly
```